US012336819B2

(12) United States Patent
Lee et al.

(10) Patent No.: US 12,336,819 B2
(45) Date of Patent: Jun. 24, 2025

(54) ANALYTE SENSOR BREAK-IN MITIGATION

(71) Applicant: DexCom, Inc., San Diego, CA (US)

(72) Inventors: Ted Tang Lee, San Diego, CA (US); Shanger Wang, San Diego, CA (US)

(73) Assignee: Dexcom, Inc., San Diego, CA (US)

(*) Notice: Subject to any disclaimer, the term of this patent is extended or adjusted under 35 U.S.C. 154(b) by 0 days.

(21) Appl. No.: 16/728,945

(22) Filed: Dec. 27, 2019

(65) Prior Publication Data

US 2020/0205705 A1   Jul. 2, 2020

Related U.S. Application Data

(60) Provisional application No. 62/786,116, filed on Dec. 28, 2018, provisional application No. 62/786,228, (Continued)

(51) Int. Cl.
A61B 5/1495 (2006.01)
A61B 5/00 (2006.01)
A61B 5/0537 (2021.01)
A61B 5/145 (2006.01)
A61B 5/1473 (2006.01)
A61B 5/1486 (2006.01)
G01N 27/22 (2006.01)
(Continued)

(52) U.S. Cl.
CPC .......... A61B 5/1495 (2013.01); A61B 5/0537 (2013.01); A61B 5/14532 (2013.01); A61B 5/14546 (2013.01); A61B 5/1473 (2013.01); A61B 5/1486 (2013.01); A61B 5/14865 (2013.01); A61B 5/6844 (2013.01); G01N 27/221 (2013.01); G01N 27/24 (2013.01); G01N 33/48707 (2013.01); A61B 5/0004 (2013.01); A61B 5/0031 (2013.01); A61B 2560/0223 (2013.01); A61B 2560/0252 (2013.01); A61B 2560/0276 (2013.01); G01N 27/026 (2013.01)

(58) Field of Classification Search
None
See application file for complete search history.

(56) References Cited

U.S. PATENT DOCUMENTS 4,340,457 A   7/1982 Kater
5,338,435 A   8/1994 Betts et al.
(Continued)

FOREIGN PATENT DOCUMENTS

WO   2004059286 A2   7/2004

OTHER PUBLICATIONS

International Search Report and Written Opinion dated Apr. 30, 2020 for Application No. PCT/US2019/068708.

Primary Examiner — Etsub D Berhanu
Assistant Examiner — Joseph A Tombers
(74) Attorney, Agent, or Firm — Schwegman, Lundberg & Woessner, P.A.

(57) ABSTRACT

Various examples described herein are directed to systems, apparatuses, and methods for mitigating break-in in an analyte sensor. An example analyte sensor system comprises an analyte sensor applicator comprising a needle; an analyte sensor comprising at least a working electrode and a reference electrode, the analyte sensor positioned at least partially within a lumen of the needle; and a hydrating agent positioned within the lumen of the needle to at least partially hydrate the needle.

15 Claims, 36 Drawing Sheets

Related U.S. Application Data filed on Dec. 28, 2018, provisional application No. 62/786,208, filed on Dec. 28, 2018, provisional application No. 62/786,166, filed on Dec. 28, 2018, provisional application No. 62/786,127, filed on Dec. 28, 2018.

(51) Int. Cl.
  *G01N 27/24* (2006.01)
  *G01N 33/487* (2006.01)
  *G01N 27/02* (2006.01)

(56) References Cited

U.S. PATENT DOCUMENTS

| | | | |
|---|---|---|---|
| 5,918,590 A * | 7/1999 | Burkett | C09K 5/18 |
| | | | 607/114 |
| 6,001,067 A | 12/1999 | Shults et al. | |
| 6,424,847 B1 | 7/2002 | Mastrototaro et al. | |
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 7,494,465 B2 | 2/2009 | Brister et al. | |
| 8,682,408 B2 | 3/2014 | Boock et al. | |
| 9,044,199 B2 | 6/2015 | Brister et al. | |
| 9,170,310 B2 | 10/2015 | Ma et al. | |
| 2005/0027463 A1 | 2/2005 | Goode et al. | |
| 2005/0179512 A1 | 8/2005 | Weyers et al. | |
| 2006/0020187 A1 | 1/2006 | Brister et al. | |
| 2007/0027385 A1 | 2/2007 | Brister et al. | |
| 2007/0128681 A1 | 6/2007 | Barman et al. | |
| 2007/0173710 A1 | 7/2007 | Petisce et al. | |
| 2007/0197890 A1 | 8/2007 | Boock et al. | |
| 2008/0108942 A1 | 5/2008 | Brister et al. | |
| 2008/0119703 A1 | 5/2008 | Brister et al. | |
| 2010/0292557 A1 * | 11/2010 | Pesach | A61B 5/1491 |
| | | | 607/113 |
| 2011/0024307 A1 | 2/2011 | Simpson et al. | |
| 2011/0144463 A1 * | 6/2011 | Pesach | A61B 5/150267 |
| | | | 600/345 |
| 2012/0004524 A1 | 1/2012 | Van Antwerp et al. | |
| 2012/0028805 A1 | 2/2012 | Hollis et al. | |
| 2012/0078071 A1 * | 3/2012 | Bohm | A61B 5/14532 |
| | | | 600/345 |
| 2012/0262298 A1 | 10/2012 | Böhm et al. | |
| 2013/0245981 A1 | 9/2013 | Estes et al. | |
| 2015/0289788 A1 * | 10/2015 | Simpson | A61B 5/14532 |
| | | | 600/345 |
| 2015/0351672 A1 | 12/2015 | Vanslyke et al. | |
| 2016/0058380 A1 * | 3/2016 | Lee | A61B 5/68335 |
| | | | 600/365 |
| 2016/0151010 A1 * | 6/2016 | Erez | A61B 5/15115 |
| | | | 600/576 |
| 2016/0235366 A1 * | 8/2016 | Holmes | A61B 5/6889 |
| 2018/0151280 A1 | 5/2018 | Pourrahimi | |
| 2018/0279928 A1 | 10/2018 | Previl | |
| 2018/0325430 A1 | 11/2018 | Vaddiraju et al. | |
| 2018/0353684 A1 * | 12/2018 | Kim | A61B 5/1477 |
| 2018/0372667 A1 | 12/2018 | Gupta | |
| 2019/0227022 A1 | 7/2019 | Harley-Trochimczyk et al. | |

\* cited by examiner

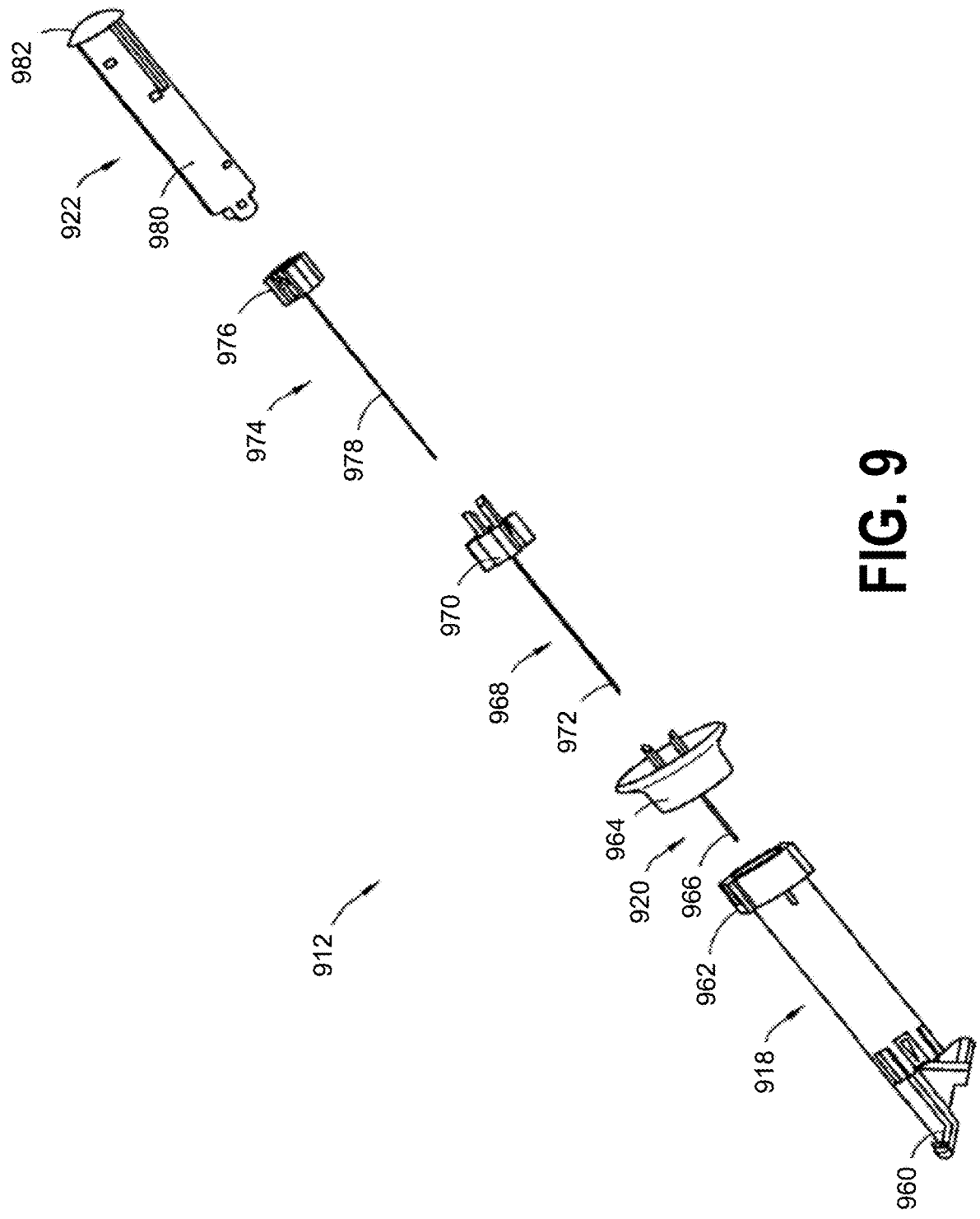

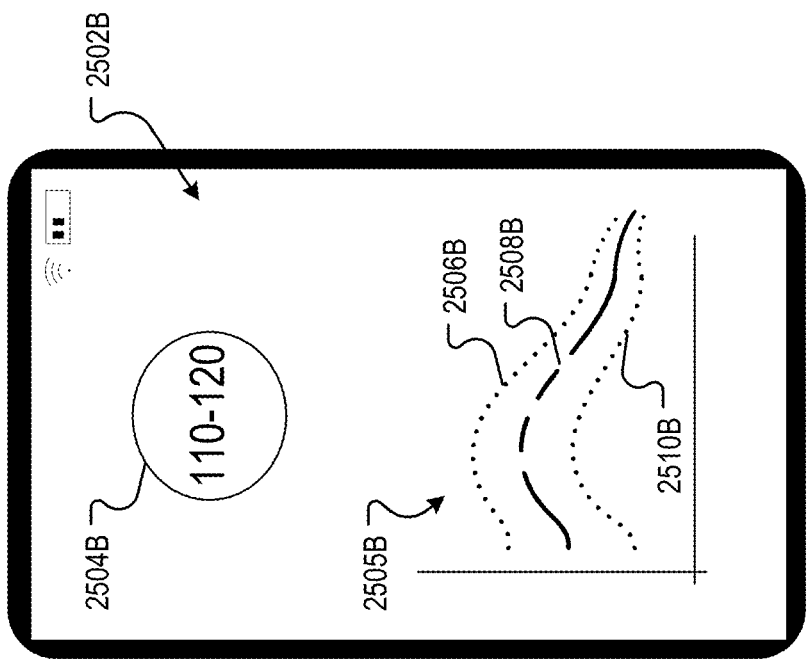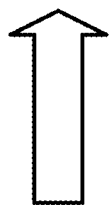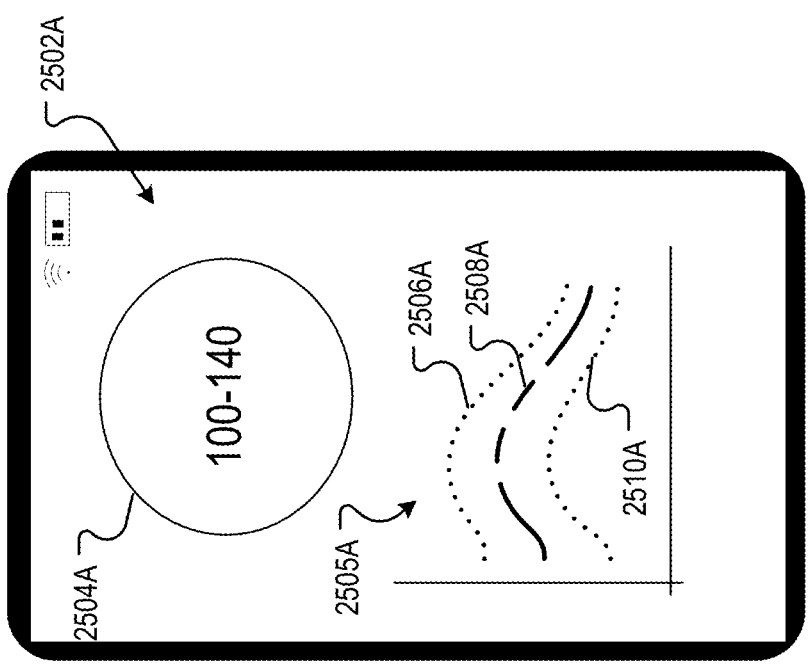
FIG. 25

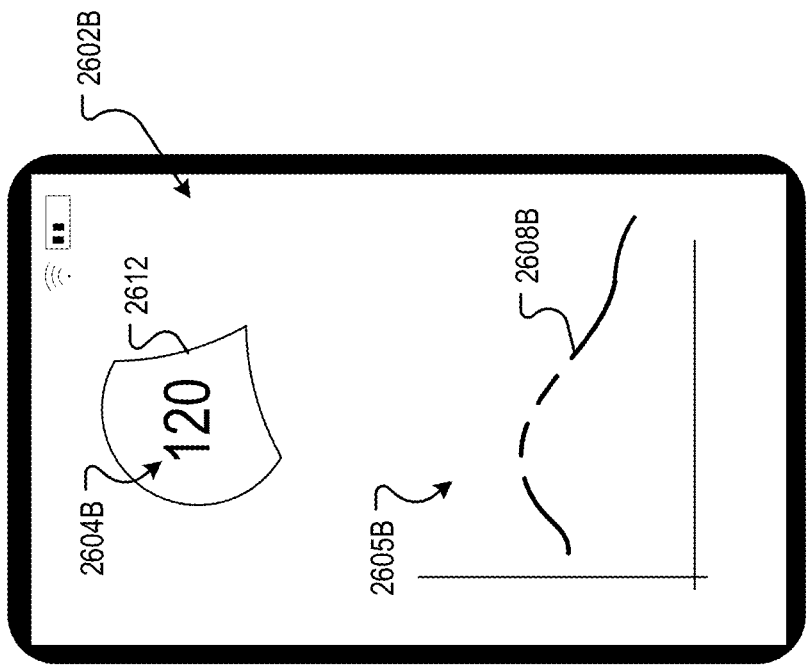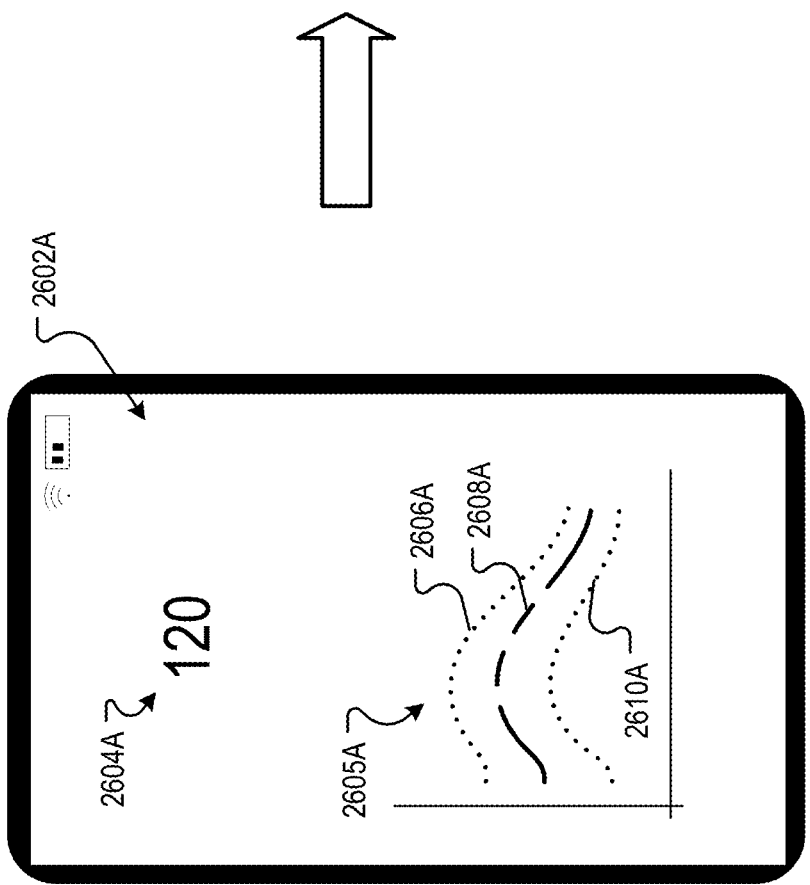
FIG. 26

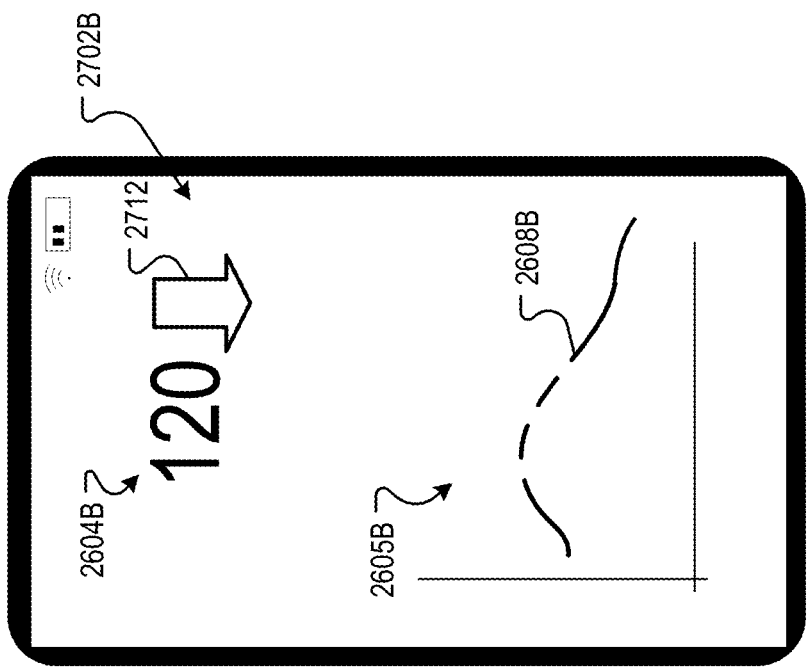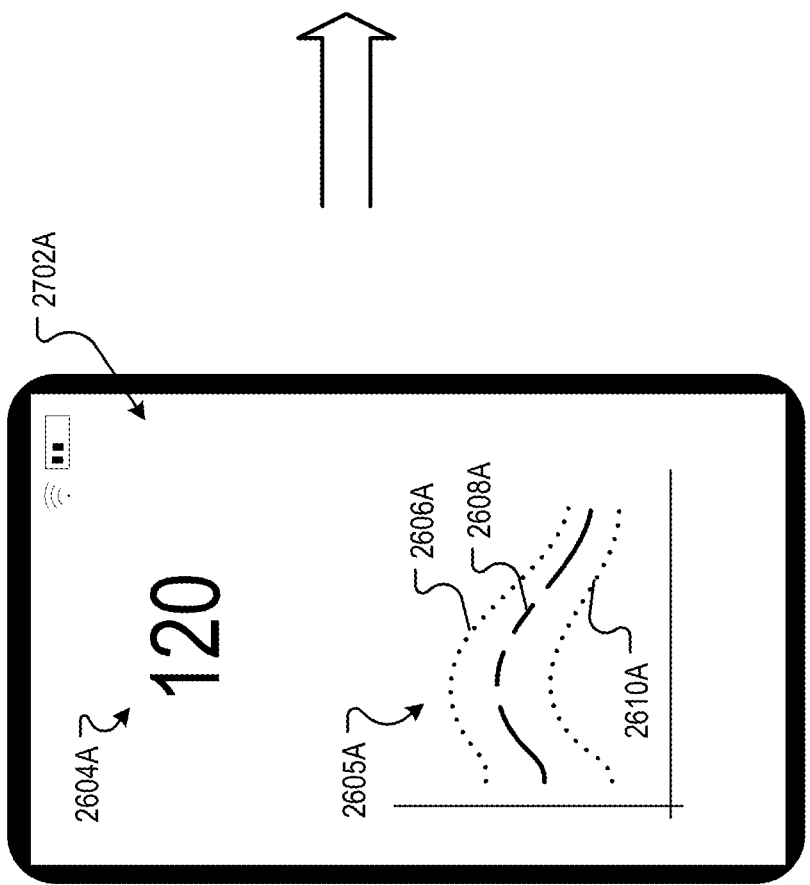
FIG. 27

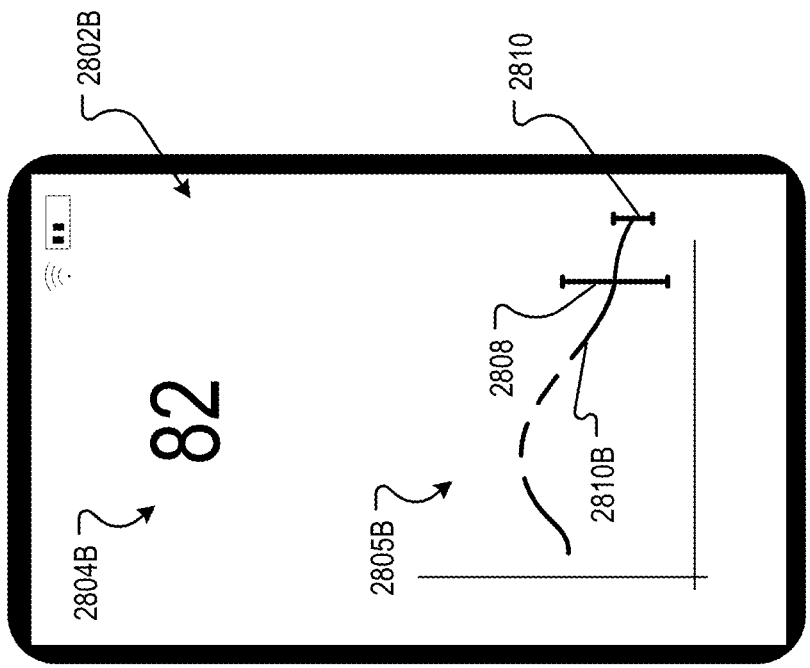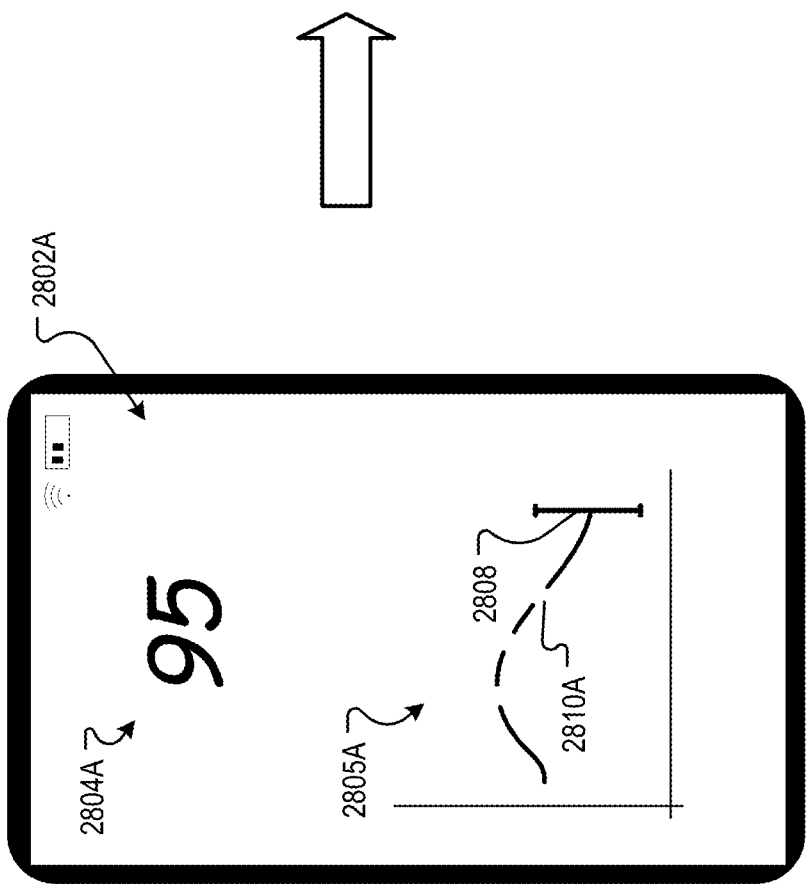
FIG. 28

ANALYTE SENSOR BREAK-IN MITIGATION

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application Ser. No. 62/786,228, filed on Dec. 28, 2018, U.S. Provisional Application Ser. No. 62/786,166, filed on Dec. 28, 2018, U.S. Provisional Application Ser. No. 62/786,116, filed on Dec. 28, 2018, U.S. Provisional Application Ser. No. 62/786,208, filed on Dec. 28, 2018, and U.S. Provisional Application Ser. No. 62/786,127, filed on Dec. 28, 2018. Each of the aforementioned applications is incorporated by reference herein in its entirety, and each is hereby expressly made a part of this specification

TECHNICAL FIELD

The present development relates generally to medical devices such as analyte sensors, and more particularly, but not by way of limitation, to systems, devices, and methods that mitigate sensor break-in effects in a continuous glucose monitoring system.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information, such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This present application discloses, among other things, systems, devices, and methods for mitigating break-in in an analyte sensor, such as a glucose sensor.

Example 1 is an analyte sensor system, comprising an analyte sensor applicator comprising a needle, an analyte sensor comprising at least a working electrode and a reference electrode. The analyte sensor may be positioned at least partially within a lumen of the needle and a hydrating agent may be positioned within the lumen of the needle to at least partially hydrate the analyte sensor.

In Example 2, the subject matter of Example 1 optionally includes a packaging, wherein the analyte sensor applicator, analyte sensor, and hydrating agent are positioned within the packaging.

In Example 3, the subject matter of Example 2 optionally includes a battery within the packaging, the battery electrically coupled to the analyte sensor to provide a bias potential to the analyte sensor in the packaging.

In Example 4, the subject matter of Example 3 optionally includes wherein the bias potential provided to the analyte sensor by the battery in the packaging is greater than an operating bias potential of the analyte sensor.

In Example 5, the subject matter of any one or more of Examples 1-4 optionally includes wherein the hydrating agent comprises at least one of a foam or a gel.

In Example 6, the subject matter of any one or more of Examples 1-5 optionally includes wherein the analyte sensor applicator comprises a push rod positioned at least partially within a proximal portion of the lumen of the needle to attenuate leakage of the hydrating agent from a proximal end of the lumen.

Example 7 is an analyte sensor system, comprising an analyte sensor comprising a working electrode and a reference electrode. The analyte sensor system also comprises a sensor mounting unit to receive a sensor electronics unit, the sensor mounting unit comprising a first contact to couple to the working electrode of the analyte sensor and a second contact to couple to the reference electrode of the analyte sensor. The analyte sensor system also comprises a battery positioned at the sensor mounting unit, the battery connected to provide a bias voltage across the contact and the second contact.

In Example 8, the subject matter of Example 7 optionally includes wherein the battery is coupled to provide the bias voltage across the first contact and the second contact when the sensor electronics unit is not received by the sensor mounting unit.

In Example 9, the subject matter of any one or more of Examples 7-8 optionally includes an analyte sensor applicator to insert the analyte sensor into a host, wherein the analyte sensor system is configured to electrically couple the working electrode of the analyte sensor to the first contact during insertion of the analyte sensor.

In Example 10, the subject matter of any one or more of Examples 7-9 optionally includes a control circuit configured to perform operations comprising: detecting insertion of the analyte sensor; and responsive to detecting insertion of the analyte sensor, connecting the battery to provide the bias voltage to the analyte sensor.

In Example 11, the subject matter of Example 10 optionally includes wherein detecting insertion of the analyte sensor comprises detecting contact with skin of a host.

In Example 12, the subject matter of any one or more of Examples 10-11 optionally includes wherein detecting insertion of the analyte sensor comprises detecting a change in an electrical characteristic of the first contact and the second contact, the change indicative of a connecting of the analyte sensor to the first contact and the second contact.

In Example 13, the subject matter of any one or more of Examples 7-12 optionally includes an electronics unit comprising a second battery and a regulator, wherein the regulator is configured to regulate a bias potential provided to the analyte sensor by the battery and the second battery.

In Example 14, the subject matter of any one or more of Examples 7-13 optionally includes wherein the battery comprises an anode and a cathode, and wherein the battery is configured to provide the bias voltage when the anode and cathode are in contact with an electrolyte associated with a host.

Example 15 is a method of operating an analyte sensor system comprising a sensor mounting unit and a sensor electronics unit receivable by the sensor mounting unit, the method comprising: detecting insertion of an analyte sensor into tissue of a host; and responsive to the detecting of the insertion, connecting a battery positioned at a sensor mounting unit of the sensor to provide a bias voltage across a working electrode of the analyte sensor and a reference electrode of the sensor.

In Example 16, the subject matter of Example 15 optionally includes detecting insertion of the analyte sensor at least in part by detecting contact with skin of the host.

In Example 17, the subject matter of any one or more of Examples 15-16 optionally includes detecting a change in an electrical characteristic of a first contact of the sensor mounting unit and a second contact of the sensor mounting unit, the change indicative of a connecting of the analyte sensor to the first contact and the second contact.

In Example 18, the subject matter of any one or more of Examples 15-17 optionally includes wherein the connecting of the battery is performed when a sensor electronics unit is not received by the sensor mounting unit.

In Example 19, the subject matter of any one or more of Examples 15-18 optionally includes regulating, by the sensor electronics unit, a bias potential provided to the analyte sensor by the battery and by a second battery of the sensor electronics unit.

Example 20 is an analyte sensor system comprising an analyte sensor and a sensor mounting unit. The analyte sensor may be coupled to the sensor mounting unit. The analyte sensor system also comprises an adhesive pad coupled to the sensor mounting unit to mount to adhere the sensor mounting unit to a skin surface of a host and a first heating element positioned to provide heat to the skin surface of the host when the analyte sensor is inserted.

In Example 21, the subject matter of Example 20 optionally includes wherein the heating element comprises at least a first reactant that reacts in the presence of air to generate heat.

In Example 22, the subject matter of any one or more of Examples 20-21 optionally includes sensor electronics hardware, wherein the sensor electronics hardware is configured to provide power to the first heating element.

In Example 23, the subject matter of Example 22 optionally includes wherein the electronics hardware is configured to perform operations comprising: detecting that the analyte sensor has been inserted into a host; beginning to provide power to the first heating element; and after a first time period, ceasing to provide power to the first heating element.

In Example 24, the subject matter of any one or more of Examples 20-23 optionally includes a sensor electronics unit installable to the sensor mounting unit, wherein the sensor electronics unit is configured to begin providing power to the first heating element after being installed to the sensor mounting unit.

In Example 25, the subject matter of any one or more of Examples 20-24 optionally includes wherein the adhesive pad comprises a permeability-enhancing substance.

Example 26 is a method of applying a bias potential to an analyte sensor. The method may comprise applying a baseline bias potential to the analyte sensor for a first pulse-off period and applying a pulse bias potential to the analyte sensor for a first pulse-on period. The pulse bias potential has a magnitude greater than a magnitude of an operating bias potential of the analyte sensor. The method may also comprise applying the baseline bias potential to the analyte sensor for a second pulse-off period and applying the pulse bias potential to the analyte sensor for a second pulse-on period.

In Example 27, the subject matter of Example 26 optionally includes wherein the first pulse-off period is shorter than the second pulse-off period.

In Example 28, the subject matter of Example 27 optionally includes wherein the first pulse-off is about half of the second pulse-off period.

In Example 29, the subject matter of any one or more of Examples 26-28 optionally includes wherein the first pulse-on period is shorter than the second pulse-on period.

In Example 30, the subject matter of any one or more of Examples 26-29 optionally includes after applying the pulse bias potential to the analyte sensor for the second pulse-off period, applying a substantially constant operational bias potential to the analyte sensor.

In Example 31, the subject matter of any one or more of Examples 26-30 optionally includes wherein the bias pulse potential is between about 5% and about 100% higher than the baseline bias potential.

In Example 32, the subject matter of any one or more of Examples 26-31 optionally includes wherein the bias potential is between about 5% and about 100% higher than the baseline bias potential.

Example 33 is a sensor electronics circuit for driving an analyte sensor. The sensor electronics circuit may be configured to perform operations comprising: applying a baseline bias potential to the analyte sensor for a first pulse-off period and applying a pulse bias potential to the analyte sensor for a first pulse-on period. The pulse bias potential has a magnitude greater than a magnitude of an operating bias potential of the analyte sensor. The operations may also comprise applying the baseline bias potential to the analyte sensor for a second pulse-off period, and applying the pulse bias potential to the analyte sensor for a second pulse-on period.

In Example 34, the subject matter of Example 33 optionally includes wherein the first pulse-off period is shorter than the second pulse-off period.

In Example 35, the subject matter of any one or more of Examples 33-34 optionally includes wherein the first pulse-off is about half of the second pulse-off period.

In Example 36, the subject matter of any one or more of Examples 33-35 optionally includes wherein the first pulse-on period is shorter than the second pulse-on period.

In Example 37, the subject matter of any one or more of Examples 33-36 optionally includes after applying the pulse bias potential to the analyte sensor for the second pulse-off period, applying a substantially constant operational bias potential to the analyte sensor.

In Example 38, the subject matter of any one or more of Examples 33-37 optionally includes wherein the pulse bias potential is between about 5% and about 100% higher than the baseline bias potential.

In Example 39, the subject matter of any one or more of Examples 33-38 optionally includes wherein the pulse bias potential is about 25% higher than the baseline bias potential.

Example 40 is a method for configuring an analyte sensor to generate analyte concentration values during break-in. The method comprises exposing the analyte sensor to a first buffer material having a first analyte concentration and recording first raw sensor signal data from the analyte sensor during a break-in period in the first buffer material. The method also comprises exposing the analyte sensor to a second buffer material having a second analyte concentration different than the first analyte concentration and receiving second raw sensor signal data from the analyte sensor during a break-in period in the second buffer material. The method may also comprise deriving a break-in characteristic for the analyte sensor using the first raw sensor signal data and the second raw sensor signal data, and storing the break-in characteristic in association with the analyte sensor. The break-in characteristic is usable by an analyte sensor system including the analyte sensor to generate analyte concentration values during break-in.

In Example 41, the subject matter of Example 40 optionally includes wherein deriving the break-in characteristic comprises: comparing at least the first raw sensor signal data to a set of break-in curves describing, and selecting a category for the analyte sensor based at least in part on the comparing, wherein the break-in characteristic comprises the category.

In Example 42, the subject matter of any one or more of Examples 40-41 optionally includes determining a first sensitivity for the analyte sensor at a first time during the break-in period using a value of the first raw sensor signal data at the first time and a value of the second raw sensor signal data at the first time; determining a second sensitivity for the analyte sensor at a second time during the break-in period using a value of the first raw sensor signal data at the second time and a value of the second raw sensor signal data at the second time; and generating a break-in intercept for the analyte sensor at the first time, wherein the break-in characteristic comprises the break-in intercept for the analyte sensor at the first time.

In Example 43, the subject matter of Example 42 optionally includes generating a break-in sensitivity for the analyte sensor at the first time, wherein the break-in characteristic comprises the break-in sensitivity.

In Example 44, the subject matter of any one or more of Examples 40-43 optionally includes wherein the break-in characteristic comprises a break-in sensitivity function.

In Example 45, the subject matter of any one or more of Examples 40-44 optionally includes wherein the break-in characteristic comprises a break-in intercept function.

In Example 46, the subject matter of any one or more of Examples 40-45 optionally includes receiving a raw analyte sensor data from the analyte sensor, and generating a first analyte concentration value using the raw analyte sensor data and the break-in characteristic.

Example 47 is a method for configuring an analyte sensor to generate analyte concentration values during break-in, the method comprising: accessing, by a computing device, a plurality of break-in curve sets, wherein a first break-in curve set of the plurality of break-in curve sets comprises first raw sensor signal data describing a first break-of a first analyte sensor at a first host and a second break-in curve set of the plurality of break-in curve set comprises raw sensor signal data describing a second break-in; using, by the computing device, raw sensor signal data from the plurality of break-in curves that describes a first common time to determine a first intercept at the first common time; using, by the computing device, raw sensor signal data from the plurality of break-in curves that describes a second common time to determine a second intercept at a second common time; determining, by the computing device a break-in intercept function using the first intercept and the second intercept; and causing the break-in intercept function to be used by an analyte sensor system to generate a first analyte concentration value during break-in.

In Example 48, the subject matter of Example 47 optionally includes wherein the second break-in is of the first analyte sensor at the first host.

In Example 49, the subject matter of any one or more of Examples 47-48 optionally includes wherein the second break-in is of a second analyte sensor at a second host.

In Example 50, the subject matter of any one or more of Examples 47-49 optionally includes wherein determining the first intercept at the first common time comprises using a first reference analyte concentration describing the first raw sensor signal data and a second reference analyte concentration describing the second raw sensor signal data.

In Example 51, the subject matter of Example 50 optionally includes wherein the first reference analyte concentration is based on a prior analyte sensor used in a prior analyte sensor session of the first host before the first break-in.

In Example 52, the subject matter of any one or more of Examples 50-51 optionally includes wherein the first reference analyte concentration describes an average analyte concentration of a plurality of hosts.

In Example 53, the subject matter of any one or more of Examples 50-52 optionally includes wherein the first reference analyte concentration describes an average analyte concentration of a plurality of hosts over a first time period.

In Example 54, the subject matter of any one or more of Examples 50-53 optionally includes wherein the first reference analyte concentration describes an average concentration of a plurality of hosts having at least one common property.

In Example 55, the subject matter of any one or more of Examples 47-54 optionally includes using the, by the computing device, raw sensor signal data from the plurality of break-in curves that describes a first common time to determine a first sensitivity at the first common time; using, by the computing device, raw sensor signal data from the plurality of break-in curves that describes a second common time to determine a second sensitivity at the second common time; determining, by the computing device a break-in sensitivity function using the first intercept and the second intercept; and causing the break-in sensitivity function to be used by an analyte sensor system to generate a first analyte concentration value during break-in.

In Example 56, the subject matter of any one or more of Examples 47-55 optionally includes matching, by the computing device, raw sensor values from the plurality of break-in curve sets that describe the first common time; and matching, by the computing device, raw sensor values form the plurality of break-in curve sets that describe the second common time.

Example 57 is a method of monitoring analyte concentration data using an analyte sensor. The method comprises receiving, by a computing device, a first analyte concentration value determined using the analyte sensor; determining that the first analyte concentration value is based on raw sensor signal data captured during break-in; and responsive to determining that the first analyte concentration value is based on raw sensor signal data captured during break-in, displaying the first analyte concentration value at a user interface in association with a first confidence indicator, the first confidence indicator indicating a first level of confidence in the first analyte concentration value.

In Example 58, the subject matter of Example 57 optionally includes receiving a second analyte concentration value determined using the analyte sensor; determining that the second analyte concentration value is based on raw sensor signal data captured after break-in; and responsive to determining that the first analyte concentration value is based on raw sensor signal data captured during break-in, displaying the first analyte concentration value at a user interface in association with a second confidence indicator, the second confidence indicator indicating a first level of confidence in the first analyte concentration value higher than the first level.

In Example 59, the subject matter of Example 58 optionally includes wherein displaying the first analyte concentration value in association with the first confidence indicator comprises displaying the first analyte concentration value in a first font, and wherein displaying the second analyte concentration value in association with the second confidence indicator comprises displaying the second analyte concentration value in a second font different than the first font.

In Example 60, the subject matter of any one or more of Examples 58-59 optionally includes wherein the first confidence indicator comprises a first shape having a first area, and wherein the second confidence indicator comprises a second shape having a second area less than the first area.

In Example 61, the subject matter of any one or more of Examples 58-60 optionally includes wherein displaying the first analyte concentration value in association with the second confidence indicator comprises displaying the second analyte concentration value in association with an analyte trend shape, and wherein displaying the first analyte concentration value in association with the first confidence indicator comprises omitting the analyte trend shape.

In Example 62, the subject matter of any one or more of Examples 57-61 optionally includes wherein the first confidence indicator comprises a bounding curve positioned adjacent an analyte concentration curve and wherein a proximity of the bounding curve to the analyte concentration curve indicates the first level of confidence.

In Example 63, the subject matter of any one or more of Examples 57-62 optionally includes wherein the first confidence indicator comprises an error bar positioned on an analyte concentration curve, wherein a size of the error bar indicates the first level of confidence.

Example 64 is a computing device for monitoring analyte concentration data using an analyte sensor. The computing device comprises a processor and a machine-readable medium comprising instructions thereon that, when executed by the processor, cause the processor to perform operations. The operations comprise receiving a first analyte concentration value determined using the analyte sensor; determining that the first analyte concentration value is based on raw sensor signal data captured during break-in; and responsive to determining that the first analyte concentration value is based on raw sensor signal data captured during break-in, displaying the first analyte concentration value at a user interface in association with a first confidence indicator, the first confidence indicator indicating a first level of confidence in the first analyte concentration value.

In Example 65, the subject matter of Example 64 optionally includes wherein the operations further comprise: receiving a second analyte concentration value determined using the analyte sensor; determining that the second analyte concentration value is based on raw sensor signal data captured after break-in; and responsive to determining that the first analyte concentration value is based on raw sensor signal data captured during break-in, displaying the first analyte concentration value at a user interface in association with a second confidence indicator, the second confidence indicator indicating a first level of confidence in the first analyte concentration value higher than the first level.

In Example 66, the subject matter of Example 65 optionally includes wherein displaying the first analyte concentration value in association with the first confidence indicator comprises displaying the first analyte concentration value in a first font, and wherein displaying the second analyte concentration value in association with the second confidence indicator comprises displaying the second analyte concentration value in a second font different than the first font.

In Example 67, the subject matter of any one or more of Examples 65-66 optionally includes wherein the first confidence indicator comprises a first shape having a first area, and wherein the second confidence indicator comprises a second shape having a second area less than the first area.

In Example 68, the subject matter of any one or more of Examples 65-67 optionally includes wherein displaying the first analyte concentration value in association with the second confidence indicator comprises displaying the second analyte concentration value in association with an analyte trend shape, and wherein displaying the first analyte concentration value in association with the first confidence indicator comprises omitting the analyte trend shape.

In Example 69, the subject matter of any one or more of Examples 64-68 optionally includes wherein the first confidence indicator comprises a bounding curve positioned adjacent an analyte concentration curve and wherein a proximity of the bounding curve to the analyte concentration curve indicates the first level of confidence.

In Example 70, the subject matter of any one or more of Examples 64-69 optionally includes wherein the first confidence indicator comprises an error bar positioned on an analyte concentration curve, wherein a size of the error bar indicates the first level of confidence.

Example 71 is a method for configuring an analyte sensor to generate analyte concentration values during break-in, the method comprising: detecting insertion of the analyte sensor under skin of a host; upon detecting the insertion, collecting sensor insertion data for an insertion time period; determining at least one break-in model parameter based on the insertion data; and generating at least one analyte value based on a raw sensor signal received from the analyte sensor and the at least one break-in model parameter.

In Example 72, the subject matter of Example 71 optionally includes receiving non-enzyme sensor data describing a break-in of at least one non-enzyme sensor; and using the non-enzyme sensor data to generate an initial break-in model parameter, wherein determining the at least one break-in model parameter comprises modifying the initial break-in model parameter.

In Example 73, the subject matter of Example 72 optionally includes wherein the insertion time period is prior to a convergence time between a non-enzyme break-in model generated using the non-enzyme sensor data and the analyte sensor.

In Example 74, the subject matter of any one or more of Examples 72-73 optionally includes wherein the generating of the initial break-in model parameter is based on at least a portion of the non-enzyme sensor data describing the at least one non-enzyme sensor within about two hours of a beginning of break-in.

In Example 75, the subject matter of any one or more of Examples 71-74 optionally includes wherein the at least one break-in model parameter consists of at least one break-in intercept model parameter.

In Example 76, the subject matter of any one or more of Examples 71-75 optionally includes wherein the collecting of the sensor insertion data comprises sampling a raw sensor signal of the analyte sensor.

In Example 77, the subject matter of Example 76 optionally includes Hz.

In Example 78, the subject matter of any one or more of Examples 71-77 optionally includes wherein the at least one break-in model comprises at least one membrane break-in model parameter and at least one electrochemical break-in model parameter.

An example (e.g., "Example 9") of subject matter (e.g., a system or apparatus) may optionally combine any portion or combination of any portion of any one or more of Examples 1-8 to include "means for" performing any portion of any one or more of the functions or methods of Examples 1-8.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments described in the present document.

FIG. 9 is an exploded side view showing one example of a sensor applicator.

FIG. 18 is a diagram showing one example of a pulsed overpotential bias that can be provided to analyte sensor in some examples to accelerate break-in.

FIG. 23 is a flowchart showing one example of a process flow that can be executed at an analyte sensor system to generate analyte concentration values during break-in.

FIGS. 25-28 show example UI screens showing example confidence indicators associated with analyte concentration values.

FIG. 31 is a diagram including two example plots indicating errors of example analyte sensors during break-in.

DETAILED DESCRIPTION

Figure 1:
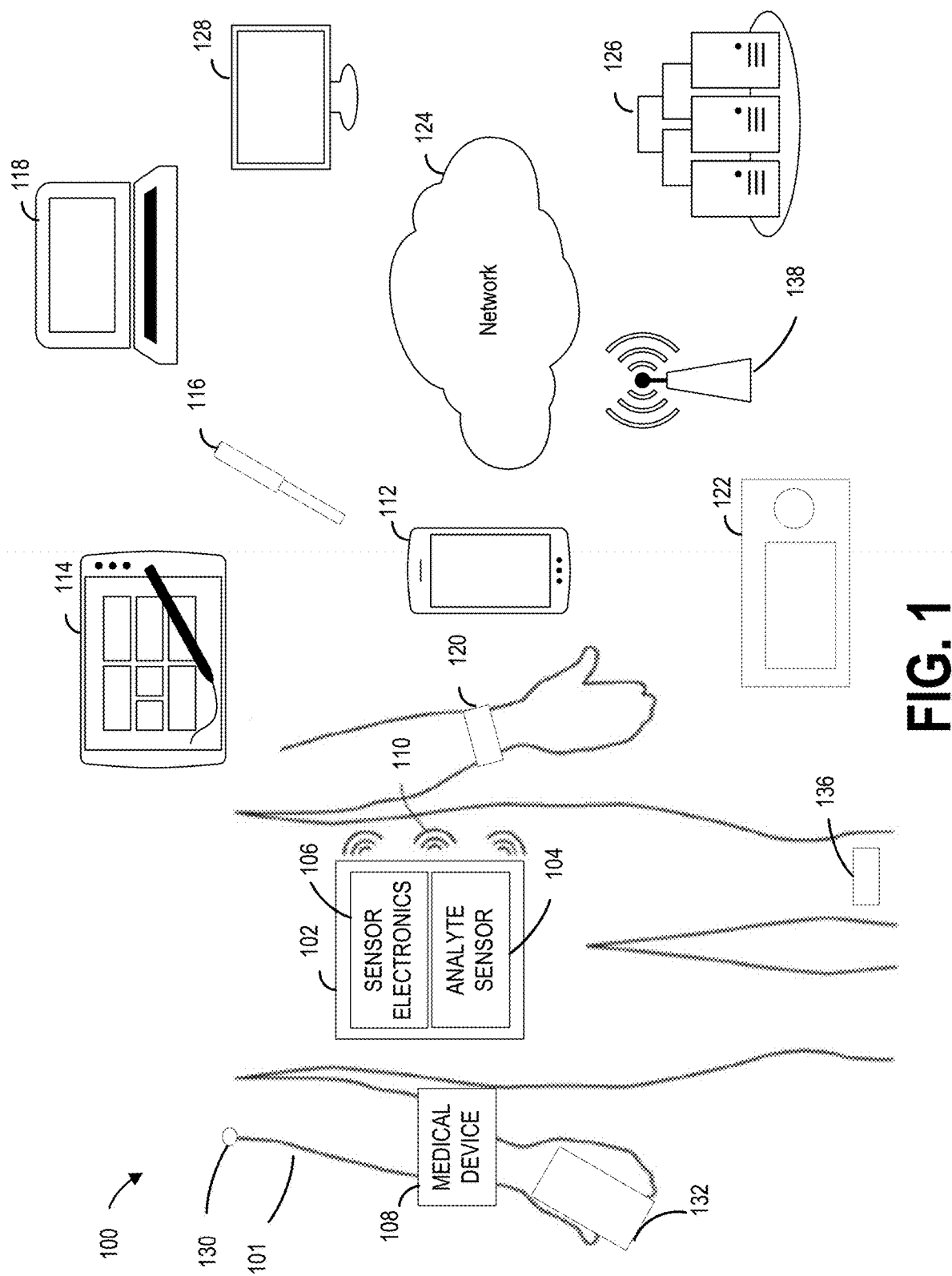
FIG. 1 is a diagram showing one example of an environment including an analyte sensor system.

Various examples described herein are directed to analyte sensors and methods for using analyte sensors. An analyte sensor is placed in contact with bodily fluid of a host to measure a concentration of an analyte, such as glucose, in the bodily fluid. In some examples, the analyte sensor is inserted under the skin of the host and placed in contact with interstitial fluid below the skin to measure the concentration of the analyte in the interstitial fluid.

When the analyte sensor is exposed to analyte, an electrochemical reaction between the analyte sensor and the analyte causes the analyte sensor to generate a raw sensor signal indicating the analyte concentration. In some examples, the analyte sensor includes a working electrode and a reference electrode. Sensor electronics apply a bias potential between the working electrode and the reference electrode. The applied bias promotes the electrochemical reaction between the analyte and the analyte sensor, resulting in a current between the working electrode and the reference electrode. The current makes up all or part of the raw sensor signal.

For much of the useful life of the analyte sensor, the relationship between the raw sensor signal and the analyte concentration at the analyte sensor is linear, or approximately linear. The sensor electronics applies a slope, referred to as a sensor sensitivity, and an offset to the raw sensor signal to generate a corresponding analyte concentration. When an analyte sensor session begins, however, the linear relationship between the raw sensor signal and the analyte concentration does not hold. During a break-in or sensor break-in, the response of the analyte sensor to the analyte is nonlinear. As used herein, the term "break-in" or "sensor break-in" refers without limitation to a time required for the analyte sensor's raw sensor signal to provide a substantially linear response to the analyte concentration (e.g. glucose level).

Break-in can be caused by one or more factors. For example, when a bias potential is first applied to the analyte sensor, it promotes an electrochemical reaction with the analyte but may also promote other non-analyte electrochemical reactions which also generate current at the analyte sensor, such as oxidation reactions at the electrode surfaces. The effects of non-analyte electrochemical reactions may decay with time but can initially make a substantial contribution to the raw sensor signal. The non-analyte electrochemical reactions contribute to electrochemical break-in. The term "electrochemical break-in," as used herein refers without limitation to a time after analyte sensor insertion in vitro and/or in vivo, at which the raw sensor signal from the analyte sensor settles to a substantially linear response to the analyte concentration after the application of the bias potential to the analyte sensor.

An analyte sensor membrane can also contribute to break-in. The membrane is also sometimes referred to as a membrane system. The membrane or membrane system, described in more detail herein, can perform functions in the analyte sensor including, for example, regulating the amount of analyte that reacts with the analyte sensor, providing an enzyme that reacts with the analyte, etc. In some examples, the analyte sensor is dry immediately before insertion into a host. When inserted in vitro or in vivo, the membrane is exposed to fluid (e.g., interstitial fluid) and begins to hydrate. As the membrane hydrates, its effects on the electrochemical reactions at the analyte sensor changes, causing the raw sensor signal to behave differently. In some examples, the effects of the membrane become substantially constant when the membrane is fully hydrated. The term "membrane break-in," as used herein refers without limitation to a time taken for the membrane to equilibrate to its environment (e.g., the physiological environment in vivo).

Because the response of the analyte sensor to analyte is non-linear during break-in, it can be difficult to obtain usable measurements of analyte concentration during this time. The various examples described herein are directed to apparatuses, systems, and/or methods for shortening break-in and/or compensating the raw sensor signal during break-in to generate analyte concentration values.

Some examples described herein are directed to apparatuses, systems, and/or methods that mitigate analyte sensor break-in by causing at least some of the break-in to occur before the analyte sensor is inserted in vivo. Because at least some of the break-in occurs prior to insertion of the sensor, the analyte sensor generates usable analyte concentration values more quickly after insertion.

In some examples, the analyte sensor is pre-hydrated. For example, the analyte sensor can be packaged in contact with a hydrating agent. The hydrating agent completely or partially hydrates the membrane of the analyte sensor while the analyte sensor is in the packaging. In this way, when the analyte sensor is inserted, membrane break-in can be reduced or, in some examples eliminated. In various examples, the hydrating agent is included at least partially within a lumen of a needle used for inserting the analyte sensor. The analyte sensor is packaged with an analyte sensor applicator that includes the needle. During packaging, all or a portion of the analyte sensor is positioned within the lumen of the hypodermic needle in contact with the hydrating agent. In this way, the hydrating agent partially or completely hydrates the analyte sensor membrane while the analyte sensor is packaged. This may reduce or eliminate membrane break-in when the analyte sensor is removed from its packaging and inserted under the host's skin.

In another example, the analyte sensor system also comprises a battery that applies a bias potential to the analyte sensor while it is in packaging. This may cause at least some of the electrochemical break-in for the analyte sensor to occur in the packaging prior to insertion. As a result, electrochemical break-in for the analyte sensor can be reduced.

Some analyte sensors include a sensor mounting unit and a separate sensor electronics unit. The sensor mounting unit is coupled to the analyte sensor. After the analyte sensor is inserted, the sensor mounting unit rests on the surface of the host's skin. The sensor electronics unit, which provides the bias potential in use, is then installed on the mounting unit. In some examples, the sensor electronics unit is snap-fit or press-fit into the sensor mounting unit.

After the sensor electronics unit is installed, it begins to provide the bias potential to the analyte sensor. Sometimes, however, there is a delay between the time that the analyte sensor is inserted into the host's skin and the time that the sensor electronics unit is installed and begins providing the bias potential. This can affect the electrochemical break-in of the sensor. For example, when there is a delay between sensor insertion and application of the bias potential, various physiological and/or chemical interactions can occur at the analyte sensor. When the bias potential is applied, the analyte sensor may behave differently than if the bias potential had been applied closer in time to the sensor insertion. A delay between sensor insertion and the application of the bias potential, in some examples, can also cause electrochemical break in and membrane break-in to be offset. This also changes the overall break-in of the analyte sensor. Modifications to break-in resulting from a delay between sensor insertion and the application of the bias potential in some examples make break-in take longer and may also increase the difficulty of compensating the raw sensor signal during break-in.

In some examples, the sensor mounting unit includes a battery that is configured begin providing a bias potential to the analyte sensor upon insertion. In this way, electrochemical break-in may begin at or near the time of sensor insertion, even if the sensor electronics unit is not installed right away. In some examples, the battery is a self-powered battery. A self-powered battery can include a cathode and an anode. When the analyte sensor is inserted into the host's skin, the host's tissue can act as an electrolyte completing the battery to generate the bias potential at the analyte sensor.

In some examples, an analyte sensor system is configured to accelerate break-in by applying a treatment to the host's skin at or near the insertion site where the analyte sensor is inserted. For example, the analyte sensor system can be configured to apply heat to the host's skin. Warming the skin can increase the speed of the electrochemical break-in, thereby shorten its duration. The analyte sensor system can warm the skin, for example, using a heating element powered by a battery associated with the sensor electronics. In another example, the analyte sensor system can include a chemical reactant that reacts in the presence of air to generate heat. In some examples, the analyte sensor system is configured to apply a treatment to the host's skin that includes applying a permeability enhancing substance to the host's skin. The permeability-enhancing substance may increase the flow of fluids to and from the insertion site, which can accelerate electrochemical and/or membrane break-in.

In some examples, break-in can be accelerated by applying a pulsed overpotential bias during break-in. For example, instead of applying a constant bias potential during break-in, sensor electronics of an analyte sensor system can be configured to provide a series of voltage pulses, where the pulses are in excess of the operating bias potential. The overpotential pulses may provide a higher level of electro-chemical energy during break-in, thereby accelerating the electrochemical reactions and shortening break-in.

Various examples described herein are directed to obtaining usable analyte concentration values from the analyte sensor during break-in by modeling the response of the analyte sensor to the analyte during break-in and applying the generated model or models.

In some examples, a break-in model is generated using analyte sensor characteristic data gathered in vitro during the manufacture of the analyte sensor. The analyte sensor can be exposed to various buffer materials having different known concentrations of the analyte. The raw sensor signals from the analyte sensor are used to derive a break-in characteristic for the analyte sensor. The break-in characteristic can be stored in association with the analyte sensor. For example, the break-in characteristic, and/or an indication thereof, can be printed on packaging for the analyte sensor. When the analyte sensor is inserted into a host, the break-in characteristic is usable to compensate the raw sensor signal during break-in.

In some examples, previous patient data is used to generate a break-in characteristic for an analyte sensor. For example, interhost break-in data from break-ins over a large number of hosts can be aggregated, for example, at server, cloud storage location, or other suitable location. The interhost break-in data can be used to generate one or more break-in characteristics.

In addition to or instead of interhost break-in data, intra-host break-in data can be used to generate one or more host-specific break-in characteristics. For example, break-in can be different for different hosts. This can be for various reasons. For example, different physiological factors in different hosts can cause differences in analyte sensor break-in. Also, for example, different hosts can insert the sensor and install the sensor electronics unit differently. These differences can affect break-in for analyte sensors installed at the host. Accordingly, intra-host break-in data may be used to generate one or more break-in characteristics.

In some examples, analyte concentration data generated during break-in may be less certain than analyte concentration data generated after break-in. Despite this, in some examples, it is more desirable to advise the host of a less-certain analyte concentration value during break-in than it is to make the host wait through the break-in period before receiving any analyte concentration values.

Various examples described herein are directed to user interfaces (UIs) and/or UI elements that can be served to a host during break-in to indicate a level of confidence associated with an analyte concentration value. For example, a computing device can detect that an analyte concentration value was based on raw sensor signal data from break-in. For example, the analyte concentration value may have been generated using a break-in characteristic of the analyte sensor, as described herein. Upon detecting that the analyte concentration value was based on raw sensor signal data from break-in, the computing device displays the analyte concentration value in association with a confidence indicator indicating a lower level of confidence in the analyte concentration value than in post-break-in values.

FIG. 1 is a diagram showing one example of an environment 100 including an analyte sensor system 102. The analyte sensor system 102 is coupled to a host 101, which may be a human patient. In some examples, the host is subject to a temporary or permanent diabetes condition or other health condition that makes analyte monitoring useful.

The analyte sensor system 102 includes an analyte sensor 104. In some examples, the analyte sensor 104 is or includes a glucose sensor configured to measure a glucose concentration in the host 101. The analyte sensor 104 can be exposed to analyte at the host 101 in any suitable way. In some examples, the analyte sensor 104 is fully implantable under the skin of the host 101. In other examples, the analyte sensor 104 is wearable on the body of the host 101 (e.g., on the body but not under the skin). Also, in some examples, the analyte sensor 104 is a transcutaneous device (e.g., with a sensor residing at least partially under or in the skin of a host). It should be understood that the devices and methods described herein can be applied to any device capable of detecting a concentration of an analyte, such as glucose, and providing an output signal that represents the concentration of the analyte.

In the example of FIG. 1, the analyte sensor system 102 also includes sensor electronics 106. In some examples, the sensor electronics 106 and analyte sensor 104 are provided in a single integrated package. In other examples, the analyte sensor 104 and sensor electronics 106 are provided as separate components or modules. For example, the analyte sensor system 102 may include a disposable (e.g., single-use) sensor mounting unit (FIG. 3) that may include the analyte sensor 104, a component for attaching the sensor 104 to a host (e.g., an adhesive pad), and/or a mounting structure configured to receive a sensor electronics unit including some or all of the sensor electronics 106 shown in FIG. 2. The sensor electronics unit may be reusable.

The analyte sensor 104 may use any known method, including invasive, minimally-invasive, or non-invasive sensing techniques (e.g., optically excited fluorescence, microneedle, transdermal monitoring of glucose), to provide a raw sensor signal indicative of the concentration of the analyte in the host 101. The raw sensor signal may be converted into calibrated and/or filtered analyte concentration data used to provide a useful value of the analyte concentration (e.g., estimated blood glucose concentration level) to a user, such as the host or a caretaker (e.g., a parent, a relative, a guardian, a teacher, a doctor, a nurse, or any other individual that has an interest in the wellbeing of the host 101).

In some examples, the analyte sensor 104 is or includes a continuous glucose sensor. A continuous glucose sensor can be or include a subcutaneous, transdermal (e.g., transcutaneous), and/or intravascular device. In some embodiments, such a sensor or device may recurrently (e.g., periodically or intermittently) analyze sensor data. The glucose sensor may use any method of glucose measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™, (e.g., the DexCom G5™ sensor or Dexcom G6™ sensor or any variation thereof), from Abbott™ (e.g., the Libre™ sensor), or from Medtronic™ (e.g., the Enlite™ sensor).

In some examples, analyte sensor 104 includes an implantable glucose sensor, such as described with reference to U.S. Pat. No. 6,001,067 and U.S. Patent Publication No. US-2005-0027463-A1, which are incorporated by reference. In some examples, analyte sensor 104 includes a transcutaneous glucose sensor, such as described with reference to U.S. Patent Publication No. US-2006-0020187-A1, which is incorporated by reference. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007, all of which are incorporated by reference. In some examples, the continuous glucose sensor may include a transcutaneous sensor such as described in U.S. Pat. No. 6,565,509 to Say et al., which is incorporated by reference. In some examples, analyte sensor 104 may include a continuous glucose sensor that includes a subcutaneous sensor such as described with reference to U.S. Pat. No. 6,579,690 to Bonnecaze et al. or U.S. Pat. No. 6,484,046 to Say et al., which are incorporated by reference. In some examples, the continuous glucose sensor may include a refillable subcutaneous sensor such as described with reference to U.S. Pat. No. 6,512,939 to Colvin et al., which is incorporated by reference. The continuous glucose sensor may include an intravascular sensor such as described with reference to U.S. Pat. No. 6,477,395 to Schulman et al., which is incorporated by reference. The continuous glucose sensor may include an intravascular sensor such as described with reference to U.S. Pat. No. 6,424,847 to Mastrototaro et al., which is incorporated by reference.

The environment 100 may also include a second medical device 108. The second medical device 108 may be or include a drug delivery device such as an insulin pump or an insulin pen. In some examples, the medical device 108 includes one or more sensors, such as another analyte sensor, a heart rate sensor, a respiration sensor, a motion sensor (e.g. accelerometer), posture sensor (e.g. 3-axis accelerometer), acoustic sensor (e.g. to capture ambient sound or sounds inside the body). The medical device 108 may be wearable, e.g., on a watch, glasses, contact lens, patch, wristband, ankle band, or other wearable item, or may be incorporated into a handheld device (e.g., a smartphone). In some examples, the medical device 108 includes a multi-sensor patch that may, for example, detect one or more of an analyte level (e.g., glucose, lactate, insulin or other substance), heart rate, respiration (e.g., using impedance), activity (e.g., using an accelerometer), posture (e.g., using an accelerometer), galvanic skin response, tissue fluid levels (e.g., using impedance or pressure).

In some examples, the analyte sensor system 102 and the second medical device 108 communicate with one another. Communication between the analyte sensor system 102 and medical device 108 may occur over any suitable wired connection and/or via a wireless communication signal 110. For example, the analyte sensor system 102 may be configured to communicate using via radio frequency (e.g., Bluetooth, Medical Implant Communication System (MICS), Wi-Fi, near field communication (NFC), radio frequency identification (RFID), Zigbee, Z-Wave or other communication protocols), optically (e.g., infrared), sonically (e.g., ultrasonic), or a cellular protocol (e.g., Code Division Multiple Access (CDMA) or Global System for Mobiles (GSM)), or via a wired connection (e.g., serial, parallel, etc.).

In some examples, the environment 100 also includes a wearable sensor 130. The wearable sensor 130 can include a sensor circuit (e.g., a sensor circuit configured to detect a glucose concentration or other analyte concentration) and a communication circuit, which may, for example, be a NFC circuit. In some examples, information from the wearable sensor 130 may be retrieved from the wearable sensor 130 using a user computing device 132, such as a smart phone, that is configured to communicate with the wearable sensor 130 via the wearable sensor's communication circuit, for example, when the user device 132 is placed near the wearable sensor 130. For example, swiping the user device 132 over the sensor 130 may retrieve sensor data from the wearable sensor 130 using NFC or other suitable wireless communication. The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above,) communication. The additional wearable sensor 130 may be any of the examples described above with respect to medical device 108. The analyte sensor system 102, medical device 108, and additional sensor 130 on the host 101 are provided for illustration and description and are not necessarily drawn to scale.

The environment 100 may also include one or more computing devices, such as a hand-held smart device (e.g., smart device) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

In some examples, the environment 100 includes a server system 126. The server system 126 can include one or more computing devices, such as one or more server computing devices. In some examples, the server system 126 is used to collect analyte data from the analyte sensor system 102 and/or analyte or other data from the plurality of other devices, and to perform analytics on collected data, generate or apply universal or individualized models for glucose levels, and communicate such analytics, models, or information based thereon back to one or more of the devices in the environment 100. In some examples, the server system 126 gathers inter-host and/or intra-host break-in data to generate one or more break-in characteristics, as described herein.

The environment 100 may also include a wireless access point (WAP) 138 used to communicatively couple one or more of analyte sensor system 102, network 124, server system 126, medical device 108 or any of the peripheral devices described above. For example, WAP 138 may provide Wi-Fi and/or cellular connectivity within environment 100. Other communication protocols, such as NFC or Bluetooth, may also be used among devices of the environment 100.

Figure 2:
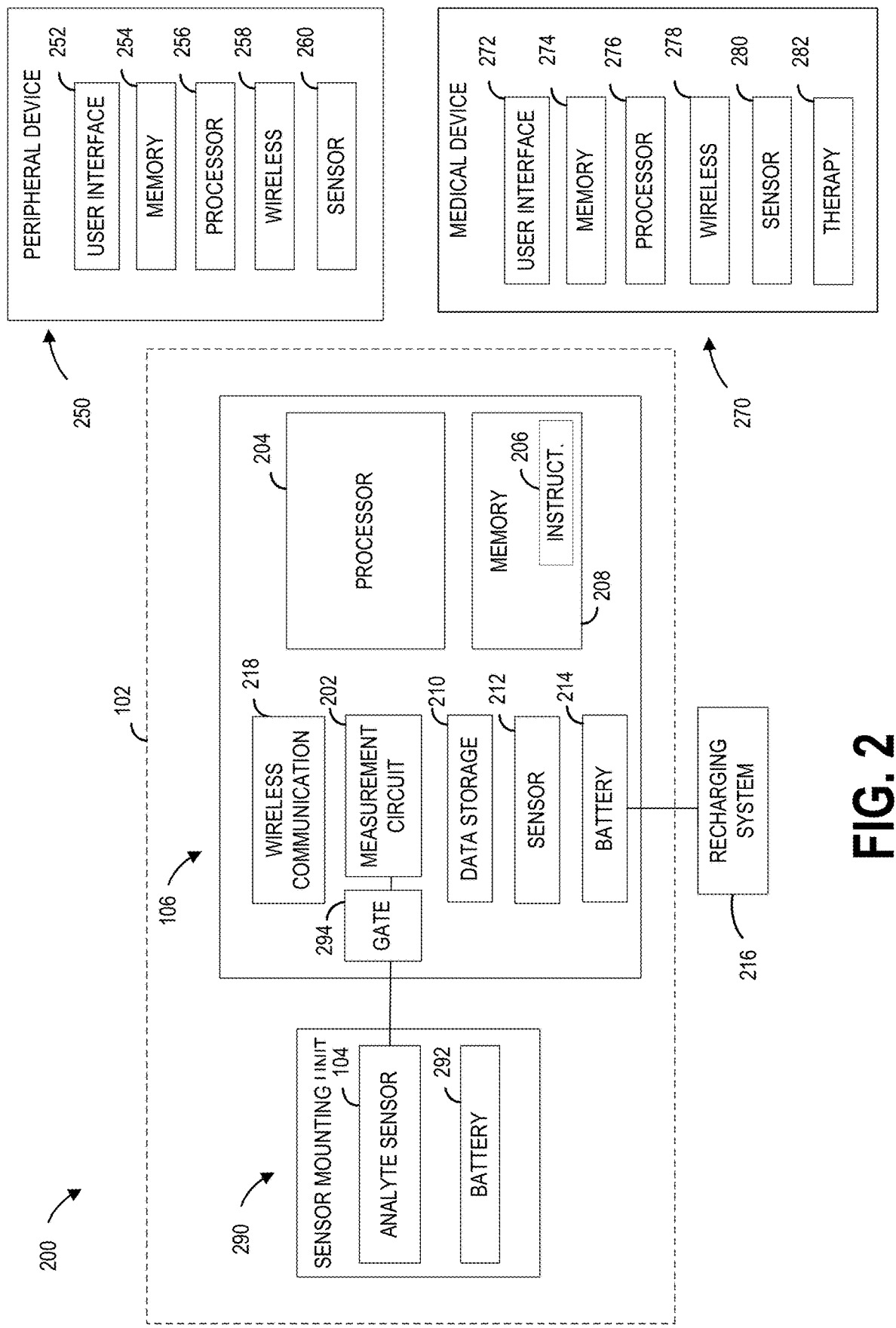
FIG. 2 is a diagram showing one example of a medical device system including the analyte sensor system of FIG. 1.

FIG. 2 is a diagram showing one example of a medical device system 200 including the analyte sensor system 102 of FIG. 1. In the example of FIG. 2, the analyte sensor system 102 includes sensor electronics 106 and a sensor mounting unit 290. While a specific example of division of components between the sensor mounting unit 290 and sensor electronics 106 is shown, it is understood that some examples may include additional components in the sensor mounting unit 290 or in the sensor electronics 106, and that some of the components (e.g., a battery or supercapacitor) that are shown in the sensor electronics 106 may be alternatively or additionally (e.g., redundantly) provided in the sensor mounting unit 290.

In the example shown in FIG. 2, the sensor mounting unit 290 includes the analyte sensor 104 and a battery 292. In some examples, the sensor mounting unit 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as raw sensor signals, and generate corresponding analyte concentration values. The sensor electronics 106 may, for example, include electronic circuitry associated with measuring, processing, storing, or communicating continuous analyte sensor data, including prospective algorithms associated with processing and calibration of the raw sensor signal. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

In the example of FIG. 2, the sensor electronics 106 include a measurement circuit 202 (e.g., potentiostat) coupled to the analyte sensor 104 and configured to recurrently obtain analyte sensor readings using the analyte sensor 104. For example, the measurement circuit 202 may continuously or recurrently measure a raw sensor signal indicating a current flow at the analyte sensor 104 between a working electrode and a reference electrode. The sensor electronics 106 may include a gate circuit 294, which may be used to gate the connection between the measurement circuit 202 and the analyte sensor 104. For example, the analyte sensor 104 may accumulate charge over an accumulation period. After the accumulation period, the gate circuit 294 is opened so that the measurement circuit 202 can measure the accumulated charge. Gating the analyte sensor 104 may improve the performance of the sensor system 102 by creating a larger signal to noise or interference ratio (e.g., because charge accumulates from an analyte reaction, but sources of interference, such as the presence of acetaminophen near a glucose sensor, do not accumulate, or accumulate less than the charge from the analyte reaction).

The sensor electronics 106 may also include a processor 204. The processor 204 is configured to retrieve instructions 206 from memory 208 and execute the instructions 206 to control various operations in the analyte sensor system 102. For example, the processor 204 may be programmed to control application of bias potentials to the analyte sensor 104 via a potentiostat at the measurement circuit 202, interpret raw sensor signals from the analyte sensor 104, and/or compensate for environmental factors.

The processor 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor 204. The sensor 212 may be a temperature sensor, accelerometer, or another suitable sensor. The sensor electronics 106 may also include a power source such as a capacitor or battery 214, which may be integrated into the sensor electronics 106, or may be removable, or part of a separate electronics unit. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics unit (as shown), or in the sensor mounting unit 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the processor 204, so that the supercapacitor is prepared for delivery of energy during a subsequent high-load period. In some examples, the supercapacitor may be configured in parallel with the battery 214. A device may be configured to preferentially draw energy from the supercapacitor, as opposed to the battery 214. In some examples, a supercapacitor may be configured to receive energy from a rechargeable battery for short-term storage and transfer energy to the rechargeable battery for long-term storage.

The supercapacitor may extend an operational life of the battery 214 by reducing the strain on the battery 214 during the high-load period. In some examples, a supercapacitor removes at least 10% of the strain off the battery during high-load events. In some examples, a supercapacitor removes at least 20% of the strain off the battery during high-load events. In some examples, a supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor 204 and may be configured to wirelessly communicate with one or more peripheral devices or other medical devices, such as an insulin pump or smart insulin pen.

In the example of FIG. 2, the medical device system 200 also includes an optional peripheral device 250. The peripheral device 250 may be any suitable user computing device such as, for example, a wearable device (e.g., activity monitor), such as a wearable device 120. In other examples, the peripheral device 250 may be a hand-held smart device (e.g., smartphone or other device such as a proprietary handheld device available from Dexcom), a tablet 114, a smart pen 116, or special-purpose computer 118 shown in FIG. 1.

The peripheral device 250 may include a UI 252, a memory circuit 254, a processor 256, a wireless communication circuit 258, a sensor 260, or any combination thereof. The peripheral device 250 may not necessarily include all the components shown in FIG. 2. The peripheral device 250 may also include a power source, such as a battery.

The UI 252 may, for example, be provided using any suitable input/output device or devices of the peripheral device 250 such as, for example, a touch-screen interface, a microphone (e.g., to receive voice commands), or a speaker, a vibration circuit, or any combination thereof. The UI 252 may receive information from the host or another user (e.g., instructions, glucose values). The UI 252 may also deliver information to the host or other user, for example, by displaying UI elements at the UI 252. For example, UI elements can indicate glucose or other analyte concentration values, glucose or other analyte trends, glucose or other analyte alerts, etc. Trends can be indicated by UI elements such as arrows, graphs, charts, etc.

The processor 256 may be configured to present information to a user, or receive input from a user, via the UI 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as any of the wireless protocols described herein. The sensor 260 may, for example, include an accelerometer, a temperature sensor, a location sensor, biometric sensor, or blood glucose sensor, blood pressure sensor, heart rate sensor, respiration sensor, or other physiologic sensor.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the UI 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

In the example of FIG. 2, the medical device system 200 includes an optional medical device 270. For example, the medical device 270 may be used in addition to or instead of the peripheral device 250. The medical device 270 may be or include any suitable type of medical or other computing device including, for example, the medical device 108, peripheral medical device 122, wearable device 120, wearable sensor 130, or wearable sensor 136 shown in FIG. 1. The medical device 270 may include a UI 272, a memory circuit 274, a processor 276, a wireless communication circuit 278, a sensor 280, a therapy circuit 282, or any combination thereof.

Similar to the UI 252, the UI 272 may be provided using any suitable input/output device or devices of the medical device 270 such as, for example, a touch-screen interface, a microphone, or a speaker, a vibration circuit, or any combination thereof. The UI 272 may receive information from the host or another user (e.g., glucose values, alert preferences, calibration coding). The UI 272 may also deliver information to the host or other user, for example, by displaying UI elements at the UI 252. For example, UI elements can indicate glucose or other analyte concentration values, glucose or other analyte trends, glucose or other analyte alerts, etc. Trends can be indicated by UI elements such as arrows, graphs, charts, etc.

The processor 276 may be configured to present information to a user, or receive input from a user, via the UI 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as any of the wireless protocols described herein.

The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof.

In examples where medical device 270 is or includes an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the medical device system 200 includes two or more peripheral devices and/or medical devices that each receive information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, referring now to the example of FIG. 1, a plurality of different peripheral devices may be in direct wireless communication with sensor electronics 106 (e.g., such as an on-skin sensor electronics 106 that are physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system 102 and relay (i.e., share) information to other devices directly or through a server system (e.g., a network-connected data center) 126.

Figure 3:
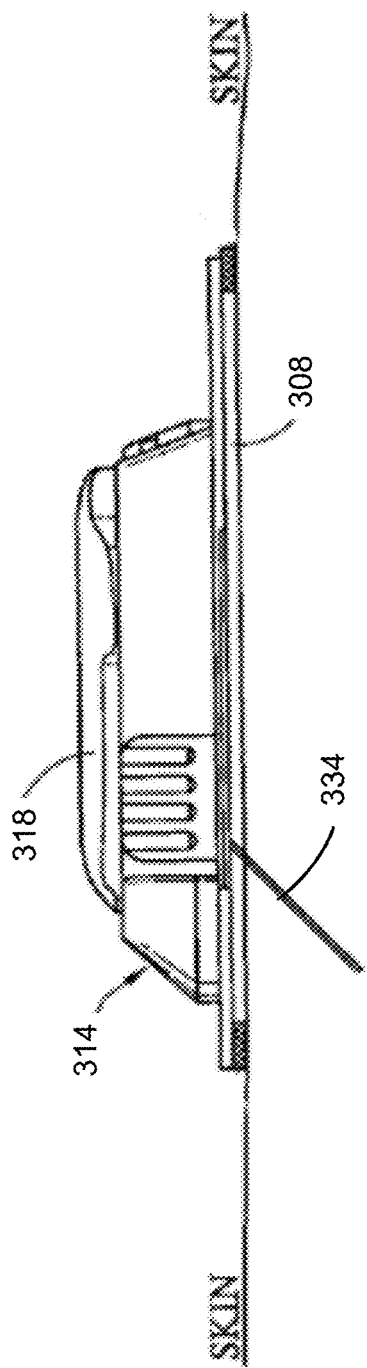
FIG. 3 is an illustration of an example analyte sensor.

FIG. 3 is a side view of an example analyte sensor 334 that may be implanted into a host. A mounting unit 314 may be adhered to the host's skin using an adhesive pad 308. The adhesive pad 308 may be formed from an extensible material, which may be removably attached to the skin using an adhesive. Electronics unit 318 may mechanically couple to the mounting unit 314. In some examples, the electronics unit 318 and mounting unit 314 are arranged in a manner similar to the sensor electronics 106 and sensor mounting unit 290 shown in FIGS. 1 and 2.

Figure 4:
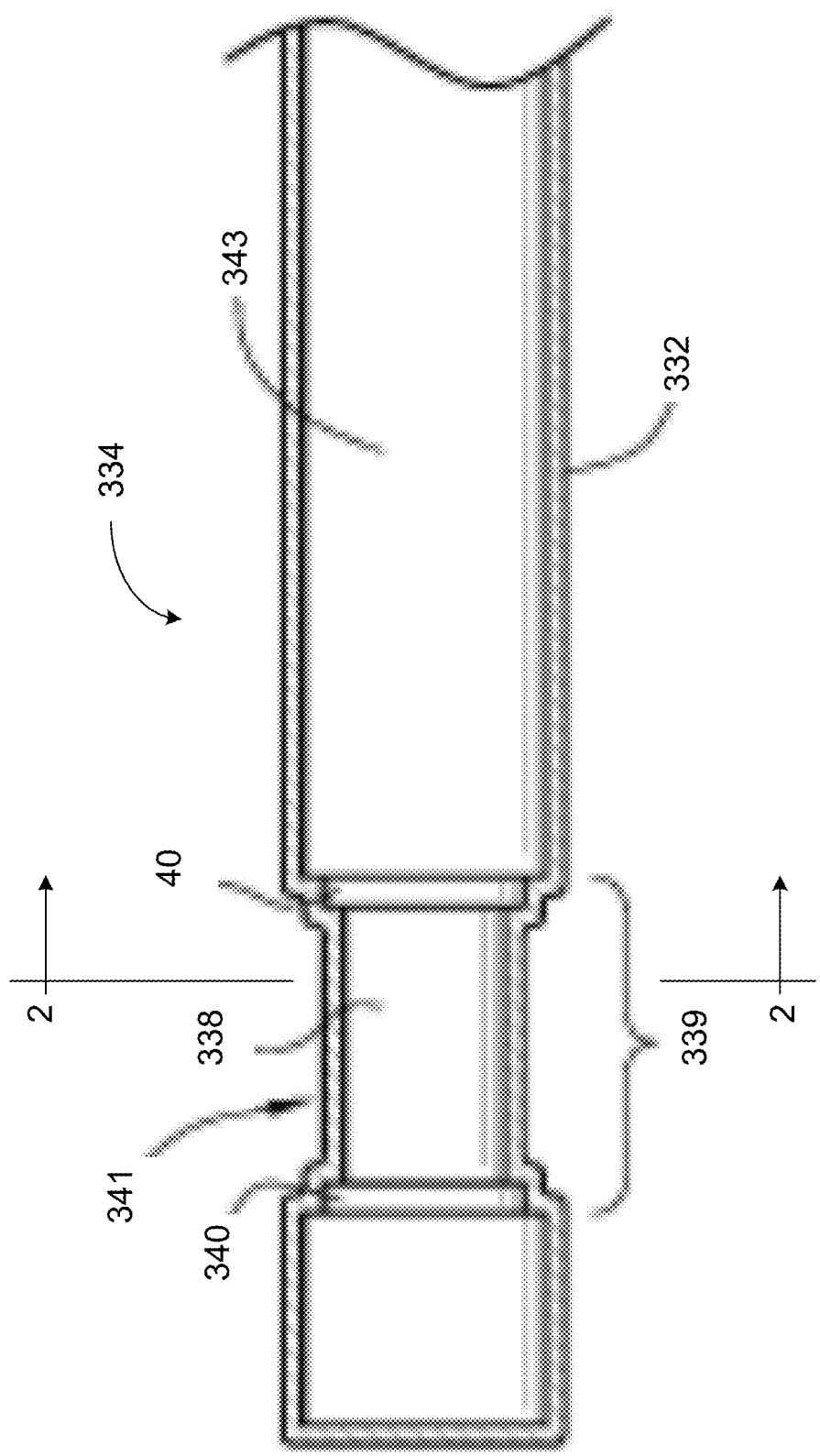
FIG. 4 is an enlarged view of an example analyte sensor portion of the analyte sensor system shown in FIG. 3.

FIG. 4 is an enlarged view of a distal portion of the analyte sensor 334. The analyte sensor 334 may be adapted for insertion under the host's skin and may be mechanically coupled to the mounting unit 314 and electrically coupled to the electronics unit 318. The example analyte sensor 334 shown in FIG. 4 includes an elongated conductive body 341. The elongated conductive body 341 can include a core with various layers positioned thereon. A first layer 338 that at least partially surrounds the core and includes a working electrode, for example located in window 339). In some examples, the core and the first layer 338 are made of a single material (such as, for example, platinum). In some examples, the elongated conductive body 341 is a composite of two conductive materials, or a composite of at least one conductive material and at least one non-conductive material. A membrane system 332 is located over the working electrode and may cover other layers and/or electrodes of the sensor 334, as described herein.

The first layer 338 may be formed of a conductive material. The working electrode (at window 339) is an exposed portion of the surface of the first layer 338. Accordingly, the first layer 338 is formed of a material configured to provide a suitable electroactive surface for the working electrode. Examples of suitable materials include, but are not limited to, platinum, platinum-iridium, gold, palladium, iridium, graphite, carbon, a conductive polymer, an alloy, and/or the like.

A second layer 340 surrounds at least a portion of the first layer 338, thereby defining boundaries of the working electrode. In some examples, the second layer 340 serves as an insulator and is formed of an insulating material, such as polyimide, polyurethane, parylene, or any other suitable insulating materials or materials. In some examples, the second layer 340 is configured such that the working electrode (of the layer 338) is exposed via the window 339.

In some examples, the sensor 334 further includes a third layer 343 comprising a conductive material. The third layer 343 may comprise a reference electrode. In some examples, the third layer 343, including the reference electrode, is formed of a silver-containing material that is applied onto the second layer 340 (e.g., an insulator). The silver-containing material may include various materials and be in various forms such as, for example, Ag/AgCl-polymer pasts, paints, polymer-based conducting mixtures, inks, etc.

The analyte sensor 334 may include two (or more) electrodes, e.g., a working electrode at the layer 338 and exposed at window 339 and at least one additional electrode, such as a reference electrode of the layer 343. In the example arrangement of FIGS. 3-5, the reference electrode also functions as a counter electrode, although other arrangements can include a separate counter electrode. While the analyte sensor 334 may be used with a mounting unit in some examples, in other examples, the analyte sensor 334 may be used with other types of sensor systems. For example, the analyte sensor 334 may be part of a system that includes a battery and sensor in a single package, and may optionally include, for example, a near-field communication (NFC) circuit.

Figure 5:
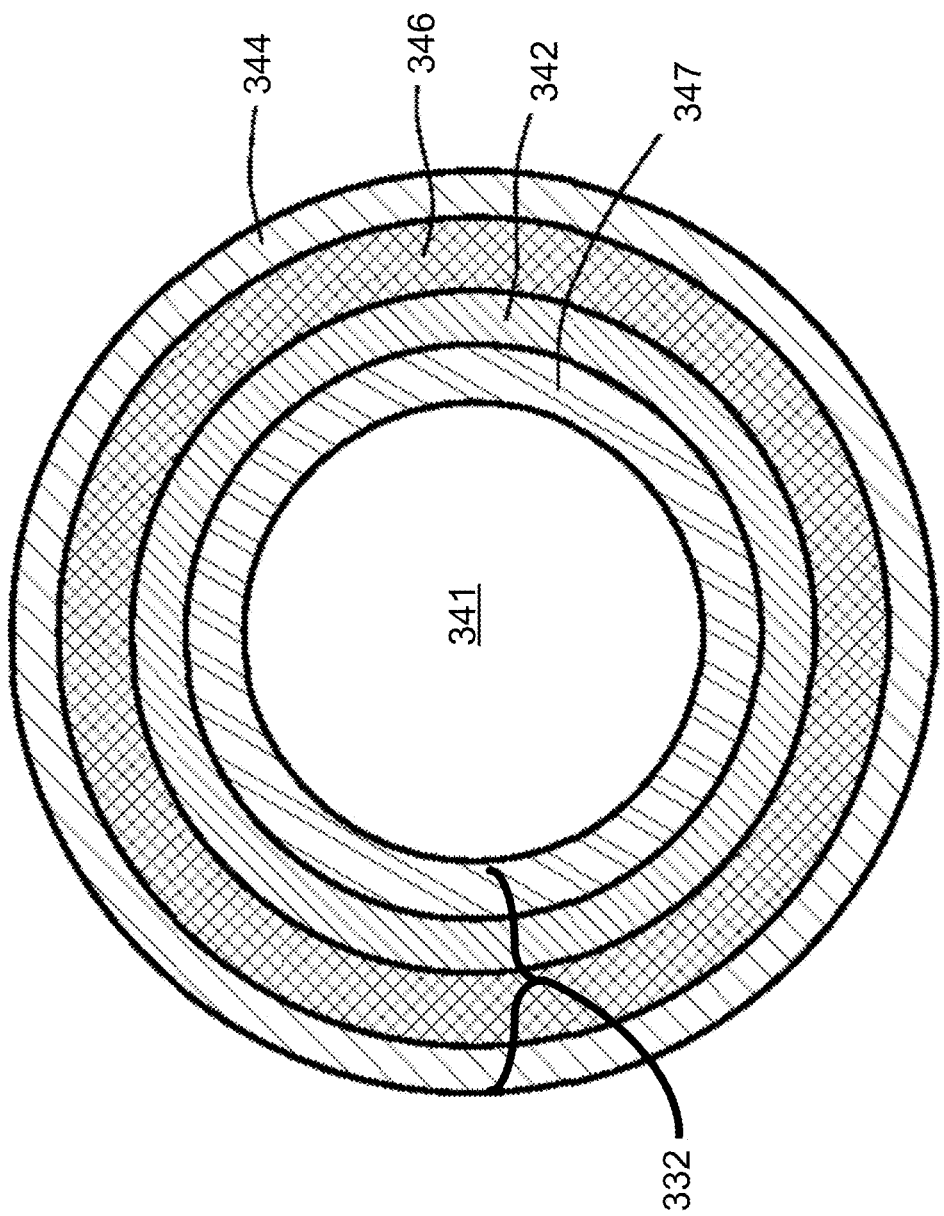
FIG. 5 is a cross-sectional view of the analyte sensor of FIGS. 3 and 4.

FIG. 5 is a cross-sectional view through the sensor 334 of FIG. 4 on plane 2-2 illustrating a membrane system 332. The membrane system 332 may include a number of domains (e.g., layers). In an example, the membrane system 332 may include an enzyme domain 342, a diffusion resistance domain 344, and a bioprotective domain 346 located around the working electrode. In some examples, a unitary diffusion resistance domain and bioprotective domain may be included in the membrane system 332 (e.g., wherein the functionality of both the diffusion resistance domain and bioprotective domain are incorporated into one domain).

The membrane system 332, in some examples, also includes an electrode layer 347. The electrode layer 347 may be arranged to provide an environment between the surfaces of the working electrode and the reference electrode that facilitates the electrochemical reaction between the electrodes. For example, the electrode layer 347 may include a coating that maintains a layer of water at the electrochemically reactive surfaces of the sensor 334.

In some examples, the sensor 334 may be configured for short-term implantation (e.g., from about 1 to 30 days). However, it is understood that the membrane system 332 can be modified for use in other devices, for example, by including only one or more of the domains, or additional domains. For example, a membrane system 332 may include a plurality of resistance layers, or a plurality of enzyme layers. In some example, the resistance domain 344 may include a plurality of resistance layers, or the enzyme domain 342 may include a plurality of enzyme layers.

The diffusion resistance domain 344 may include a semi-permeable membrane that controls the flux of oxygen and glucose to the underlying enzyme domain 342. As a result, the upper limit of linearity of glucose measurement is extended to a much higher value than that which is achieved without the diffusion resistance domain 344.

In some examples, the membrane system 332 may include a bioprotective domain 346, also referred to as a domain or biointerface domain, comprising a base polymer. However, the membrane system 332 of some examples can also include a plurality of domains or layers including, for example, an electrode domain, an interference domain, or a cell disruptive domain, such as described in more detail elsewhere herein and in U.S. Pat. Nos. 7,494,465, 8,682,608, and 9,044,199, which are incorporated herein by reference in their entirety.

It is to be understood that sensing membranes modified for other sensors, for example, may include fewer or additional layers. For example, in some examples, the membrane system 332 may comprise one electrode layer, one enzyme layer, and two bioprotective layers, but in other examples, the membrane system 332 may comprise one electrode layer, two enzyme layers, and one bioprotective layer. In some examples, the bioprotective layer may be configured to function as the diffusion resistance domain 344 and control the flux of the analyte (e.g., glucose) to the underlying membrane layers.

In some examples, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some examples, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode; for example, the enzyme domain 342 deposited over the working electrode does not necessarily need to be deposited over the reference or counter electrodes.

Although the examples illustrated in FIGS. 4-5 involve circumferentially extending membrane systems, the membranes described herein may be applied to any planar or non-planar surface, for example, the substrate-based sensor structure of U.S. Pat. No. 6,565,509 to Say et al., which is incorporated by reference.

In an example in which the analyte sensor 334 is a glucose sensor, glucose analyte can be detected utilizing glucose oxidase. Glucose oxidase reacts with glucose to produce hydrogen peroxide ($H_2O_2$). The hydrogen peroxide reacts with the surface of the working electrode, producing two protons ($2H^+$), two electrons ($2e^-$) and one molecule of oxygen ($O_2$). This produces an electronic current that may be detected by the sensor electronics 106. The amount of current is a function of the glucose concentration level. A calibration curve may be used to provide an estimated glucose concentration level based on a measured current. The amount of current is also a function of the diffusivity of glucose through the sensor membrane. The glucose diffusivity may change over time, which may cause the sensor glucose sensitivity to change over time, or "drift."

Figure 6:
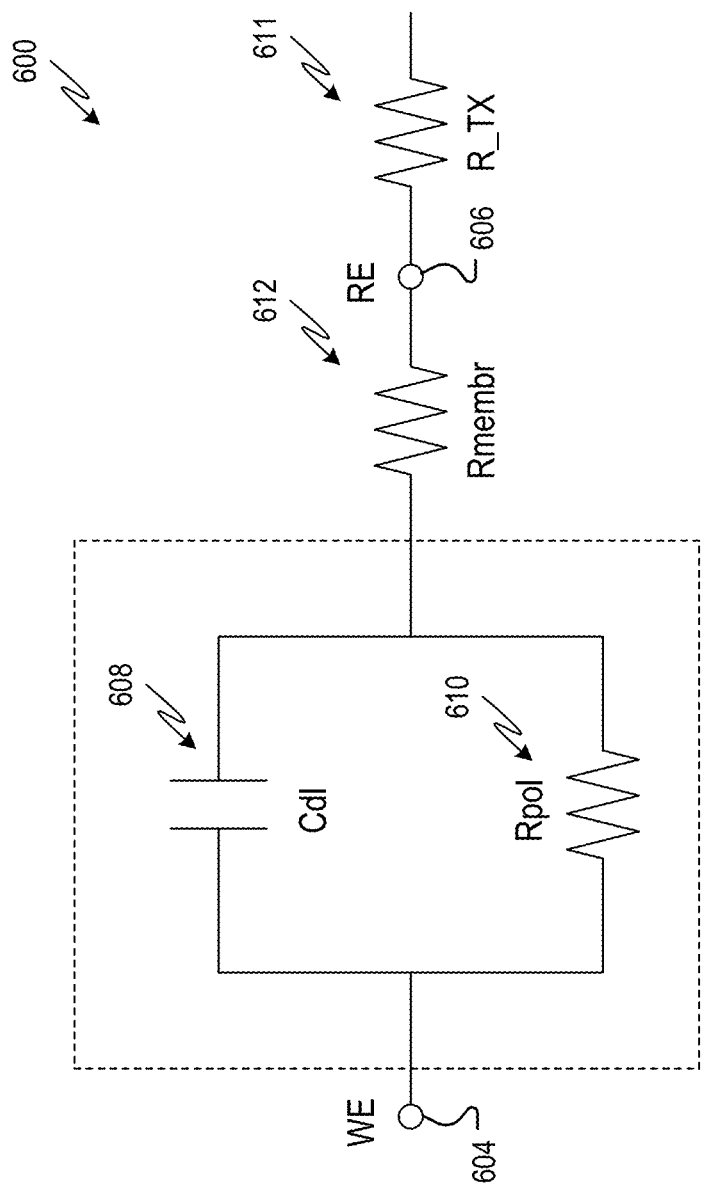
FIG. 6 is a schematic illustration of a circuit that represents the behavior of an example analyte sensor.

FIG. 6 is a schematic illustration of a circuit 600 that represents the behavior of an example analyte sensor, such as the analyte sensor 334 shown in FIGS. 3-5. As described above, the interaction of hydrogen peroxide (generated from the interaction between glucose analyte and glucose oxidase) and working electrode (WE) 604 produces a voltage differential between the working electrode (WE) 604 and reference electrode (RE) 606 which drives a current. The current may make up all or part of a raw sensor signal that is measured by sensor electronics, such as the sensor electronics 106 of FIGS. 1-2, and used to estimate an analyte concentration (e.g., glucose concentration).

The circuit 600 also includes a double-layer capacitance (Cdl) 608, which occurs at an interface between the working electrode (WE) 604 and the adjacent membrane (not shown in FIG. 6, see, e.g., FIGS. 3-5 above). The double-layer capacitance (Cdl) may occur at an interface between the working electrode 604 and the adjacent membrane due to the presence of two layers of ions with opposing polarity, as may occur during application of an applied voltage between the working electrode 604 and reference electrode. The equivalent circuit 600 may also include a polarization resistance (Rpol) 610, which may be relatively large, and may be modeled, for example, as a static value (e.g., 100 megaOhms), or as a variable quantity that varies as a function of glucose concentration level.

An estimated analyte concentration may be determined from a raw sensor signal based upon a measured current (or charge flow) through the analyte sensor membrane 612 when a bias potential is applied to the sensor circuit 600. For example, sensor electronics or another suitable computing device can use the raw sensor signal and a sensitivity of the sensor, which correlates a detected current flow to a glucose concentration level, to generate the estimated analyte concentration. In some examples, the device also uses a break-in characteristic, as described herein.

The change in glucose diffusivity over time presents a problem, in that two unknown variables (glucose concentration around the membrane 612 and glucose diffusivity in the membrane 612) are present in the system. For example, frequent blood glucose meter calibrations may be used to account for the drift, but this need for meter calibrations may be undesirable for a variety of reasons (e.g., inconvenience to the patient, cost, the potential for inaccurate blood glucose meter data, etc.).

With reference to the equivalent circuit 600, when a voltage is applied across the working and reference electrodes 604 and 606, a current may be considered to flow (forward or backward depending on polarity) through the internal electronics of transmitter (represented by R_Tx_internal) 611; through the reference electrode (RE) 606 and working electrode (WE) 604, which may be designed to have a relatively low resistance; and through the sensor membrane 612 (Rmembr, which is relatively small). Depending on the state of the circuit, current may also flow through, or into, the relatively large polarization resistance 610 (which is indicated as a fixed resistance, but may also be a variable resistance that varies with the body's glucose level, where a higher glucose level provides a smaller polarization resistance), or into the double-layer capacitance 608 (i.e., to charge the double-layer membrane capacitor formed at the working electrode 604), or both.

The impedance (or conductance) of the membrane (Rmembr) 612 is related to electrolyte mobility in the membrane, which is in turn related to glucose diffusivity in the membrane. As the impedance goes down (i.e., conductance goes up, as electrolyte mobility in the membrane 612 goes up), the glucose sensitivity goes up (i.e., a higher glucose sensitivity means that a particular glucose concentration will produce a larger signal in the form of more current or charge flow). Impedance, glucose diffusivity, and glucose sensitivity are further described in U.S. Patent Publication No. US2012/0262298, which is incorporated by reference in its entirety.

Figure 7:
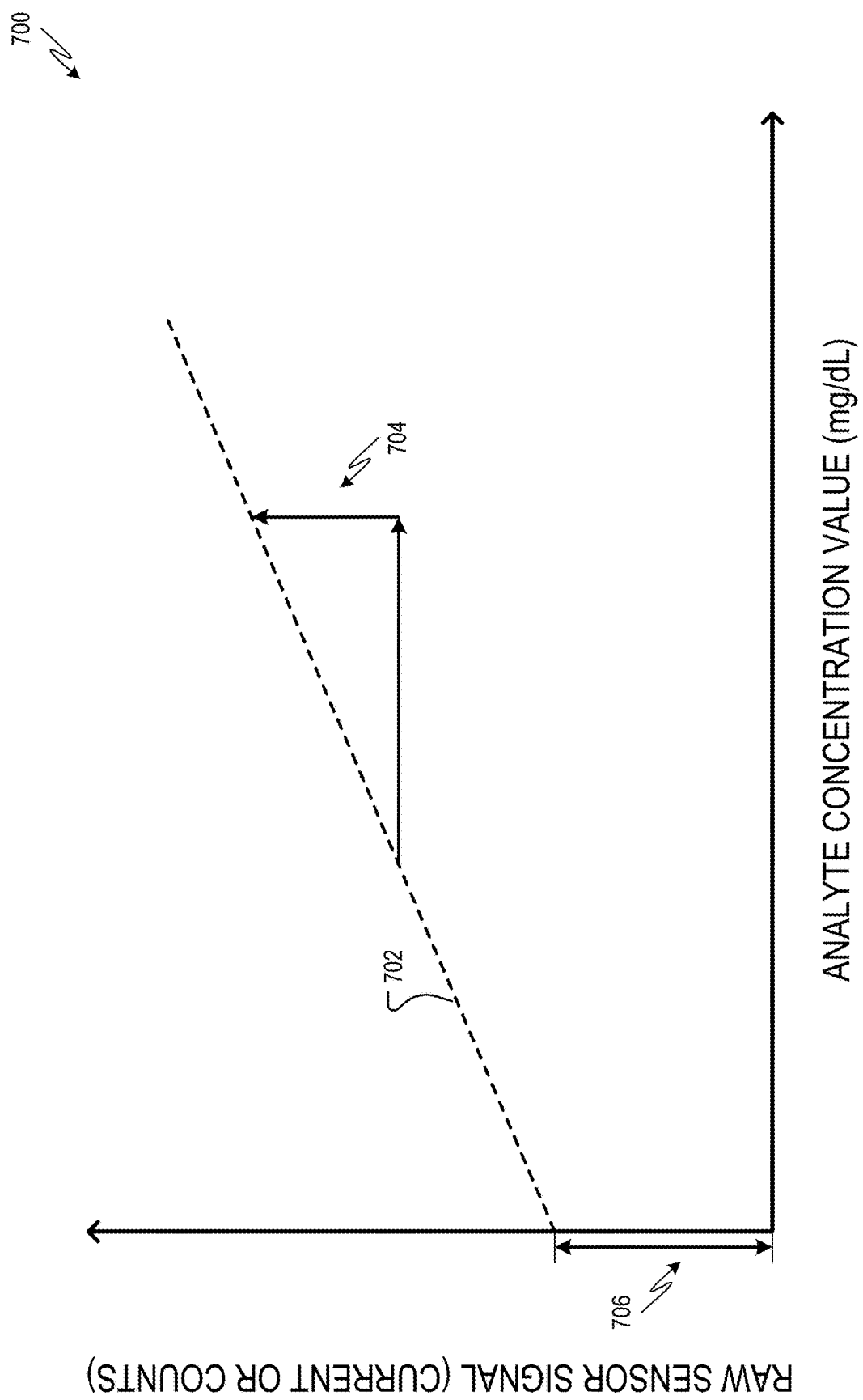
FIG. 7 is a chart showing one example of a conversion function illustrating a response of an example analyte sensor.

FIG. 7 is a chart 700 showing one example of a conversion function 702 illustrating a response of an example analyte sensor. The conversion function 702 shows a relationship between a raw sensor signal and an analyte concentration value for the example analyte sensor. In the chart 700, the horizontal or x-axis indicates the analyte concentration value. In this example, the analyte concentration value is indicated in milligrams per deciliter (mg/dL). The vertical or y-axis indicates a raw sensor signal, in this example indicated as a current or a count of charge generated at the analyte sensor.

The conversion function 702 is a line, indicating a linear relationship between the raw sensor signal and the analyte concentration value, as described herein. The conversion function 702 is characterized by a slope, referred to as the sensitivity 704. In this example, the sensitivity 704 is positive. The conversion function 702 is also characterized by an intercept 706. The intercept 706 indicates a level of charge or current that makes up the raw sensor signal when the analyte sensor is exposed to a zero concentration of the analyte. In some examples, the sensor electronics or other suitable device converts a raw sensor signal to an analyte concentration as indicated by Equation [1] below:

$$AC = (RSS - Intercept)/Sensitivity \quad [1]$$

In Equation [1], AC is the analyte concentration, shown on the horizontal or x-axis of the chart 700. RSS is the raw sensor signal, for example, indicated by a current or charge count. Intercept is the intercept 706 indicating the level of the raw sensor signal when the analyte concentration is zero. Sensitivity is the sensitivity 704 indicating the slope of the conversion function 702.

Equation [1], or a similar relationship, can be used to convert a raw sensor signal from an analyte sensor to a corresponding analyte concentration when the response of the analyte sensor is linear or substantially linear and the sensitivity and intercept are known. When the response of the analyte sensor is not linear, however, the relationship indicated by the conversion function 702 may not hold.

Figure 8:
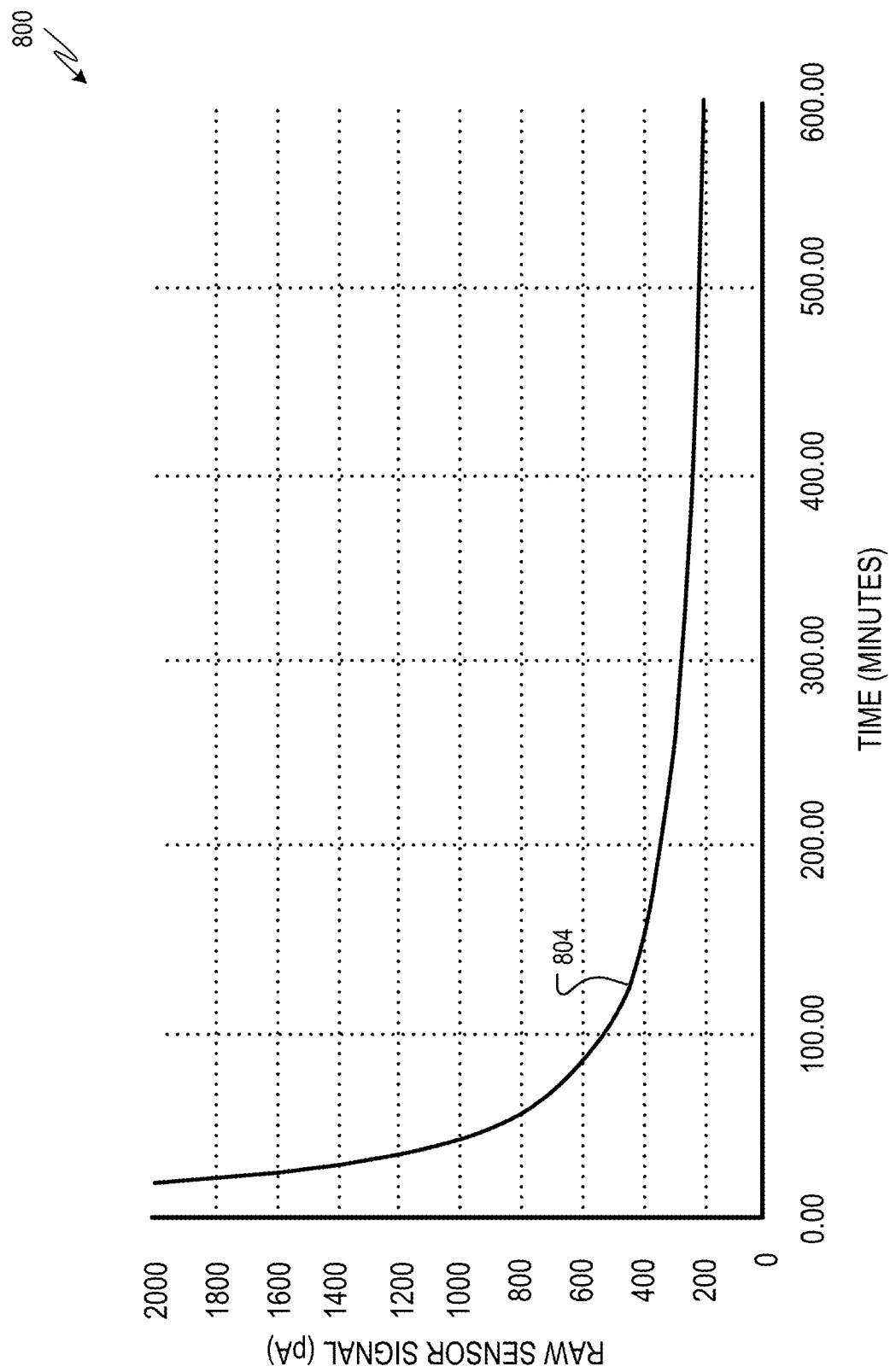
FIG. 8 is a chart showing a break-in curve for an example analyte sensor.

As described herein, however, the response of an analyte sensor may be nonlinear during break-in. This is illustrated by FIG. 8. FIG. 8 is a chart 800 showing a break-in curve 804 for an example analyte sensor. In the chart 800, the horizontal or x-axis indicates time in minutes. The vertical or y-axis indicates a raw sensor signal. In this example, the raw sensor signal is a current indicated in picoamps (pA). The break-in curve 804 indicates the response of the example analyte sensor.

In this example, the sensor is inserted, and the bias potential is applied at time zero. The analyte concentration is constant throughout the indicated time period. As shown, the current response is quite high initially and then decays towards a raw sensor signal of about 200 pA. The example break-in curve 804 shows results of both electrochemical break-in and membrane break-in. The high values of the raw sensor signal during break-in may be caused, at least in part, by non-analyte electrochemical reactions at the analyte sensor that occur after the bias potential is applied and contribute to electrochemical break-in. For some sensor configurations, non-analyte electrochemical reactions can include oxidation reactions that occur at the surface of the working electrode and/or reference electrode. As the surface of the sensor oxidizes, the contribution of oxidation reactions to the raw sensor signal may decrease. The high values of the raw sensor signal during break-in may also be caused, at least in part, by changes in the properties of the sensor membrane during hydration that contribute to membrane break-in.

The break-in of the analyte sensor continues until the raw sensor signal settles to a substantially linear response. In this example in which the analyte concentration is constant, the response of the analyte sensor may be linear when the raw sensor signal is also about constant. At this point the response of the analyte sensor to different analyte concentrations may substantially follow the linear response shown by the conversion function 702 of FIG. 7.

Various examples described herein are directed to apparatuses, systems, and methods for accelerating analyte sensor break-in or shifting break-in to occur, at least in part, before an analyte sensor is inserted in vivo. In some examples, break-in can be accelerated and/or shifted in to occur, at least in part, before sensor insertion by exposing the sensor to a hydrating agent while the sensor is packaged for storage and/or shipment. The hydrating agent hydrates the sensor such that some or all of membrane break-in occurs before the sensor is used in vivo. This can accelerate the break-in that occurs after the sensor is inserted in vivo. In this way, the time for the break-in curve to settle and the sensor to begin behaving in a manner similar to that shown in FIG. 7 is shortened.

In various examples, an analyte sensor is packaged with a sensor applicator. FIGS. 9, 10A-D, 11, 12, and 13 show example implementations of a sensor applicator. FIG. 9 is an exploded side view showing one example of a sensor applicator 912. In this example, the sensor applicator 912 includes an applicator body 918 that aides in aligning and guiding the sensor applicator components. The applicator body 918 includes an applicator body base 960 that matingly engages the mounting unit 914 (FIG. 11) and an applicator body cap 962 that enables appropriate relationships (for example, stops) between the sensor applicator components.

A guide tube subassembly 920 includes a guide tube carrier 964 and a guide tube 966. In some examples, the guide tube is a cannula. The guide tube carrier 964 slides along the applicator body 918 and maintains the appropriate relative position of the guide tube 966 during insertion and subsequent retraction. For example, prior to and during insertion of the sensor, the guide tube 966 extends through the contact subassembly 926 to maintain an opening that enables easy insertion of the needle therethrough (see FIGS. 10A to 10D). During retraction of the sensor, the guide tube subassembly 920 is pulled back, engaging with and causing the needle and associated moving components to retract back into the sensor applicator 912 (See FIGS. 10C and 10D). In some examples, a lubricant (e.g., petroleum jelly) is placed within the contact subassembly 926 such that it surrounds the guide tube 966 (e.g., cannula), thereby allowing the guide tube 966 to easily retract back into the sensor applicator 912, for example, without causing compression or deformation in the contact subassembly 926.

A needle subassembly 968 is provided that includes a needle carrier 970 and needle 972. The needle carrier 970 cooperates with the other sensor applicator components and carries the needle 972 between its extended and retracted positions. The needle 972 can be of any appropriate size that can encompass an analyte sensor 932 (FIGS. 10A-10D) and aid in its insertion into the host. Preferred sizes include from about 32 gauge or less to about 18 gauge or more, more preferably from about 28 gauge to about 25 gauge, to provide a comfortable insertion for the host. Referring to the inner diameter of the needle, approximately 0.006 inches to approximately 0.023 inches is preferable, and 0.013 inches is most preferable. The needle carrier 970 is configured to engage with the guide tube carrier 964, while the needle 972 is configured to slidably nest within the guide tube 966, which allows for easy guided insertion (and retraction) of the needle through the contact subassembly 926.

A push rod subassembly 974 is provided that includes a push rod carrier 976 and a push rod 978. The push rod carrier 976 cooperates with other sensor applicator components to ensure that the analyte sensor 932 is properly inserted into the host's skin, namely the push rod carrier 976 carries the push rod 978 between its extended and retracted positions. In this embodiment, the push rod 978 is configured to slidably nest within the needle 972, which allows for the analyte sensor 932 to be pushed (released) from the needle 972 upon retraction of the needle 972. This is described in more detail with reference to FIGS. 10A-10D. In some examples, a slight bend or serpentine shape is designed into or allowed in the sensor in order to maintain the sensor within the needle 972 by interference. While not wishing to be bound by theory, it is believed that a slight friction fit of the analyte sensor 932 within the needle 972 minimizes motion of the analyte sensor 932 during withdrawal of the needle 972 and maintains the analyte sensor 932 within the needle prior to withdrawal of the needle 972.

A plunger subassembly 922 is provided that includes a plunger 980 and plunger cap 982. The plunger subassembly 922 cooperates with other sensor applicator components to ensure proper insertion and subsequent retraction of the needle 972. In this example, the plunger 980 is configured to engage with the push rod 978 to ensure the analyte sensor 932 remains extended (namely, in the host) during retraction, such as is described in more detail with reference to FIG. 10C.

Figure 10A:
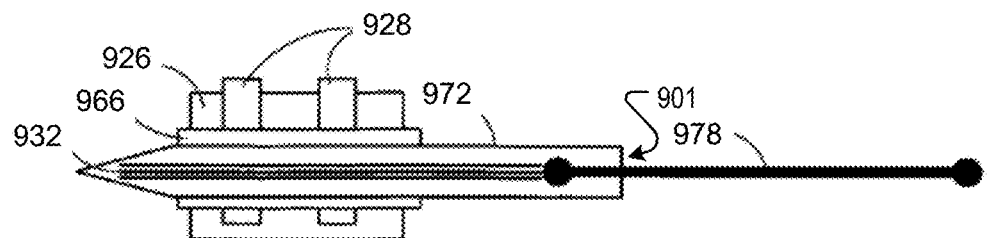
FIG. 10A shows one example of the needle and sensor of FIG. 9 loaded prior to sensor insertion.
Figure 10B:
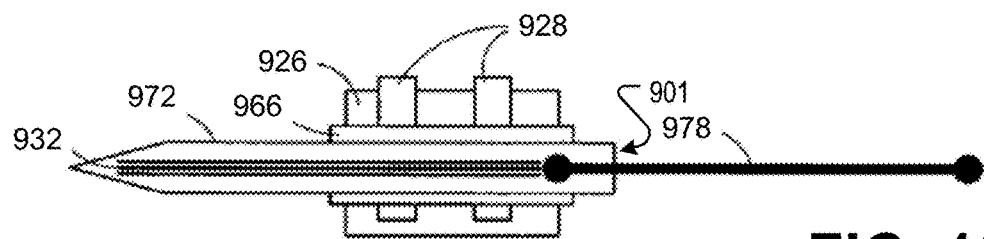
FIG. 10B shows one example of the needle and sensor after sensor insertion.
Figure 10C:
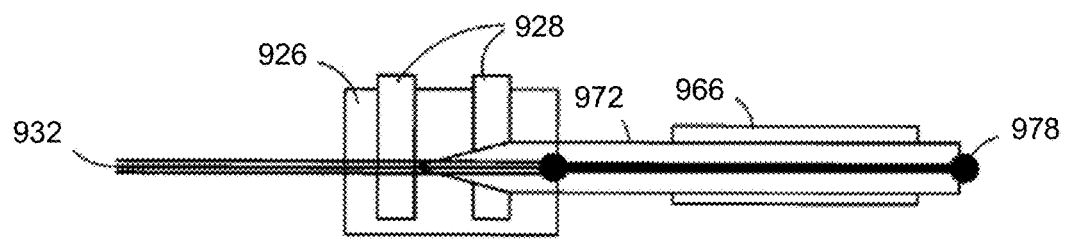
FIG. 10C shows one example of the sensor and needle during needle retraction.
Figure 10D:
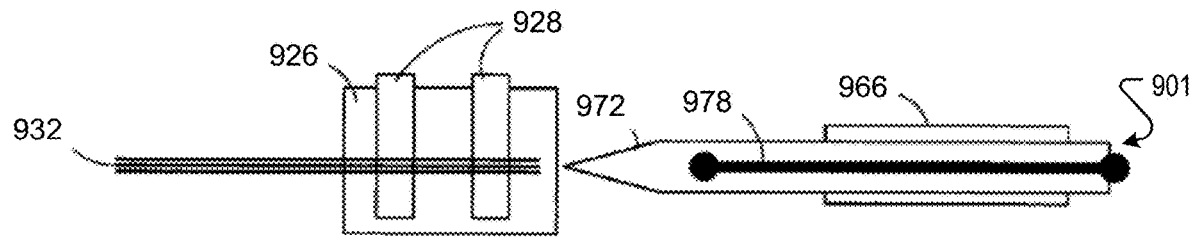
FIG. 10D shows one example of the sensor remaining within the contact subassembly after needle retraction.

FIGS. 10A through 10D are schematic side cross-sectional views that illustrate the applicator components and their cooperating relationships at various stages of sensor insertion. FIG. 10A shows one example of the needle 972 and analyte sensor 932 loaded prior to sensor insertion. FIG. 10B shows one example of the needle 972 and analyte sensor 932 after sensor insertion. FIG. 10C shows one example of the analyte sensor 932 and needle 972 during needle retraction. FIG. 10D shows one example of the analyte sensor 932 remaining within the contact subassembly 926 after needle retraction. Although the examples of FIGS. 9, 10A-10D and 11 suggest manual insertion and/or retraction of the various components, automation of one or more of the stages can also be employed. For example, spring-loaded mechanisms that can be triggered to automatically insert and/or retract the sensor, needle, or other cooperative applicator components can be implemented.

Referring to FIG. 10A, the analyte sensor 932 is shown disposed within the needle 972, which is disposed within the guide tube 966. In this example, the guide tube 966 is provided to maintain an opening within the contact subassembly 926 and/or contacts 928 to provide minimal friction between the needle 972 and the contact subassembly 926 and/or contacts 928 during insertion and retraction of the needle 972. However, the guide tube 966 is an optional component, which can be advantageous in some examples where the contact subassembly 926 and/or the contacts 928 are formed from an elastomer or other material with a relatively high friction coefficient. The guide tube 966 can be omitted, for example, in other examples in which the contact subassembly 926 and or the contacts 928 are formed from a material with a relatively low friction coefficient (for example, hard plastic or metal). A guide tube 966, or the like, may be advantageous in examples in which the contact subassembly 926 and/or the contacts 928 are formed from a material designed to frictionally hold the analyte sensor 932 (see FIG. 10D), for example, by the relaxing characteristics of an elastomer, or the like. In these examples, the guide tube 966 may be provided to ease insertion of the needle 972 through the contacts 928, while allowing for a frictional hold of the contacts 928 on the analyte sensor 932 upon subsequent needle retraction. Stabilization of the analyte sensor 932 in or on the contacts 928 is described in more detail with reference to FIG. 10D. Although FIG. 10A illustrates the needle 972 and analyte sensor 932 inserted into the contacts subassembly 926 as the initial loaded configuration, alternative embodiments contemplate a step of loading the needle 972 through the guide tube 966 and/or contacts 928 prior to sensor insertion.

Referring to FIG. 10B, the analyte sensor 932 and needle 972 are shown in an extended position. In this stage, the push rod 978 has been forced to a forward position, for example by pushing on the plunger shown in FIG. 7, or the like. The plunger 980 (FIG. 9) is designed to cooperate with other of the sensor applicator components to ensure that analyte sensor 932 and the needle 972 extend together to a forward position (as shown). For example, the push rod 978 may be designed to cooperate with other of the sensor applicator components to ensure that the analyte sensor 932 maintains the forward position simultaneously within the needle 972.

Referring to FIG. 10C, the needle 972 is shown during the retraction process. In this stage, the push rod 978 is held in its extended (forward) position in order to maintain the analyte sensor 932 in its extended (forward) position until the needle 972 has substantially fully retracted from the contacts 928. Simultaneously, the cooperating sensor applicator components retract the needle 972 and guide tube 966 backward by a pulling motion (manual or automated) thereon. In preferred embodiments, the guide tube carrier 964 (FIG. 9) engages with cooperating applicator components such that a backward (retraction) motion applied to the guide tube carrier retracts the needle 972 and guide tube 966, without (initially) retracting the push rod 978. In an alternative embodiment, the push rod 978 can be omitted and the analyte sensor 932 held it its forward position by a cam, elastomer, or the like, which is in contact with a portion of the sensor while the needle moves over another portion of the sensor. One or more slots can be cut in the needle to maintain contact with the sensor during needle retraction.

Referring to FIG. 10D, the needle 972, guide tube 966, and push rod 978 are all retracted from contact subassembly 926, leaving the analyte sensor 932 disposed therein. The cooperating sensor applicator components are designed such that when the needle 972 has substantially cleared from the contacts 928 and/or contact subassembly 926, the push rod 978 is retracted along with the needle 972 and guide tube 966. The sensor applicator 912 can then be released (manually or automatically) from the contacts 928.

In various examples, the contacts 928 are elastomeric contacts to ensure a retention force that retains the analyte sensor 932 within the mounting unit and to ensure stable electrical connection of the analyte sensor 932 and its associated contacts 928. Although the illustrated embodiments and associated text describe the analyte sensor 932 extending through the contacts 928 to form a friction fit therein, a variety of alternatives are contemplated. In some examples, the sensor 932 is configured to be disposed adjacent to the contacts 928 (rather than between the contacts 928). The contacts 928 can be constructed in a variety of known configurations, for example, metallic contacts, cantilevered fingers, pogo pins, or the like, which are configured to press against the sensor after needle retraction.

The illustrated embodiments are designed with coaxial contacts 928; namely, the contacts 928 are configured to contact the working and reference electrodes of the analyte sensor 932 axially along a distal portion of the analyte sensor 932. For example, the working electrode of the analyte sensor 932 may extend farther than the reference electrode, which allows coaxial connection of the electrodes with the contacts 928 at locations spaced along the distal portion of the sensor.

Figure 11:
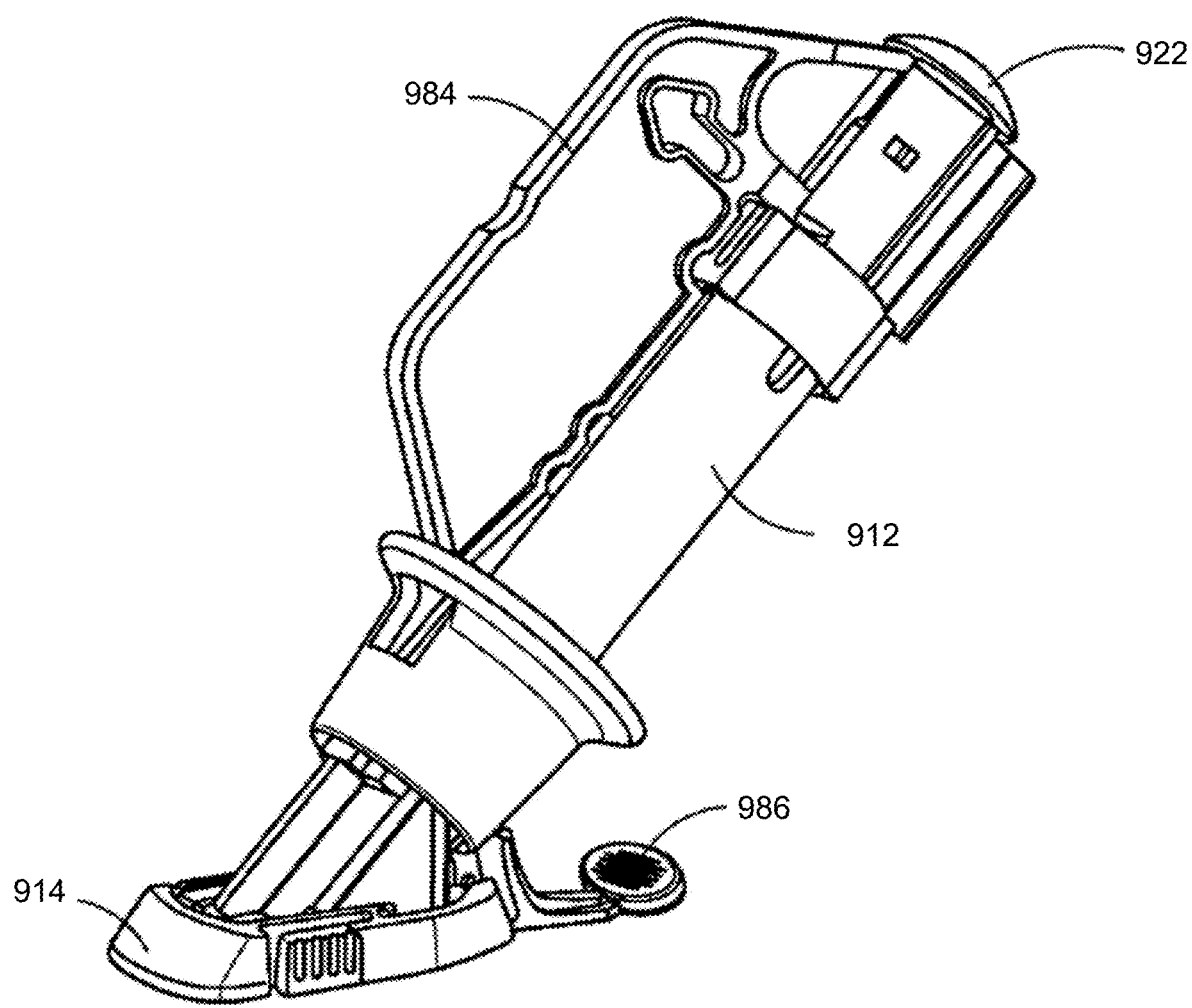
FIG. 11 is a perspective view of the sensor applicator of FIG. 9 and a mounting unit according to one example including a safety latch mechanism.

FIG. 11 is a perspective view of a sensor applicator 912 and mounting unit 914 according to one example including a safety latch mechanism 984. The safety latch mechanism 984 is configured to lock the plunger subassembly 922 in a stationary position such that it cannot be accidentally pushed prior to release of the safety latch mechanism 984. In this example, the analyte sensor 932 is preferably packaged (e.g., shipped) in this locked configuration, where the safety latch mechanism 984 holds the plunger subassembly 922 in its extended position. This may prevent the analyte sensor 932 from being prematurely inserted (e.g., accidentally released). The safety latch mechanism 984 may be configured configured such that a pulling force shown in the direction of the arrow (see FIG. 11) releases the lock of the safety latch mechanism 984 on the plunger subassembly 922, thereby allowing sensor insertion. Although one safety latch mechanism 984 that locks the plunger subassembly 922 is illustrated and described herein, a variety of safety latch mechanism configurations that lock the sensor to prevent it from prematurely releasing (i.e., that lock the sensor prior to release of the safety latch mechanism) are contemplated, as can be appreciated by one skilled in the art, and fall within the scope of the preferred embodiments.

FIG. 11 additionally illustrates a force-locking mechanism 986 included in certain alternative embodiments of the sensor system, wherein the force-locking mechanism 986 is configured to ensure a proper mate between an electronics unit (e.g., electronics unit 318 of FIG. 3) and the mounting unit 914. In some circumstances, it can be advantageous to ensure the electronics unit has been properly mated (e.g., snap-fit or sealingly mated) to the mounting unit. Accordingly, upon release of the sensor applicator 912 from the mounting unit 914 (after sensor insertion), and after insertion of the electronics unit 916 into the mounting unit 914, the force-locking mechanism 986 allows the user to ensure a proper mate and/or seal therebetween. In practice, a user pivots (e.g., lifts or twists) the force-locking mechanism such that it provides force on the electronics unit 916 by pulling up on the circular tab illustrated in FIG. 11. The force-locking mechanism is preferably released thereafter. Although one system and one method for providing a secure and/or sealing fit between the electronics unit and the mounting unit are illustrated, various other force-locking mechanisms can be employed that utilize a variety of systems and methods for providing a secure and/or sealing fit between the electronics unit and the mounting unit (housing).

In some examples, the sensor applicator 912 shown in FIGS. 9, 10A-10D, and 11 can be configured to carry a hydrating agent to hydrate the sensor 932. For example, referring to FIGS. 10A and 10B, the hydrating agent may be positioned within a lumen 901 of the needle 972. The hydrating agent may be or include any suitable substance that tends to hydrate the membrane of the analyte sensor 932. In some examples, the hydrating agent is aqueous based. In some examples, the hydrating agent is substantially free of alcohols, organic constituents and/or other materials that may tend to change the membrane permeability, for example, due to swelling, leaching of hydrophobic domains, etc. In some examples, the hydrating agent is also selected to avoid extracting hydrophilic domains of the membrane, as this may affect analyte flux through the membrane and change the sensitivity of the analyte sensor.

In some examples, the hydrating agent is provided with a viscosity suitable for retaining the hydrating agent inside the lumen 901 of the needle 972. For example, the hydrating agent may be a foam, a gel, or in a similar state. In some examples, the push rod 978 is positioned at a proximal end of the needle 972 in the lumen 901. In this way the push rod 978 can be positioned to prevent leakage of the hydrating agent from the lumen 901 at the proximal end. In some examples where the viscosity of the hydrating agent is not sufficient to hold the hydrating agent within the lumen 901, a plug material is positioned at a distal end of the lumen 901. The plug can be made from a foam, a gel, or any other suitable material for securing the hydrating agent within the lumen 901. In other examples, the distal end of the needle 972 is positioned against an adhesive pad, such as the adhesive pad 1210 of FIG. 12, while the analyte sensor applicator 912 is packaged. The adhesive pad may be positioned to attenuate leakage of the hydrating agent from the distal end of the lumen 901. When the sensor is installed, the needle 972 punctures the adhesive pad and enters the skin of the host.

In some examples, the hydrating agent is or includes a humectant gel. The hydrating agent can comprise various components including a hydrating agent (also referred to as a humectant), a buffering agent, a viscosity modifier, a solvent preservatives, lubricants, surfactants, antiadherents, fillers, and combinations thereof. The hydrating agent may be non-toxic, nonirritant, and noncorrosive to the needle and packaging materials. In some examples, the hydrating agent can be selected so as not to solidify under normal storage conditions. The hydrating agent may be colorless or of a mild color. Also, the hydrating agent may be selected to retain water under normal storage conditions.

Example hydrating agents can include organic humectants, metal organic humectants, and/or inorganic humectants. In some examples, organic humectants are used because organic humectants may be inert to metal and compatible with gel formulation. Examples of organic humectants that may be used as all or part of the hydrating agent include glycerol, ethylene glycol, polyethylene glycol (PEG), diethylene glycol, triethylene glycol, propylene glycol, dipropylene glycol, glycerin sorbitol, mannitol, and glucose.

In some examples, superabsorbent inorganic or organic material may be incorporated into a hydrating agent gel formulation. The suberabsorbants may include, for example, anionic or cationic polymers. Examples of superabsorbants include poly (methacrylic acid) sodium salt, poly (acrylic acid) sodium salt, polyacrylamide, polyvinyl alcohol, polysaccharides, and/or proteins.

In some examples, the hydrating agent is capable of absorbing between about 30% and 130% of water relative to dry material. In some examples, the hydrating agent is capable of absorbing between about 50% and 100% of water relative to dry material. In some examples, the hydrating agent is selected to retain at least between about 30% and 80% of the water absorbed after exposure to normal storage conditions for one year. In some examples, the hydrating agent is selected to retain about 50% of the water absorbed after exposure to normal storage conditions for one year.

Figure 12:
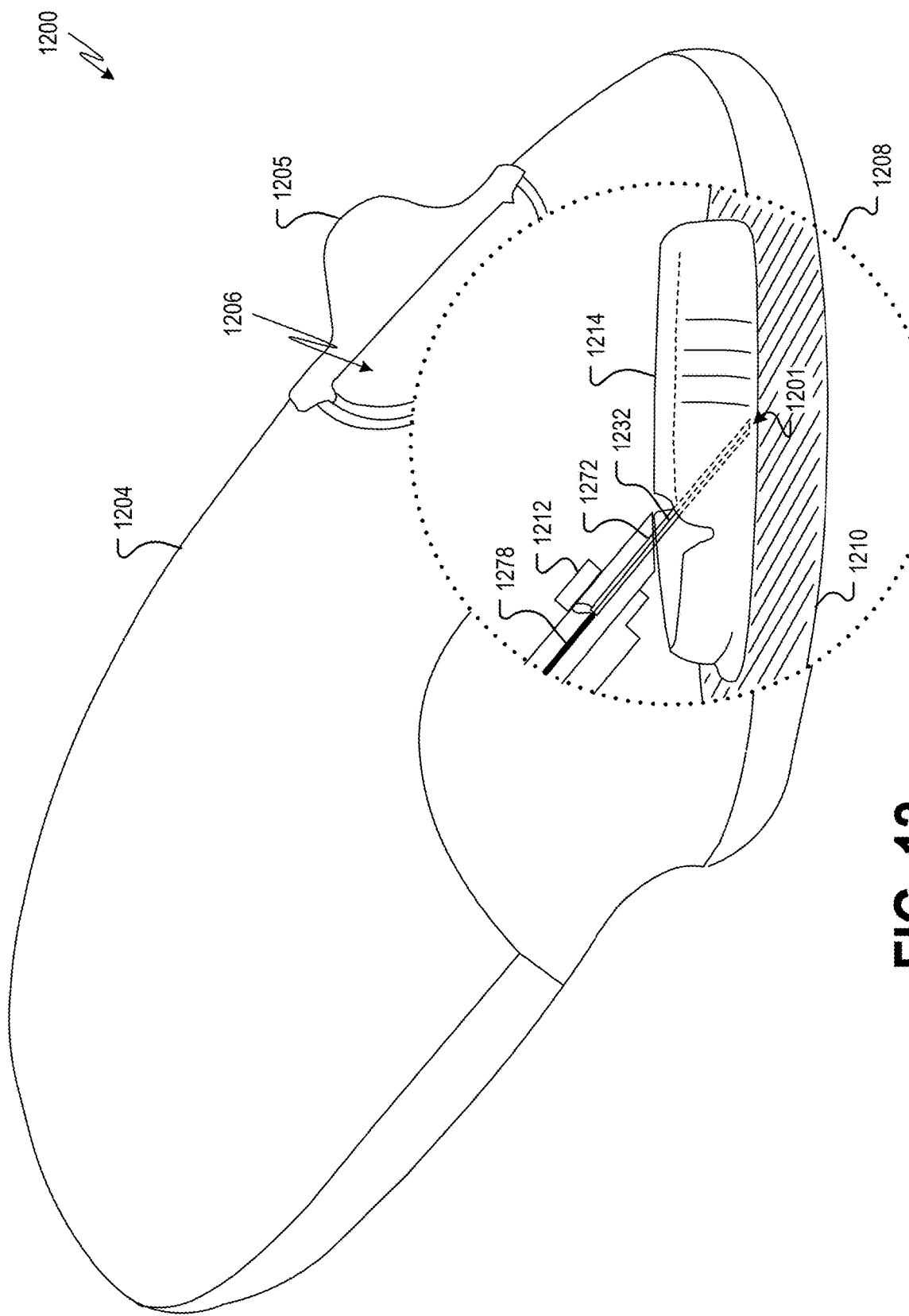
FIG. 12 is a diagram showing another example of an analyte sensor applicator including a needle configured to contain a hydrating agent for hydrating a membrane of an analyte sensor.

FIG. 12 is a diagram showing another example of an analyte sensor applicator 1200 including a needle 1202 configured to contain a hydrating agent for hydrating a membrane of an analyte sensor 1232. In the example of FIG. 12, the sensor applicator 1200 includes an enclosure 1204. The sensor applicator 1200 is automated and, for example, includes a spring-loaded mechanism for initiating sensor insertion (not shown in FIG. 12). For example, the spring-loaded mechanism may be actuated by depressing an insertion button 1206. A safety latch mechanism 1205 is positioned over the insertion button 1206 to prevent accidental insertion of the analyte sensor 1232. The safety latch mechanism 1205 can be removed, for example, by pulling it away from the enclosure 1204.

FIG. 12 includes a window 1208 showing components that are inside of the enclosure 1204 including, for example, a needle 1272 and a mounting unit 1214. The mounting unit 1214 is coupled to an example adhesive pad 1210 for adhering the mounting unit 1214 to the skin of a host. A push rod 1278 may operate in a manner similar to that of the push rod 978 described above to push the analyte sensor 1232 into the host. A lumen 1201 of the needle 1272 can include a hydrating agent, for example, as described herein.

The example of FIG. 12 also includes a battery 1212. The battery 1212 can include any suitable type of battery cell or cells. The battery 1212 can be electrically connected to the analyte sensor 1232 to provide a bias potential to the analyte sensor 1232 while the analyte sensor 1232 is packaged for storage and/or shipping. For example, the analyte sensor 1232 can be packaged within the lumen 1201 while the battery 1212 provides the bias potential. Providing the bias potential to the analyte sensor 1232 while the analyte sensor 1232 is packaged may cause the electrochemical break-in to begin during packaging. In this way, electrochemical break-in in vivo may be reduced and/or eliminated. In some examples, the battery 1212 provides the bias potential while the needle 1272 is in contact with the hydrating agent.

In some examples, the bias potential provided by the battery 1212 during packaging of the analyte sensor 1232 is greater than an operating bias potential of the analyte sensor 1232. The operating bias potential of the analyte sensor 1232 may be a potential to which the analyte sensor 1232 is biased during in vivo use. In some examples, battery 1212 provides a potential bias that is about 50% greater than the operating bias potential. In some examples, the battery 1212 provides a potential bias that is more than 50% greater than the operating bias potential. In some examples, the battery 1212 provides a potential bias that is between about 10% and 50% greater than the operating bias potential. In some examples, the operating bias potential of the analyte sensor 1232 is about 600 mV and the bias potential provided by the battery 1212 is about 1600 mV.

The example of FIG. 12 shows the mounting unit 1214 that is configured to receive a sensor electronics unit (not shown in FIG. 12) where the sensor electronics unit includes another battery or power source as described above. In some examples, an analyte sensor is incorporated into a package that includes both the analyte sensor (or contacts for coupling to the analyte sensor) and sensor electronics including a battery or other power supply in a single unit. In this example, the sensor electronics, including a corresponding battery or other power supply, may be incorporated into the analyte sensor applicator 1200 (and may be packaged in a manner similar to that shown in FIG. 13). In the examples shown in FIG. 12 as well as in embodiments with an integrated package for an analyte sensor and sensor electronics, the bias potential can be applied to the analyte sensor before, during, and/or after insertion.

Figure 13:
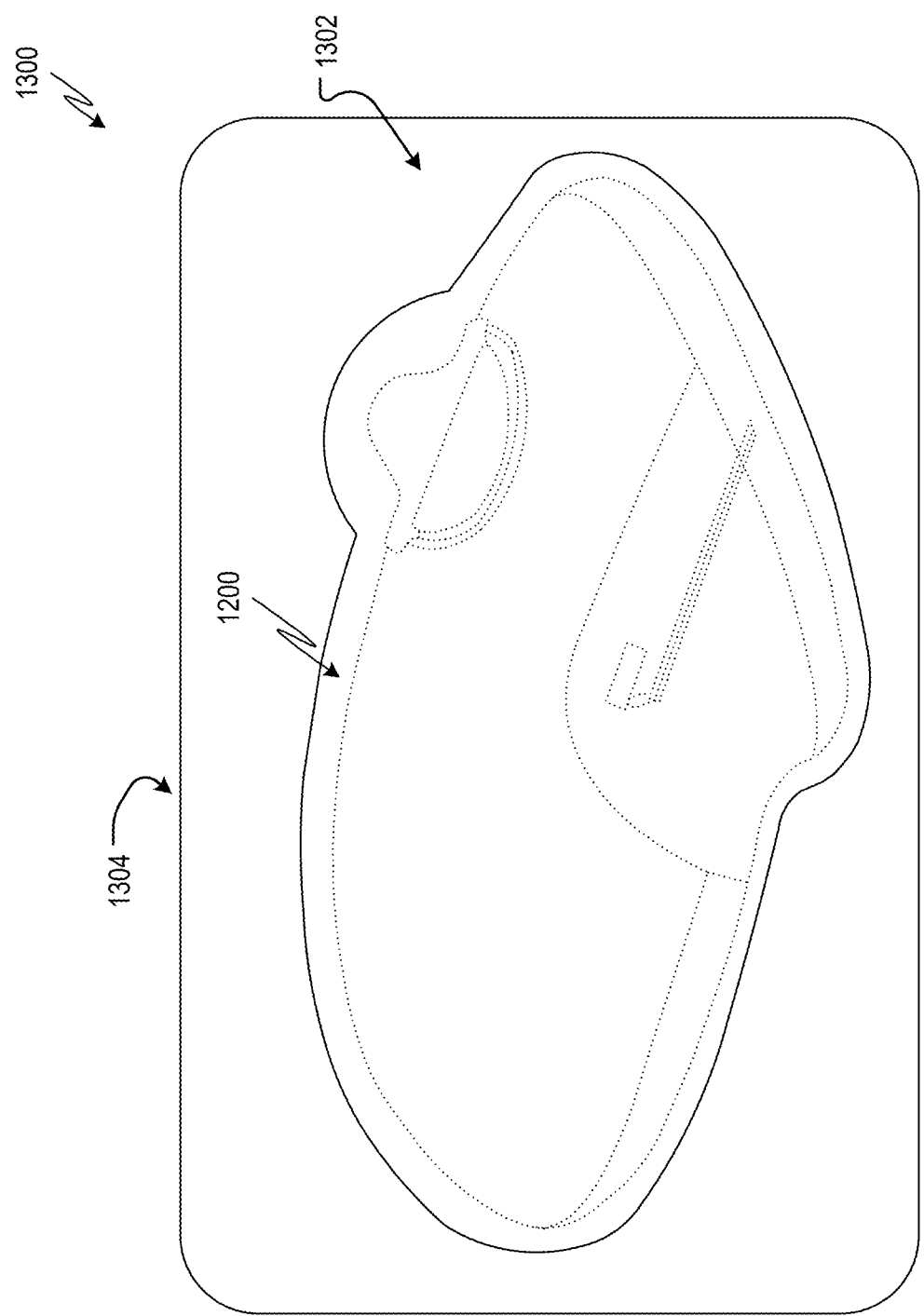
FIG. 13 is a diagram showing one example of a packaging that can be used to enclose the sensor applicator of FIG. 12.

FIG. 13 is a diagram showing one example of a packaging 1300 that can be used to enclose the sensor applicator 1200 of FIG. 12. The packaging 1300 may include, for example, a blister portion 1302 made of a plastic or other suitable material. The blister portion 1302 can be sealed on a back side 1304 with a sealing material, such as, for example, high-density polyethylene fibers (e.g., Tyvek® or another suitable material. In some examples, the sensor applicator 1200 including the analyte sensor 1232 is sealed in the packaging 1300 for shipment and/or packaging. The packaging 1300 can be sterilized using any suitable sterilization such as, for example, electron beam sterilization or ethylene oxide sterilization. Inside the packaging 1300, the sensor applicator 1200 may include the needle 1272 and sensor 1232 with a hydrating agent present in the lumen 1201 of the needle 1272. Further, in some examples, the battery 1212 is also present inside the packaging 1300 to provide the bias potential in the packaging 1300 as described herein.

Figure 29:
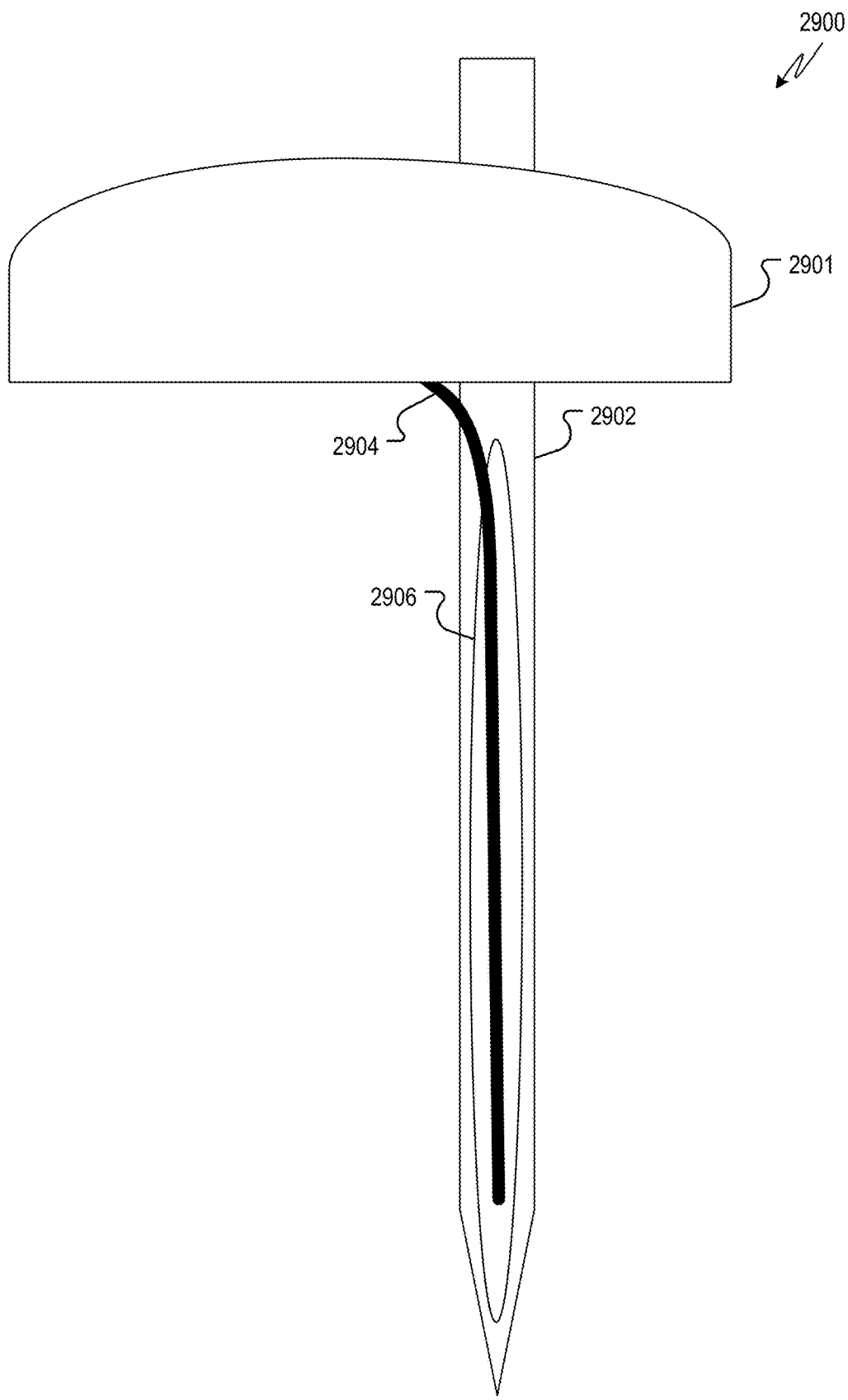
FIG. 29 is a diagram showing an example of a sensor arrangement showing a hydrating agent in contact with a sensor.

FIG. 29 is a diagram showing an example of a sensor arrangement 2900 showing a hydrating agent in contact with a sensor 2906. The arrangement 2900 includes a mounting unit 2901, a needle 2902, and a sensor 2904. The sensor 2904 is surrounded by a hydrating agent 2906, as described herein. The needle 2902 may be operated, for example, in the manner described herein to insert the sensor 2906 completely or partially under the skin of a host. The hydrating agent 2906 may be deposited on the sensor 2904 in any suitable manner. For example, the hydrating agent 2906 may be dip coated, dip coated, and/or brush coated onto the sensor 2904 (e.g., before the sensor 2904 is inserted in the needle 2902).

Figure 30:
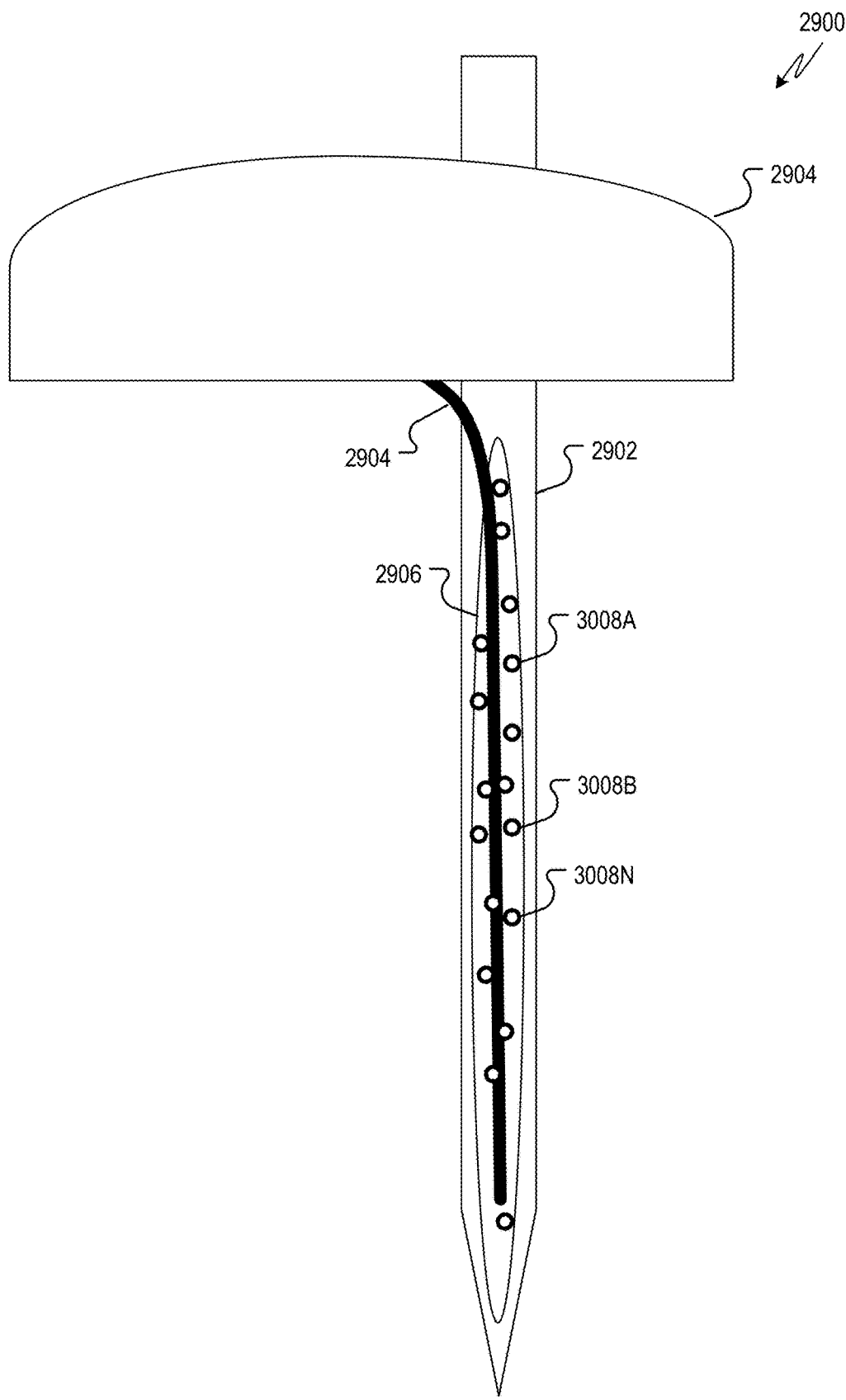
FIG. 30 is a diagram showing an example of the sensor arrangement of FIG. 29 with the hydrating agent including superabsorbent particles.

FIG. 30 is a diagram showing an example of the sensor arrangement 2900 of FIG. 29 with the hydrating agent 2906 including superabsorbent particles 3008A, 3008B, 3008N. Additional superabsorbent particles are shown, but for purposes of clarity, are not labeled. The superabsorbent particles can be incorporated into the hydrating agent in any suitable manner. Also, in various examples, the depositing techniques described with respect to FIGS. 29 and 30 may also be used with various other arrangements for packaging sensors with hydrating agents, for example, as described herein.

In some examples, the behavior of an analyte sensor during break-in depends both on the time since the analyte sensor was inserted into the host and the time that the bias potential was applied to the analyte sensor. If sensor insertion and the application of the bias potential do not occur at about the same time, then the behavior of the analyte sensor during break-in may be different. For example, some hosts or other users may insert the analyte sensor but delay in installing the electronics unit. If this occurs, the membrane break-in may begin when the analyte sensor is inserted into the host while electrochemical break-in begins later when the bias potential is applied to the analyte sensor. Also, in some examples, membrane break-in may occur differently in the absence of the bias potential.

Differences in analyte sensor break-in behavior due to delayed application of the bias potential can cause problems, for example, if an analyte sensor system is configured to apply a break-in correction. A break-in characteristic of the analyte sensor derived under conditions in which the bias potential was applied at about the same time that the sensor was inserted may not accurately describe the behavior of the analyte sensor if the application of the bias potential is delayed. This can lead to less accurate analyte concentration readings during break-in. Also, in some examples, delayed application of the bias potential after sensor insertion may cause differences in the duration of break-in, which may affect when and/or how an analyte sensor system begins to apply a standard linear response to generate analyte concentrations from raw sensor signals (e.g., as shown in FIG. 7).

Figure 14:
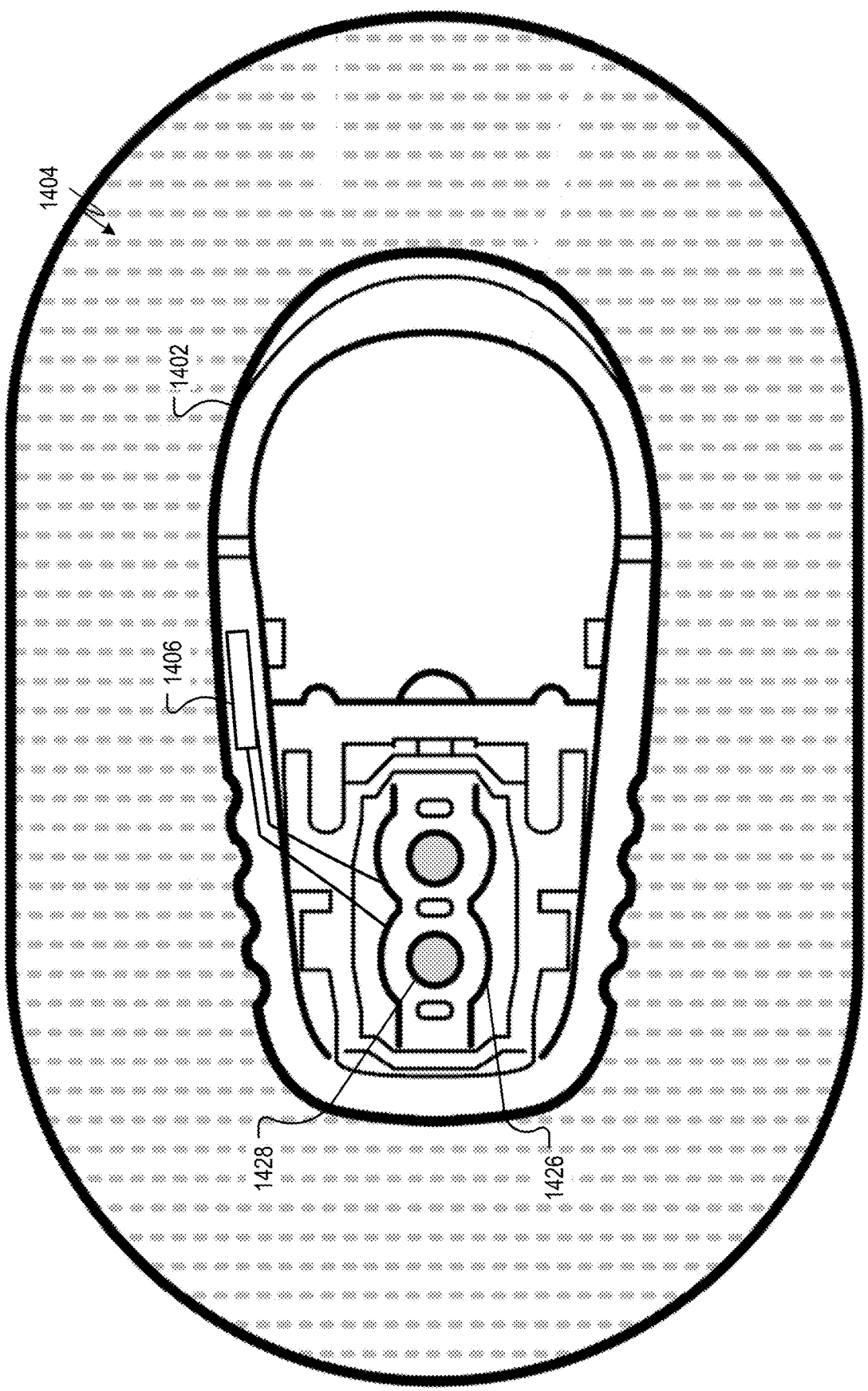
FIG. 14 is a diagram showing one example of a sensor mounting unit including a battery configured to provide a bias potential to contacts of a contact assembly that may be electrically coupled to an analyte sensor.

These and/or other challenges may be addressed by configuring an analyte sensor and sensor mounting unit with a battery that is configured to begin applying a bias potential to the analyte sensor upon sensor insertion even if the installation of the electronics unit is delayed. FIG. 14 is a diagram showing one example of a sensor mounting unit 1402 including a battery 1406 configured to provide a bias potential to contacts 1428 of a contact assembly 1426 that may be electrically coupled to an analyte sensor (not shown in FIG. 14). For example, one of the contacts 1428 may be electrically coupled to the working electrode of the analyte sensor. The other contact 1428 may be electrically coupled to the reference electrode of the analyte sensor.

The battery 1406 can include any suitable type of cell or cells for generating the bias potential. In some examples, the battery is a self-powered battery. For example, an anode and/or a cathode of the battery 1406 can be placed in contact with host tissue, such as interstitial fluid or other bodily fluid, which can act as an electrolyte to generate the bias potential. In some examples, all or part of an anode and/or cathode of the battery 1406 can be incorporated into the analyte sensor (not shown in FIG. 14) that is inserted under the skin of the patient, providing contact with the interstitial fluid.

Figure 15:
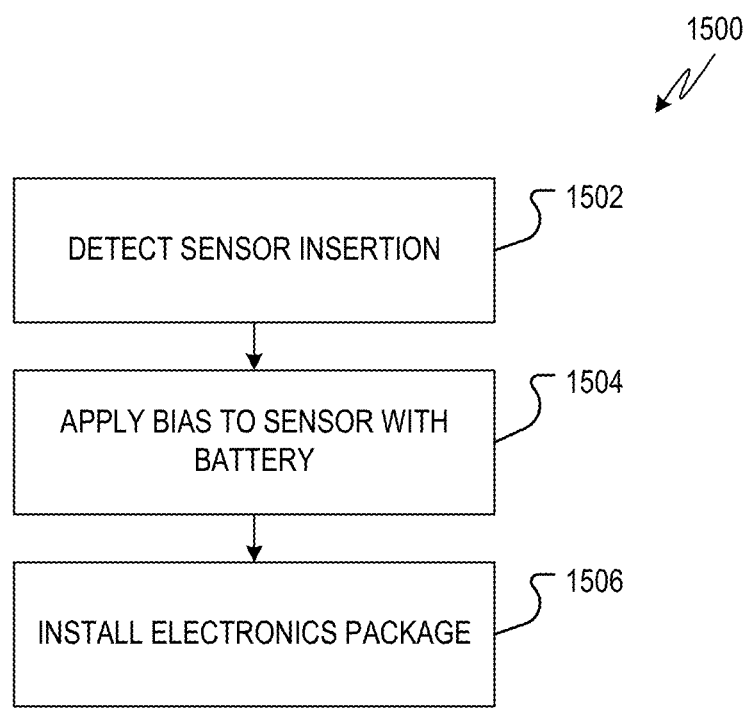
FIG. 15 is a flowchart showing one example of a process flow that can be executed using the sensor mounting unit and battery of FIG. 14 to provide a bias potential to an analyte sensor upon sensor insertion.

The battery 1406 can be configured to begin providing the bias potential upon insertion of the analyte sensor into the host's skin. FIG. 15 is a flowchart showing one example of a process flow 1500 that can be executed using the sensor mounting unit 1402 and battery 1406 to provide a bias potential to an analyte sensor upon sensor insertion. At operation 1502, the sensor mounting unit 1402 and/or battery 1406 detect that the analyte sensor has been inserted under the skin of the patient. At operation 1504, the battery 1406 applies the bias potential to the analyte sensor.

Operations 1502 and 1504 can be accomplished in any suitable manner. In some examples, the sensor mounting unit 1402 and/or battery 1406 comprises a switched control circuit including a sensor that is coupled to the contacts 1428. When the analyte sensor is inserted into the host, it may cause a change in the potential between the working electrode of the analyte sensor and the reference electrode of the analyte sensor. The change in potential may also be apparent across the contacts 1428. The sensor may detect the change in potential across the contacts 1428 (operation 1502). In response, the control circuit connects the battery 1406 to apply the bias potential (operation 1504) thereafter. Also, in some examples, the sensor mounting unit 1402 and/or battery 1406 includes a switched control circuit including a sensor that is positioned to determine when the mounting unit 1402 (and/or an adhesive pad thereof) is in contact with skin, indicating sensor insertion. When the sensor indicates contact with skin (operation 1502), the control circuit connects the battery to apply the bias potential (operation 1504) thereafter.

In another example, the sensor mounting unit 1402, contact assembly 1426 and contacts 1428 are configured in a manner similar to that shown above with respect to FIGS. 10A-10D. For example, the battery 1406 may be electrically coupled to the contacts 1428 prior to sensor insertion. As shown and described with respect to FIGS. 10A-10D, however, the analyte sensor may not be electrically coupled to the contacts 1428 until after insertion. Accordingly, before sensor insertion, the contacts 1428 are an open circuit. After sensor insertion, the working and reference electrodes are electrically coupled to the contacts 1428. This completes the circuit causing the battery 1404 to apply the bias voltage to across the working electrode and reference electrode of the analyte sensor.

Referring back to FIG. 15, the electronics unit can be installed to the sensor mounting unit 1402 at operation 1506. The electronics unit can include an additional battery or other suitable power source (as described herein) to provide the bias voltage to the analyte sensor. In some examples, the battery 1406 is configured to be disconnected from the analyte sensor upon installation of the electronics unit at operation 1506. In other examples, the battery 1406 may continue to apply the bias potential to the analyte sensor after installation of the electronics unit, for example, until the battery 1406 is discharged. For example, the electronics unit may include a regulator circuit to regulate the bias voltage applied to the analyte sensor by the battery or other power supply at the electronics unit. The regulator circuit may regulate the combination of the battery 1406 and electronics unit power supply to apply a desired bias potential to the analyte sensor as the battery 1406 discharges. After the battery 1406 discharges, the bias potential is provided by the electronics unit power supply.

In some examples, break-in is accelerated by applying a treatment to the host tissue at or near the insertion of the analyte sensor. In some examples, the treatment can include warming the tissue. For example, as the temperature of the tissue increases, transport processes in the tissue increase. Increased transport speed in the tissue may, in turn, cause the non-analyte electrochemical reactions at the analyte sensor to increase, thus shortening the electrochemical break-in. Increased transport speed in the tissue may also increase the rate at which interstitial or other bodily fluids contact the analyte sensor membrane, thus increasing the rate of membrane hydration and reducing membrane break-in. In some examples and under some conditions, an increase in tissue temperature of about 10 degrees Centigrade causes the speed of the processes causing electrochemical break-in and membrane break-in can to increased by a factor of two.

Figure 16:
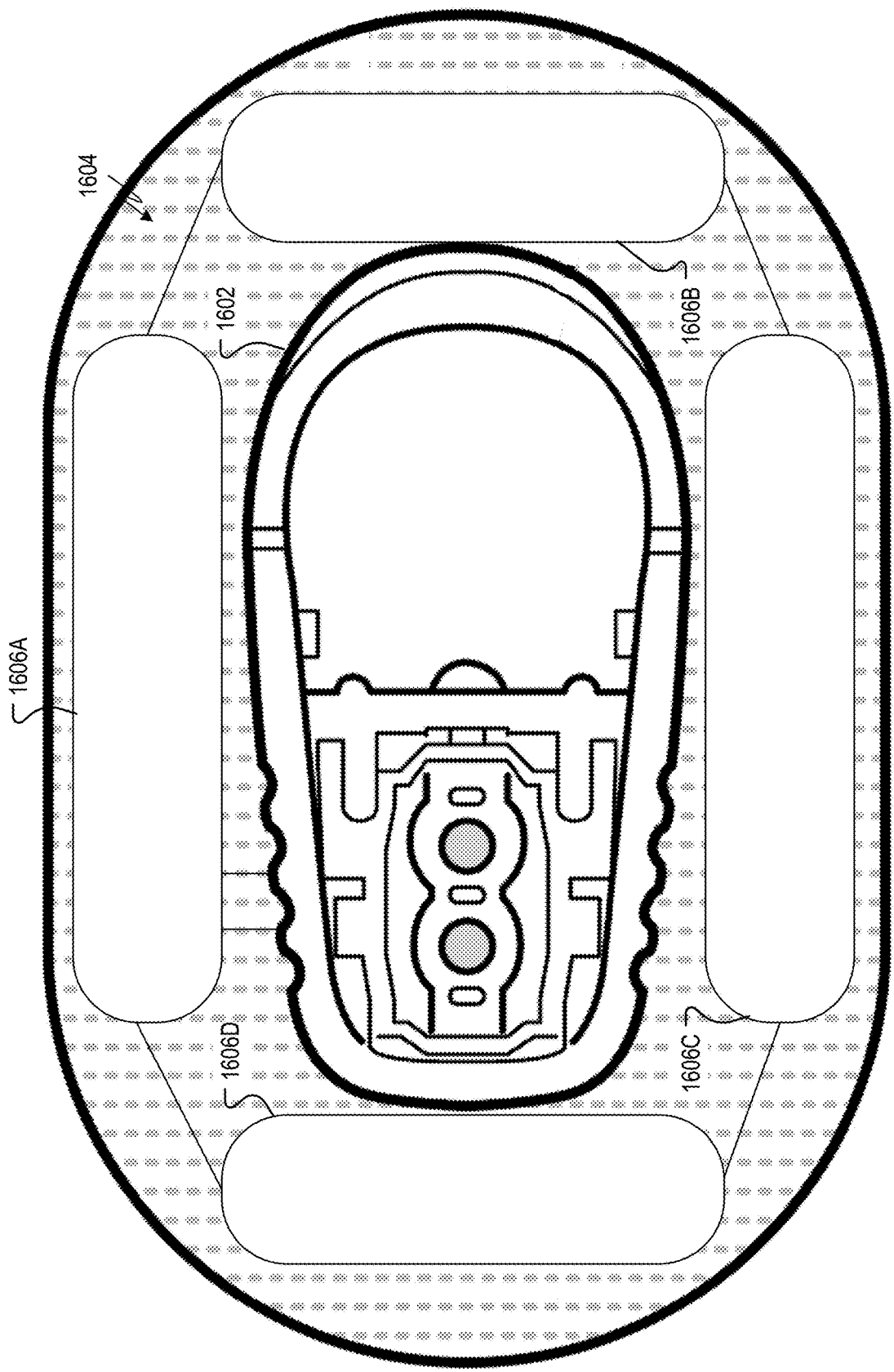
FIG. 16 is a diagram showing one example of a sensor mounting unit configured with heating elements to heat tissue at or near the sensor insertion.

FIG. 16 is a diagram showing one example of a sensor mounting unit 1602 configured with heating elements 1606A, 1606B, 1606C, 1606D to heat tissue at or near the sensor insertion. In the example of FIG. 16, the heating elements 1606A, 1606B, 1606C, 1606D are positioned on an adhesive pad 1604. FIG. 16 shows just one example arrangement of the heating elements 1606A, 1606B, 1606C, 1606D. Other arrangements have more or fewer elements of various shapes and having various positions are also contemplated.

The heating elements 1606A, 1606B, 1606C, 1606D generate heat that is applied to the surface of the host's skin, for example, from the underside of the adhesive pad 1604. Any suitable heat generating mechanism can be used. In some examples, the heating elements 1606A, 1606B, 1606C, 1606D include electrically resistive material. For example, one or more of the heating elements 1606A, 1606B, 1606C, 1606D may include electrically resistive wires that can be adhered to and/or woven into the adhesive pad 1604. The electrically resistive material is coupled to a battery or other power supply at the sensor mounting unit 1602 and/or at an electronics unit (not shown in FIG. 16). The power supply biases the resistive material, causing it to generate heat. In some examples, the power supply is associated with a control circuit that biases the electrically resistive material for a predetermined amount of time after sensor insertion and/or the installation of the electronics unit. The predetermined amount of time, for example, can correspond to break-in.

In some examples, the heating elements 1606A, 1606B, 1606C, 1606D utilize a chemical mechanism for generating heat. For example, heating elements 1606A, 1606B, 1606C, 1606D can include one or more reactants that react to generate heat when exposed to air. For example, the sensor mounting unit 1602 may not be exposed to air while in its packaging, for example, as shown in FIG. 13. When the sensor mounting unit 1602 is removed from its packaging for sensor insertion, the one or more reactants at the heating elements 1606A, 1606B, 1606C, 1606D may be exposed to air, causing the heating reaction. In some examples, the adhesive pad 1604, in some examples, is made of a porous or otherwise breathable material to permit the chemical reactants to have continued exposure to air after the adhesive pad 1604 is applied to the skin of the hose. In some examples, the chemical components can be selected to cause a heat-generating oxidation reaction when the heating elements 1606A, 1606B, 1606C, 1606D are exposed to air. Also, in some examples, one or more reactants for causing the heating reaction are infused into the adhesive pad 1604.

In some examples, treatment applied to the host's skin at or near the insertion can include applying a permeability enhancing substance. A permeability-enhancing substance is a substance that enhances the permeability of the host tissue to increase the flow of fluids and other materials into and out of the insertion point. This may accelerate the electrochemical reactions associated with break-in, thereby accelerating break-in. In some examples, the permeability-enhancing substance is infused into the adhesive pad 1604. The application of a permeability-enhancing substance can occur in addition to or instead of the application of heat by heating elements 1606A, 1606B, 1606C, 1606D. Permeability-enhancing substances can include substances used to reversibly reduce barrier resistance in tissues such as, for examples, sulphoxides, Azones, pyrrolidones (e.g., 2-pyrrolidone, 2P), alcohols and alkanols (ethanol or decanoyl), gycols (e.g., propylene glycol, PG), surfactants, and terpenes.

Figure 17:
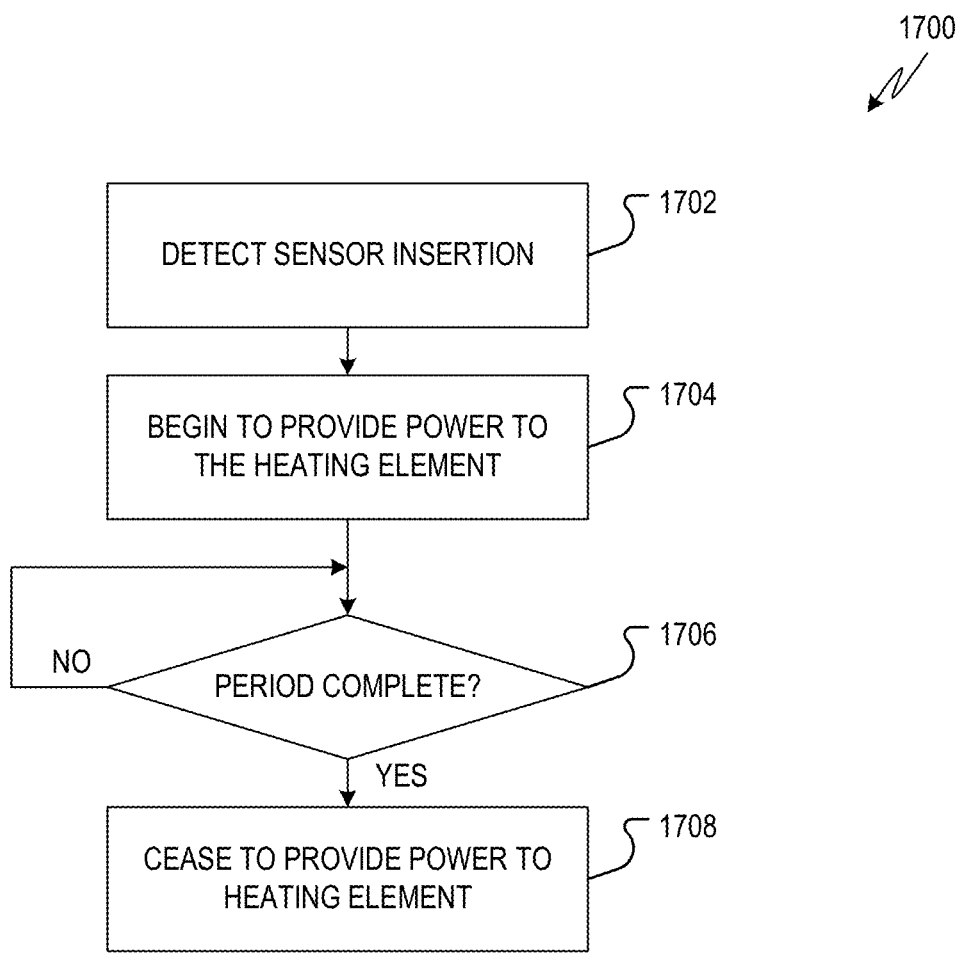
FIG. 17 shows one example of a process flow that can be executed by analyte sensor system, for example, to operate heating elements in examples where the heating elements are powered by sensor electronics.

FIG. 17 shows one example of a process flow 1700 that can be executed by analyte sensor system, for example, to operate heating elements 1606A, 1606B, 1606C, 1606D in examples where the heating elements 1606A, 1606B, 1606C, 1606D are powered by sensor electronics, such as sensor electronics 106. At operation 1702, the sensor electronics detect sensor insertion. This can be done in several suitable ways. For example, when the sensor electronics are included as part of a discrete sensor electronics unit, such as electronics unit 318, the analyte sensor system may detect sensor insertion and begin applying heat when the sensor electronics unit is installed to the sensor mounting unit.

In some examples, described herein with respect to FIGS. 10A-10D, the analyte sensor is not coupled to contacts such as 928 prior to insertion. As described, coupling of the analyte sensor to the contacts occurs during sensor insertion. Accordingly, in some examples, the sensor electronics can detect sensor insertion by monitoring the contacts, such as contacts 928, and detecting that the analyte sensor is coupled to the contacts. For example, before sensor insertion, the contacts are an open circuit. After sensor insertion, the working and reference electrodes of the analyte sensor are electrically coupled to the contacts. This completes the circuit between the contacts and may, for example, lead to a difference in voltage across the contacts, a difference in the perceived resistance between the contacts, or other difference in the electrical properties of the contacts that can be detected. In another example, the sensor mounting unit 1602 can include a sensor that detects contact and/or proximity to skin. Sensor insertion can be detected when contact and/or proximity to skin is detected.

Upon detecting the sensor insertion, the sensor electronics begins to provide power to one or more heating elements 1606A, 1606B, 1606C, 1606D at operation 1704. Upon being provided with power, the heating elements 1606A, 1606B, 1606C, 1606D begin to generate heat that is transmitted to the skin and/or other tissue of the host at or near the sensor insertion site. The sensor electronics may continue to provide power to the heating elements 1606A, 1606B, 1606C, 1606D for a defined time period. The time period may be an expected duration of the break-in. At operation 1706, the sensor electronics determine whether the period is complete. If not, the sensor electronics may continue to provide power to the heating elements 1606A, 1606B, 1606C, 1606D and return again to operation 1706. If, at operation 1706, the sensor electronics determines that the period is complete, it ceases to provide power to the heating elements 1606A, 1606B, 1606C, 1606D at operation 1708.

In some examples, instead of powering the heating elements 1606A, 1606B, 1606C, 1606D for a predefined period, the sensor electronics are configured to power the heating elements until break-in is complete. For example, the sensor electronics may determine whether the response of the analyte sensor is substantially linear. When the response of the analyte sensor is substantially linear, the sensor electronics ceases to provide power to the heating elements 1606A, 1606B, 1606C, 1606D.

In some examples, break-in is accelerated by applying an overpotential bias to the analyte sensor, for example, initially after the analyte sensor is inserted into the host. An overpotential bias is a bias potential that is higher than an operating bias potential of the analyte sensor. Applying an overpotential bias may accelerate the electrochemical reactions that occur during break-in, thus accelerating and potentially shortening break-in.

In some examples, the overpotential bias is provided as a series of overpotential pulses. For example, sensor electronics, such as sensor electronics 106 of FIGS. 1 and 2, can alternately provide a baseline bias potential and a pulse bias potential. The baseline bias potential may be less than, greater than, or, in some examples, about equal to the operating bias potential of the analyte sensor. The pulse bias potential is greater than the operating bias potential of the analyte sensor. In some examples, the pulse bias potential is between about 5% and 100% higher than the baseline bias potential. In some examples, the pulse bias potential is between about 10% and 75% higher than the baseline bias potential. In some examples, the pulse bias potential is between about 15% and 50% higher than the baseline bias potential. In some examples, the pulse bias potential is about 25% higher than baseline bias potential.

In some examples, the duration of the pulses and the interval between pulses is equal. For example, the pulse bias potential can be provided for a pulse-on period. At the end of the pulse-on period, the baseline bias potential is applied for a pulse-off period. At the end of the pulse-off period, the pulse bias potential is again applied, and so on. An overpotential bias pattern can begin with a pulse-on period or with a pulse-off period. In some example, an initial pulse-on and pulse-off period can be shorter than subsequent pulse-on and pulse-off periods.

Figure 18:
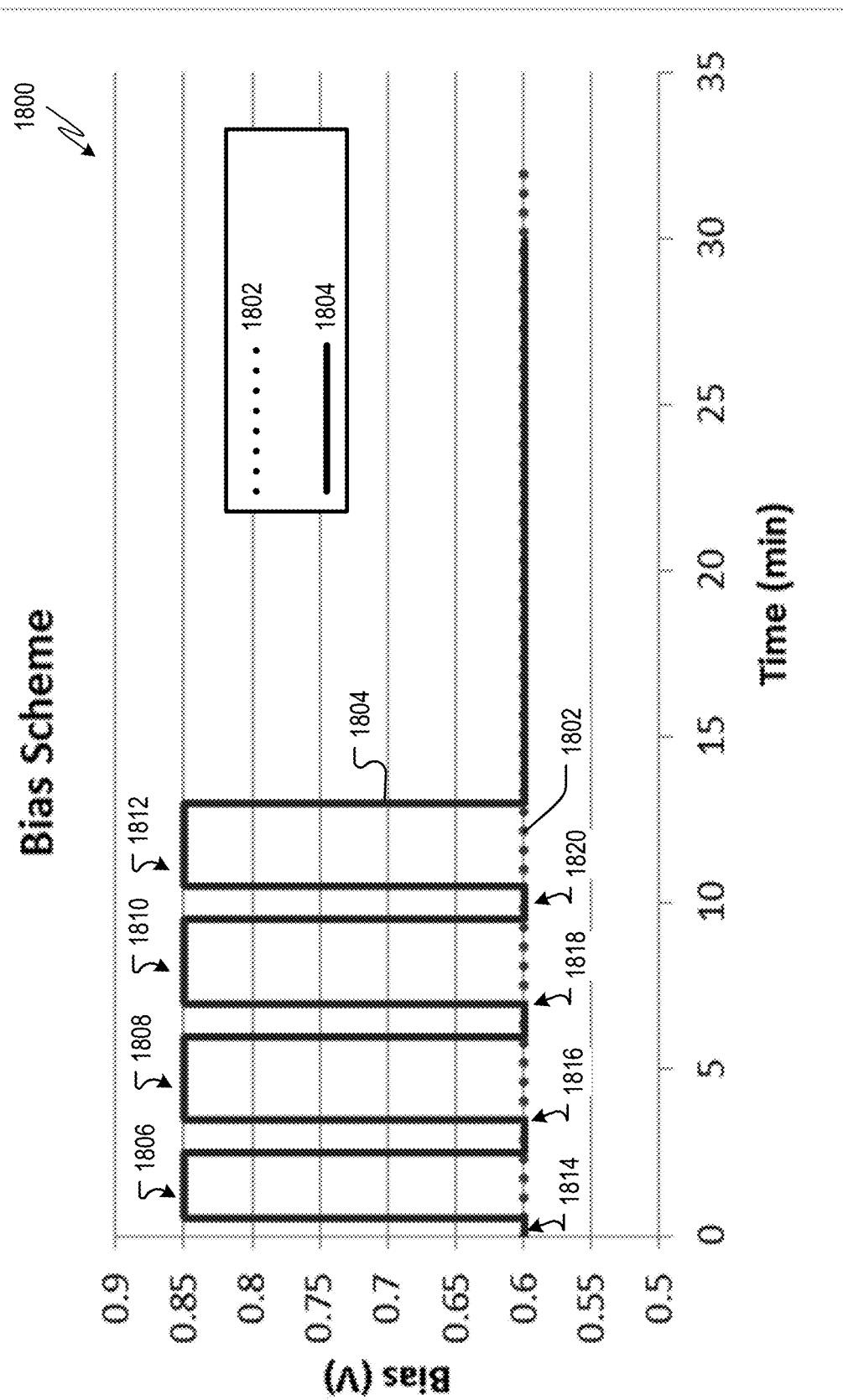

FIG. 18 is a diagram 1800 showing one example of a pulsed overpotential bias that can be provided to analyte sensor in some examples to accelerate break-in. In FIG. 18, a horizontal or x-axis shows time in minutes. Zero time indicates the beginning of a sensor session (e.g., the time at which bias potential is first applied to the analyte sensor). A vertical or y-axis shows the bias potential in volts (V). Two plots 1802, 1804 is shown. The plot 1802 shows a constant bias potential at 600 mV, which is the operating bias potential of the analyte sensor in this example. The plot 1804 shows a pulsed overpotential bias having a baseline bias potential of 600 mV and a pulse bias potential of 850 mV.

Four pulse-on periods 1806, 1808, 1810, 1812 are shown along with four pulse-off periods 1814, 1816, 1818, 1820. The plot 1804 begins with a pulse-off period 1814. The potential and durations of the various periods 1806, 1808, 1810, 1812, 1812, 1814, 1816, 1818, 1820 is indicated in TABLE 1 below:

TABLE 1

| Potential Bias (mV) | | | | | | | |
|---|---|---|---|---|---|---|---|
| 600 | 850 | 600 | 850 | 600 | 850 | 600 | 850 |

| Duration (s) | 30 | 120 | 60 | 150 | 60 | 150 | 60 | 150 |

As illustrated in FIG. 18 and shown in TABLE 1, the period of the initial pulse-off period 1814 is shorter than subsequent pulse-off periods 1816, 1818, 1820. Similarly, the period of the initial pulse-on period 1806 is shorter than subsequent pulse-on periods 1808, 1810, 1012.

Figure 19:
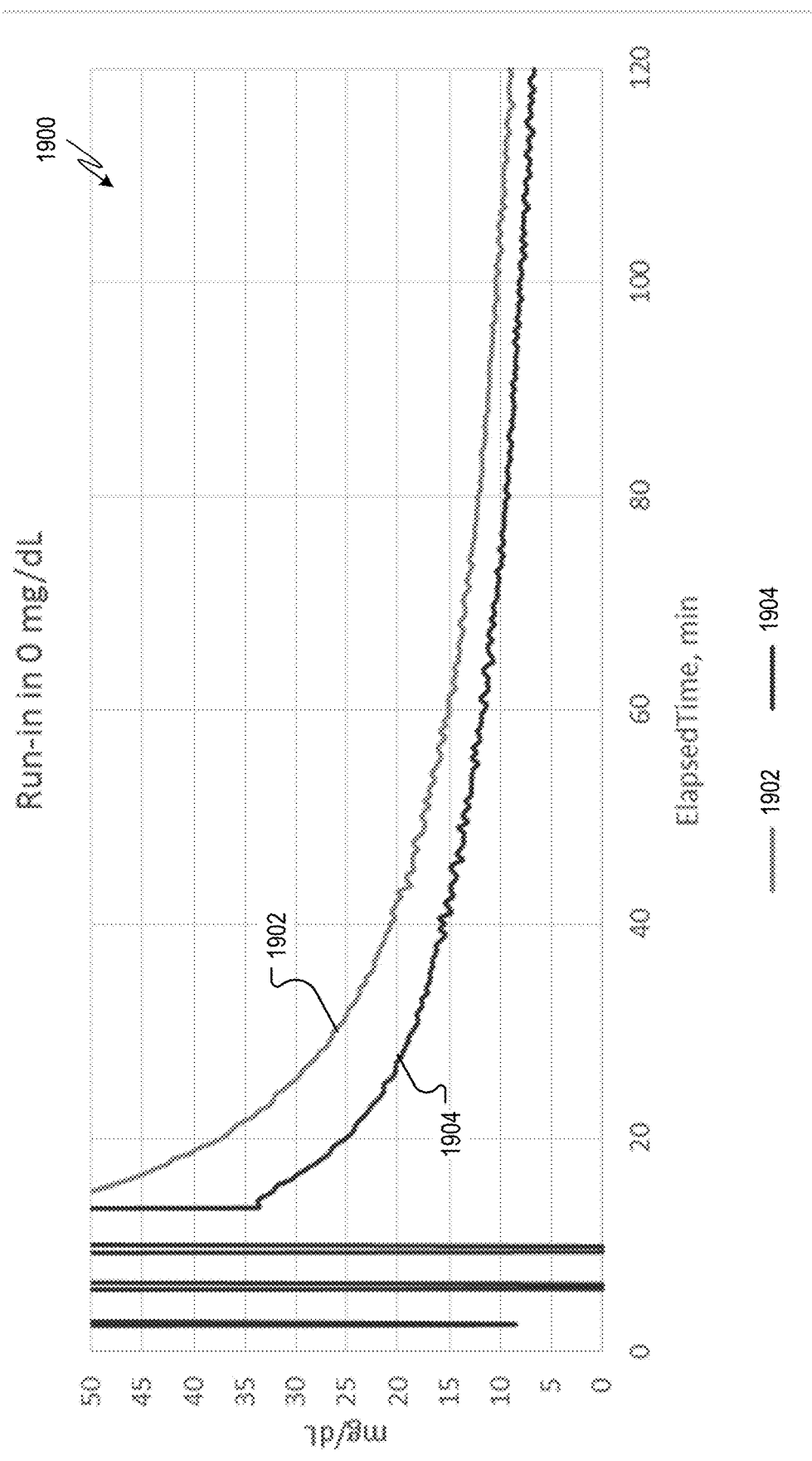
FIG. 19 is a diagram 1900 showing break-in curves obtained from an analyte sensor using the potential bias plots of FIG. 18.

FIG. 19 is a diagram 1900 showing break-in curves 1902, 1904 obtained from an analyte sensor using the potential bias plots 1802, 1804 of FIG. 18. In the diagram 1900, the horizontal or x-axis shows elapsed time since the bias potential was first applied, in minutes. The vertical or y-axis shows an uncompensated analyte concentration value derived from a raw sensor signal.

The break-in curve 1902 describes the response of the analyte sensor using the plot 1802 that applied a constant bias potential of 600 mV. The break-in curve 1904 describes the response of the analyte sensor using the plot 1804 with pulses as described by TABLE 1. As shown, after the pulses are applied, the response of the sensor indicated by break-in curve 1904 becomes linear sooner than the response of the sensor indicated by break-in curve 1902.

In addition to or instead of accelerating or shifting break-in to occur prior to sensor insertion, various examples described herein are directed to apparatuses, systems, and methods for modeling the response of an analyte sensor during breaking and using the modeled response to generate analyte concentration values from raw sensor signal data captured during break-in.

For example, an analyte sensor system may be configured to determine one or more break-in characteristics and apply the one or more break-in characteristics to generate analyte concentration values from raw sensor data during break-in. A break-in characteristic describes the response of an analyte sensor during break-in. An example break-in characteristic is a break-in intercept function indicating the change in the intercept of the analyte sensor with respect to time during break-in. An example representation of a break-in intercept function is provided by Equation [2] below:

$$\text{Intercept} = f_I(t) \quad [2]$$

In Equation [2], Intercept is the intercept of the analyte sensor response, for example, illustrated as intercept 706 in FIG. 7. $f_I(t)$ is the break-in intercept function describing the change in the intercept over the break-in. Another example break-in characteristic is a break-in sensitivity function indicating the change in the sensitivity of the analyte sensor over time during break-in. An example representation of a break-in sensitivity function is provided by Equation [3] below:

$$\text{Sensitivity} = f_S(t) \quad [3]$$

In Equation [3], Sensitivity is the sensitivity of the analyte sensor response, for example, illustrated as sensitivity 704 in FIG. 7. $f_S(t)$ is the break-in sensitivity function describing the change in the intercept over the break-in. The break-in intercept function and break-in sensitivity function indicate the changes to the intercept and sensitivity of the analyte sensor over break-in. In some examples, these functions collectively describe a break-in curve for an analyte sensor, such as the break-in curve 802 of FIG. 8.

When one or more break-in characteristics for an analyte sensor are known, an analyte sensor system can apply the one or more break-in characteristics to determine an analyte concentration value from the raw sensor signal generated during some or all of the sensor break-in. For example, the analyte sensor system may use a break-in sensitivity function and break-in intercept function to find a sensitivity and intercept for a particular time during break-in. The determined sensitivity and intercept can be used, for example using Equation [1] above, to convert a raw analyte sensor signal to a corresponding analyte concentration. In some examples, the break-in sensitivity function and/or break-in intercept function can be expressed as an equation and/or as a look-up table, as described herein.

Figure 20:
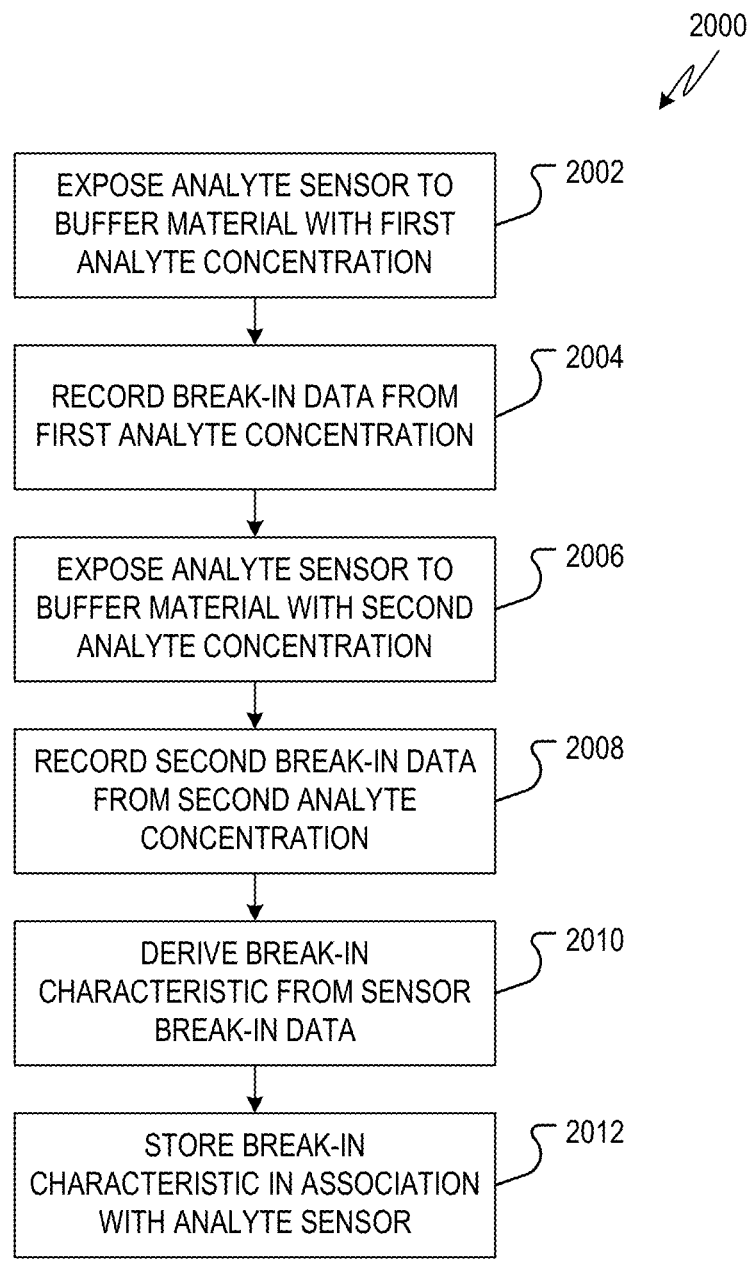
FIG. 20 is a flowchart showing one example of a process flow that can be executed, for example, during manufacture of an analyte sensor, to determine an analyte sensor break-in characteristic.

FIG. 20 is a flowchart showing one example of a process flow 2000 that can be executed, for example, during manufacture of an analyte sensor, to determine an analyte sensor break-in characteristic. The process flow 2000 may capture variations in sensor break-in characteristics that occur during an analyte sensor's construction such as, for example, variations in the elongated conductive body, variations in the membrane, etc.

At operation 2002, an analyte sensor is exposed to a first buffer material having a first concentration of analyte. The analyte sensor may be hydrated prior to exposure to the buffer material and/or may hydrate in the first buffer material. A bias potential is applied to the analyte sensor in the buffer material. In the first buffer material, the analyte sensor experiences electrochemical break-in and/or membrane break-in. The raw sensor signal of the analyte sensor may exhibit a break-in curve, for example, similar to the break-in curve 802 shown in FIG. 8. At operation 2004, break-in data from the first analyte concentration is recorded. The break-in data can include, for example, raw sensor signal values over the break-in period.

At operation 2006, the analyte sensor is exposed to a second buffer material having a second concentration of the analyte. Optionally, the analyte sensor is allowed to dry between being removed from the first buffer material and being exposed to the second buffer material. In this way, the analyte sensor goes through membrane break-in at both the first analyte concentration and at the second analyte concentration. At operation 2008 break-in data from the second analyte concentration is recorded.

At operation 2010, one or more break-in characteristics for the analyte sensor are derived from the sensor break-in data recorded at operation 2004 and 2008. The break-in characteristic can be derived in various ways. In some examples, the break-in curves exhibited by the analyte sensor are compared to a set of reference break-in curves exhibited by other analyte sensors that were previously tested. The analyte sensor may be assigned to a category or bucket based on which reference break-in curve best describes the break-in behavior of the analyte sensor as indicated by the measured break-in curve or curves. In some example, the category or bucket is associated with a break-in intercept function and/or a break-in sensitivity function. Analyte sensor assigned to the same category or bucket may use the same break-in intercept function and/or break-in sensitivity function.

In some examples, the break-in data recorded at operations 2004 and 2008 is used to derive a break-in intercept function and/or a break-in sensitivity function. for the analyte sensor. For example, the break-in curve exhibited by the analyte sensor at the first concentration can be compared to the break-in curve exhibited by the analyte sensor at the second concentration. Differences between the raw sensor signals at the same time since the beginning of the break-in but at different analyte concentrations can be used to derive the break-in intercept function and/or a break-in sensitivity function.

For example, raw sensor signals captured at the same time after application of the potential bias can be matched. Consider a first raw sensor signal from the first analyte concentration at a first time t1 after application of the potential bias and a second raw sensor signal from the second analyte concentration at the first time t1. From these raw sensor signals, a sensitivity and intercept for the analyte sensor at the first time t1 can be determined. (In some examples, operations similar to 2002 and 2004 can be repeated at additional analyte concentrations to provide additional raw sensor signal data at each time.) The observed sensitivity and intercept can be determined in a similar way across additional times t to derive values for the analyte sensors sensitivity and intercept over time during the break-in period. The values for sensitivity and intensity over time indicate the break-in sensitivity function and the break-in intercept function. In some examples, functions, such as $f_I(t)$ and/or $f_S(t)$ can be derived from the data. In other examples, the data can be used to construct a look-up table that can be used, for example, by sensor electronics to determine time-dependent values for sensor intercept and sensitivity during break-in.

The operation 2010 can be performed, in some examples, by a computing device. For example, operations 2004 and 2008 may include recording the respective break-in data to a machine-readable medium. In some examples, the machine-readable medium is a memory association with sensor electronics for the analyte sensor, such as sensor electronics 106 and memory 208 of FIG. 2. Accordingly, operation 2010 may be performed by the sensor electronics 106. In another example, the medium is accessible by a remote computing device such as, for example, the general purpose computer 118, peripheral medical device 122, handheld smart device 112, tablet 114, the server system 126, etc. The remote computing device may derive the one or more break-in characteristics.

At operation 2012, the break-in characteristic derived at operation 2010 is stored in association with the analyte sensor. In some examples, an indicator of the break-in characteristic is encoded onto the analyte sensor itself, a mounting unit coupled to the analyte sensor, packaging associated with the analyte sensor, etc. The indicator, in some examples, is or includes a code (e.g., alphanumeric code) that is printed, inscribed, or otherwise recorded on analyte sensor packaging. The host or other user can provide the code to a computing device when the sensor is inserted, allowing the computing device to utilize the code derive analyte concentration values during break-in. In some examples, one or more break-in characteristics associated with the analyte sensor are stored at a remote computing device, such as the server system 126, in associated with the indicator. The host or other user provides the code to the computing device when the sensor is inserted. The computing device is programmed to provide the code to the server system 126. In response, the server system 126 provides one or more break-in characteristics associated with the analyte sensor such as, for example, functions $f_I(t)$ and/or $f_S(t)$.

In the example process flow 2000, the analyte sensor is exposed to two different buffer materials having two different analyte concentrations. In some variations, the number of buffer materials and analyte concentrations to which the analyte sensor is exposed can be varied. For example, operations 2006 and 2008 may be omitted and the analyte sensor can be exposed to a single analyte concentration. Also, in some examples, the analyte sensor can be exposed to more than two different analyte concentrations. For example, operations 2002 and 2004 can be repeated for one or more additional analyte concentrations. In some examples, the analyte sensor is exposed to four different analyte concentrations.

Also, in some examples, the process flow 2000 is executed in conjunction with a calibration check process for characterizing the intercept and/or sensitivity of an analyte sensor after break-in. For example, the analyte sensor may remain in the respective buffer materials after break-in occurs to collect calibration data used to characterize the response of the analyte sensor after break-in.

In some examples, break-in characteristics for an analyte sensor can be derived from use data describing sensor break-ins that occur in vivo. For example, a number of analyte sensor systems used by multiple different hosts can be in communication with a single server system, such as the server system 126 of FIG. 1. The analyte sensor systems transmit to the server system raw sensor data captured during analyte sensor break-ins and indicating break-in curves at the various analyte sensor systems used by the various hosts. The sever system 126 uses the raw sensor data to generate break-in characteristics for the analyte sensor systems that can be used, as described herein, to generate analyte concentration values from the analyte sensor systems during break-in.

Figure 21:
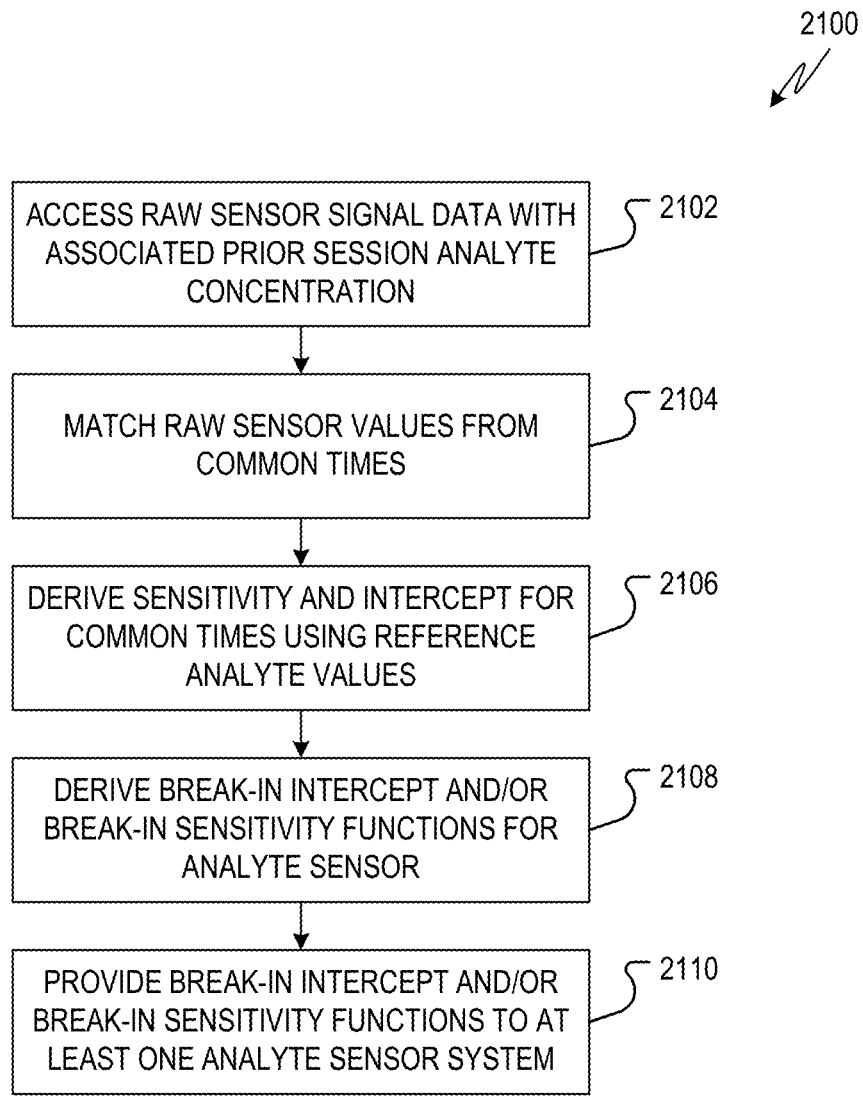
FIG. 21 is a flowchart showing one example of a process flow that can be executed to determine an analyte sensor break-in characteristic using inter-host data collected from different hosts.

FIG. 21 is a flowchart showing one example of a process flow 2100 that can be executed to determine an analyte sensor break-in characteristic using inter-host data collected from different hosts. The process flow 2100 can be executed by a computing device, such as the server system 126 of FIG. 1. At operation 2102, the computing device accesses raw sensor signal data. The raw sensor signal data includes a plurality of break-in curve sets. Each break-in curve set includes raw sensor signal data describing a break-in at an analyte sensor system used by a host. Each break-in curve set also includes a reference analyte concentration. The reference analyte concentration can be, for example, a last analyte concentration value from a previous sensor session before the break-in. The raw sensor signal data can include break-in curve sets from multiple different hosts using multiple different analyte sensors.

In some examples, a single reference analyte concentration describes more than one break-in curve set. For example, a reference analyte concentration that is an average over the population of hosts and analyte sensors described by the break-in curve set can be applied to more than one break-in curve set. In some examples, the average can be an average over a particular time period. For example, an average of analyte concentrations during break-ins that take place between 10:00 a.m. and 5:00 a.m. may be used as a reference analyte concentration for break-in curve sets describing break-ins that occurred in that time range. An average of analyte concentrations during break-ins that take place between 5:00 a.m. and 12:00 p.m. may be used as a reference analyte concentration for break-in curve sets describing break-ins that occurred in that time range, and so on. The time periods provided herein are for the purpose of providing an example. In practice, different time periods can be used. In another example, the average can be an average over a hosts having common properties (e.g., hosts of the same age, hosts with the same kind of diabetes, etc.).

At operation 2104, the computing device matches raw sensor values from common times across the break-in curve sets. Times may be measured, for example, from the when the bias potential was first applied during each break-in. At operation 2106, the computing device determines sensitivity and intercepts for common times using the reference analyte concentrations. For example, the raw sensor signal data for each break-in curve set may be assumed to be at the reference analyte concentration. Operation 2106 may result in a sensitivity and intercept for each considered time.

At operation 2108, the computing device derives a break-in intercept function and/or break-in sensitivity function using the sensitivities and/or intercepts determined at operation 2106. The break-in intercept function and/or break-in sensitivity function can be expressed as an equation and/or as a look-up table. At operation 2110, the break-in intercept function and/or break-in sensitivity function derived at operation 2108 are provided to at least one analyte sensor system for use in determining analyte concentration values during break-in.

The process flow 2100 considers data across multiple hosts and multiple analyte sensor systems. In some examples, however, a particular host uses an analyte sensor system in host-specific ways that affect break-in characteristics. For example, a host may consistently place the analyte sensor in a particular anatomical location. Also, for example, a host may have particular physiological properties that affect break-in. Accordingly, in some examples, break-in characteristics can be determined using intra-host data (e.g., data gathered from a single host over multiple sensor sessions).

Figure 22:
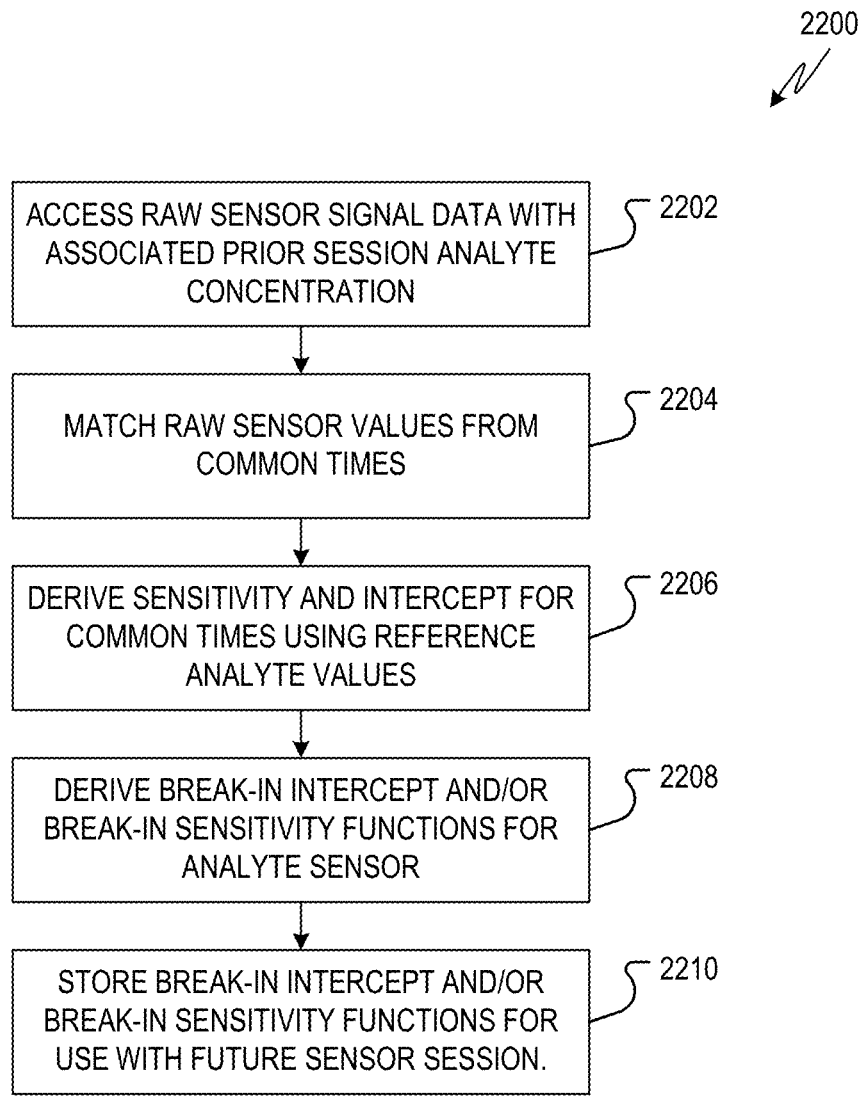
FIG. 22 is a flowchart showing one example of a process flow that can be executed in an analyte sensor system to determine an analyte sensor break-in characteristic considering intra-host data.

FIG. 22 is a flowchart showing one example of a process flow 2200 that can be executed in an analyte sensor system to determine an analyte sensor break-in characteristic considering intra-host data. The process flow 2200 can be executed by a computing device, such as the server system 126 of FIG. 1. In some examples, the process flow 2200 is executed locally at an analyte sensor system, for example, by the sensor electronics 106, the peripheral medical device 122, the smart device 112, the tablet 114, or similar computing device.

At operation 2202, the computing device accesses raw sensor signal data. The raw sensor signal data can include a plurality of break-in curve sets describing a first host. Each break-in curve set includes raw sensor data describing a break-in of an analyte sensor used by the host along with a reference analyte concentration. The reference analyte concentration can be, for example, the last analyte concentration value from a previous sensor session before the break-in described by the break-in curve set.

At operation 2204, the computing device matches raw sensor values from common times across the break-in curve sets. Times may be measured, for example, from the when the bias potential was first applied during each break-in. At operation 2206, the computing device determines sensitivity and intercepts for common times using the reference analyte concentrations. For example, the raw sensor signal data for each break-in curve set may be assumed to be at the reference analyte concentration. Operation 2206 may result in a sensitivity and intercept for each considered time.

At operation 2208, the computing device derives a break-in intercept function and/or break-in sensitivity function using the sensitivities and/or intercepts determined at operation 2106. The break-in intercept function and/or break-in sensitivity function can be expressed as an equation and/or as a look-up table. At operation 2210, the break-in intercept function and/or break-in sensitivity function derived at operation 2208 are stored for use with future sensor sessions involving the subject host. The break-in intercept function and/or break-in sensitivity function can be stored, for example, remotely at the server system 126 and/or locally, for example, at a memory 208 of the sensor electronics 106 (See FIGS. 1 and 2).

Figure 23:
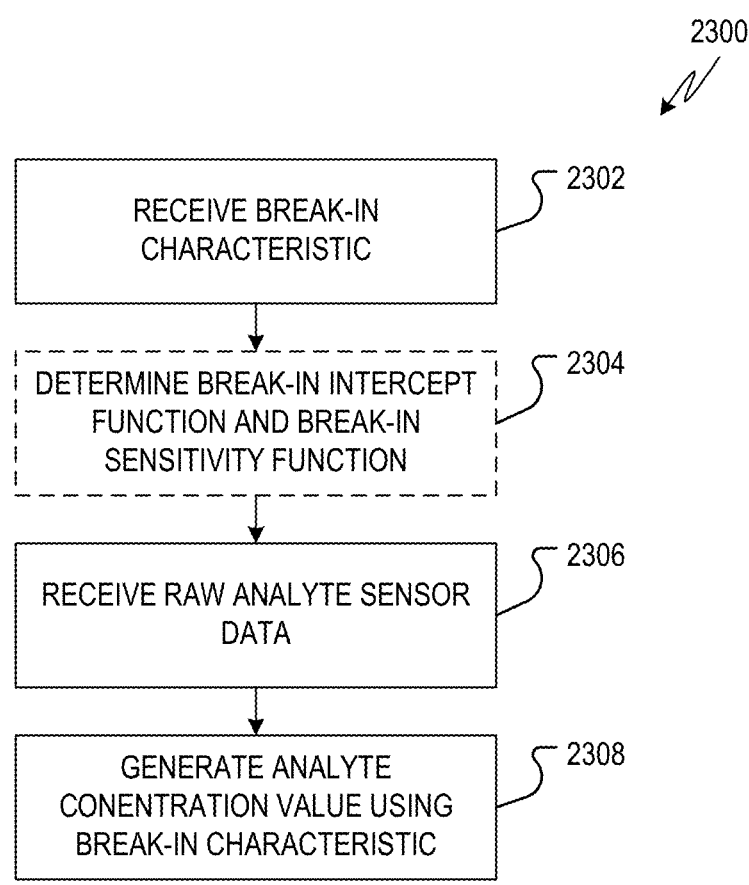

FIG. 23 is a flowchart showing one example of a process flow 2300 that can be executed at an analyte sensor system to generate analyte concentration values during break-in. The process flow can be executed by a computing device, such as the server system 126 of FIG. 1. In some examples, the process flow 2200 is executed locally at an analyte sensor system, for example, by the sensor electronics 106, the peripheral medical device 122, the smart device 112, the tablet 114, or similar computing device.

At operation 2302, the computing device receives a break-in characteristic. The break-in characteristic can include, for example, one or more look-up tables and/or equations describing the break-in intercept function. The break-in characteristic can also include, for example, one or more look-up tables and/or equations describing the break-in sensitivity function. In some examples, the computing device receives multiple examples of break-in intercept functions and/or break-in sensitivity functions. For example, the computing device may receive a break-in intercept and/or sensitivity function derived based on sensor manufacturing characteristics determined as described with respect to process flow 2000, break-in intercept and/or sensitivity functions derived based on inter-host data determined as described with respect to the process flow 2100 and/or break-in intercept and/or sensitivity functions derived using inter-host data determined, as described with respect to the process flow 2200. In some examples, break-in characteristics received at operation 2302 include an indication of a bucket or category into which an analyte sensor was categorized according to the process flow 2000.

At optional operation 2304, the computing device determines a break-in intercept function and a break-in sensitivity function that will be used to determine the analyte concentration value. In examples where a single break-in intercept function and a single break-in sensitivity function are derived, operation 2304 may be omitted. In some examples, in which a break-in characteristic received at operation 2302 includes a category or bucket associated with an analyte sensor, determining the break-in intercept function and/or break-in sensitivity function can include retrieving one or more such functions and/or querying the server system 126 to provide one or more such functions.

If multiple break-in sensitivity functions and/or break-in intercept functions are present, determining a break-in intercept function and break-in sensitivity function can include selecting preferred functions and/or aggregating the received functions. For example, when the functions are received in the form of look-up tables, the look-up tables can be averaged to generate an aggregated look-up table for break-in sensitivity and/or an aggregated look-up table for break-in intercept. The aggregation may be weighted. For example, functions based on intra-host data (if available) may be weighted higher than functions based on inter-host data.

At operation 2306, the computing device receives raw analyte sensor data captured during sensor break-in. The raw analyte sensor data can be accompanied by a time, such as a time since the bias potential was first applied. At operation 2308, the computing device uses the selected break-in sensitivity function and break-in intercept function to covert the raw analyte sensor data to an analyte concentration value. The analyte concentration value can be displayed, for example at a UI, such as the UI 252 of the peripheral device 250 of FIG. 2 and/or at the UI 272 of the medical device 270 also of FIG. 2.

In some examples, analyte concentration values generated during break-in using break-in characteristics as described herein may not have the same level of accuracy as analyte values determined after break-in. It may be desirable to display break-in analyte concentration values to the host or other user during break-in, but to also indicate to the host or other user that the host or other user should have less confidence in the accuracy of the displayed analyte concentration value than in analyte concentration values generated after break-in. In various examples, this is done by determining when an analyte value is based on raw sensor data from break-in and displaying that analyte concentration value at a UI with a confidence indicator. The confidence indicator indicates a level of confidence in the analyte concentration value.

In some examples, the confidence indicator is qualitative. For example, the presence or absence of the confidence indicator can indicate to the host or other user the level of confidence in the displayed analyte concentration values. In other examples, the confidence indicator is quantitative indicating a degree of confidence in the analyte concentration values. For example, analyte concentration values from raw sensor data captured early during break-in may be characterized by a lower confidence level than analyte concentration values from raw sensor data captured later during break-in when the analyte sensor response is closer to linear.

In some examples, a break-in model is determined using a non-enzyme sensor. A non-enzyme sensor is a sensor that is generated without an enzyme to react with analyte. As a result, a non-enzyme sensor will not generate raw sensor signal indicative of analyte, but will behave similarly to an analyte sensor during break-in. For example, because it lacks enzyme, a non-enzyme sensor will not exhibit electrochemical break-in, but will exhibit membrane break-in as its membrane becomes hydrates. In some examples, one or more non-enzyme sensors are used to generate break-in models.

In some examples, a break-in model is generated considering a break-in intercept function only. This can avoid inaccuracies that can be introduced by the break-in sensitivity model. For example, the break-in sensitivity curve $f_S(t)$ exhibited by many analyte sensors is often similar to a logarithmic function. Using a logarithmic function to model the break-in sensitivity, however, can be extremely sensitive to time variability, as the logarithm of zero is equal to negative infinity. Modeling break-in intercept only, however, can generate acceptable results.

Figure 31:
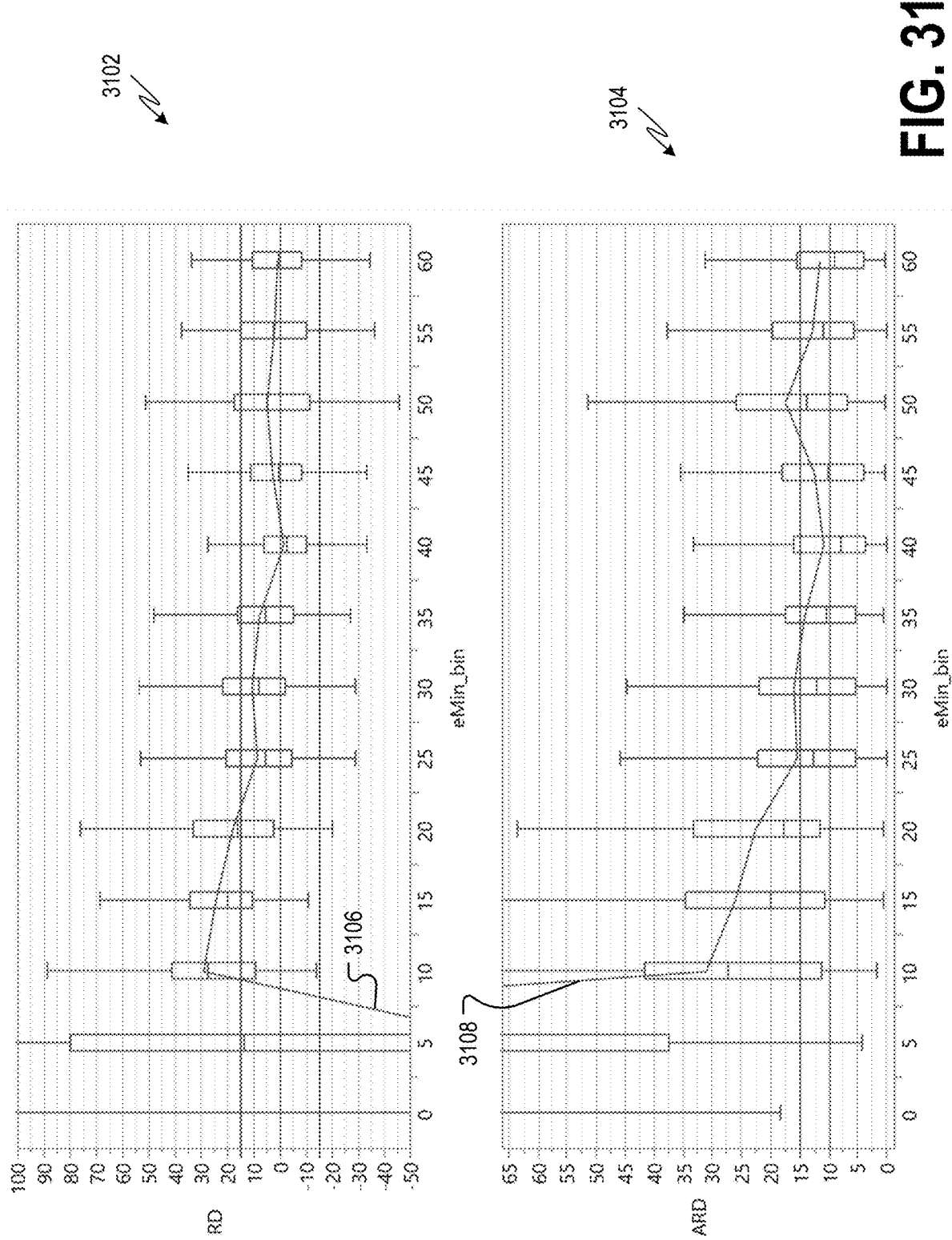

FIG. 31 is a diagram including two example plots 3102 and 3104 indicating errors of example analyte sensors during break-in. A relative difference plot 3102 indicates the relative difference between an analyte value generated by an analyte sensor relative to a reference sensor over the first hour after the analyte sensor is inserted. The relative difference is given by Equation [4] below:

$$D(x) = AV - Ref \qquad [4]$$

In Equation [4], $D(x)$ is the relative difference. AV is the analyte value generated by the analyte sensor and Ref is a reference analyte value generated by a reference sensor. In some examples, the analyte value is an estimated glucose value. The reference analyte value can be a glucose value measured using a single point glucometer, or other suitable sensor. An absolute relative difference plot 3104 shows the absolute value of the relative difference indicated by plot 3102. As demonstrated by the plots 3102 and 3104, the means 3106 and 3108 are quite high initially, settling below 35 mg/dL by about ten minutes and to less than 15 mg/dL by about twenty five minutes.

In some examples, the relative difference $D(x)$ can be expressed according to Equation [5] below:

$$D(x) = \frac{1}{\hat{m}}([m - \hat{m}] \times x + [b - \hat{b}]) \qquad [5]$$

In Equation [5], m indicates sensitivity and b indicates intercept. The value $\hat{m}$ indicates a modeled break-in sensitivity parameter while $\hat{b}$ indicates a modeled brake-in intercept parameter.

Figure 32:
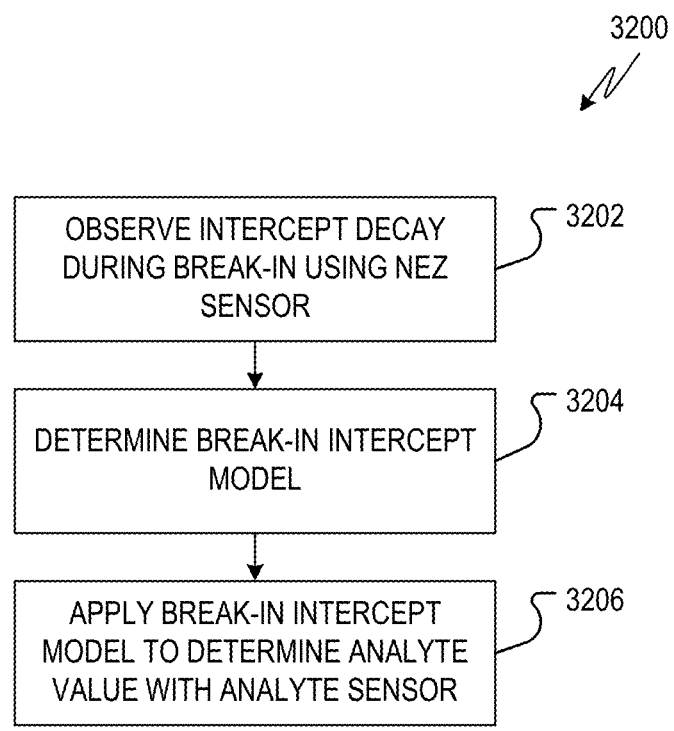
FIG. 32 is a flowchart showing one example of a process flow 3200 that can be executed in an analyte sensor system to determine an analyte sensor break-in characteristic considering intra-host data.

FIG. 32 is a flowchart showing one example of a process flow 3200 that can be executed in an analyte sensor system to determine an analyte sensor break-in characteristic considering intra-host data. The process flow 3200 can be executed by a computing device, such as the server system 126 of FIG. 1. In some examples, the process flow 2200 is executed locally at an analyte sensor system, for example, by the sensor electronics 106, the peripheral medical device 122, the smart device 112, the tablet 114, or similar computing device.

At operation 3202, the computing device determines intercept decay from non-enzyme sensor break-in data. The non-enzyme sensor break-in data is gathered from one or more non-enzyme sensors. The non-enzyme sensors are placed in a hydrating bath. The non-enzyme sensor break-in data can include raw sensor signals or other sensor signals generated by the non-enzyme sensors as they experience membrane break-in. At operation 3204, the non-enzyme sensor break-in data is used to generate a break-in intercept model (e.g., b from Equation [5] above). In some examples, the non-enzyme sensor break-in data used is limited to a fixed period after the non-enzyme sensor is introduced to the hydrating bath (e.g., within the first hour, within the first two hours, etc.).

An example form of the break-in intercept model is given by Equation [6] below:

$$\hat{b}(t) = a + bt^{-y} + ce^{-zt} \qquad [6]$$

The computing device may be programmed to generate values for a, b, c, y, and z that generate a curve that is a best fit to the non-enzyme sensor break-in data. At operation 3206, the computing device applies the break-in intercept model $\hat{b}(t)$ determined at operation 3204 at an analyte sensor to generate an analyte value.

Figure 33:
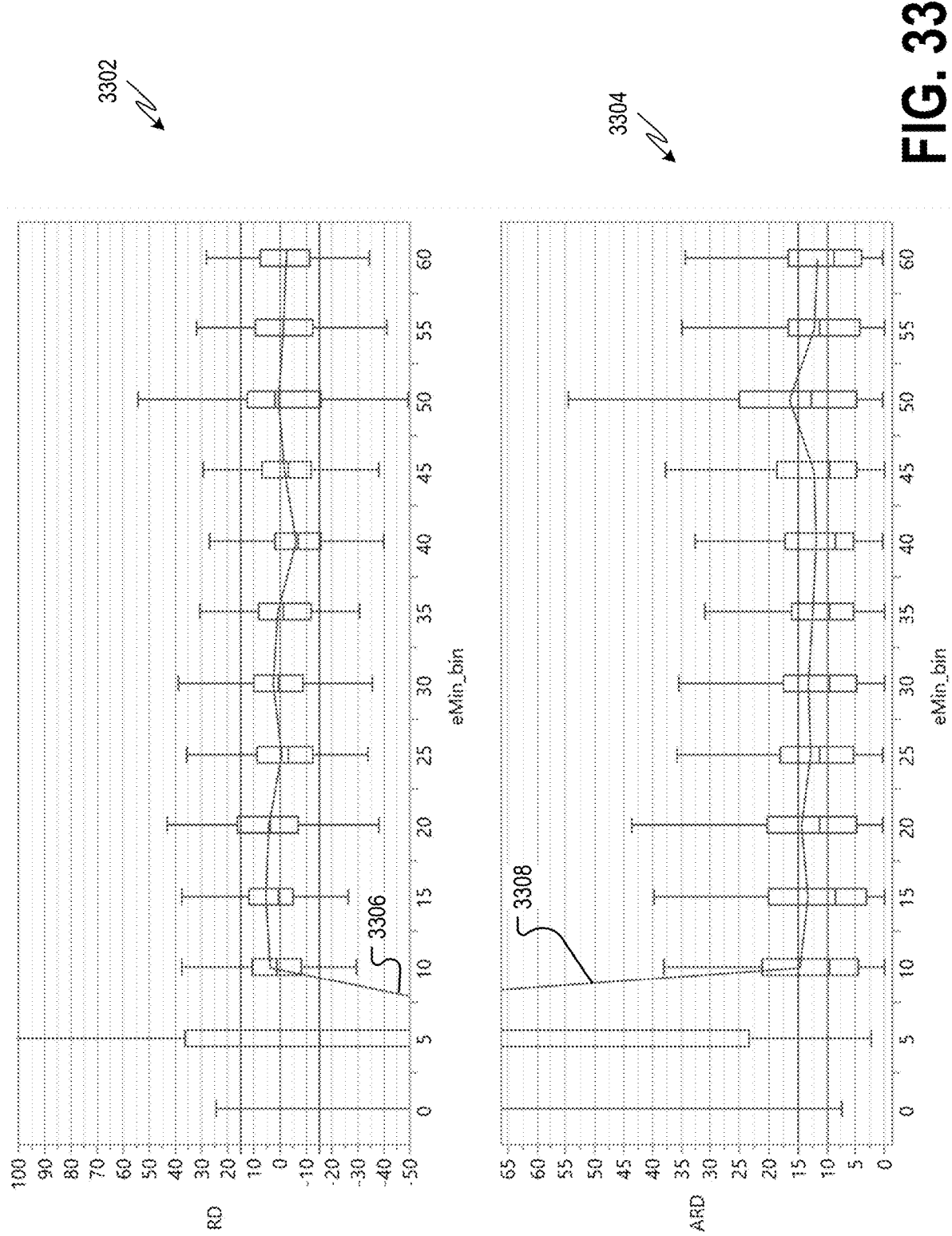
FIG. 33 is a diagram including two example plots indicating errors of example analyte sensors during break-in utilizing a break-in intercept model.

FIG. 33 is a diagram including two example plots 3302 and 3304 indicating errors of example analyte sensors during break-in utilizing a break-in intercept model determined, for example, as described with respect to the process flow 3200 of FIG. 32. A plot 3302 shows relative difference to a reference sensor while the plot 3304 shows an absolute relative difference to the reference sensor. As shown, both mean 3306 of the relative difference and the mean 3308 of the absolute relative difference were less than about 15 within about ten minutes.

Figure 34:
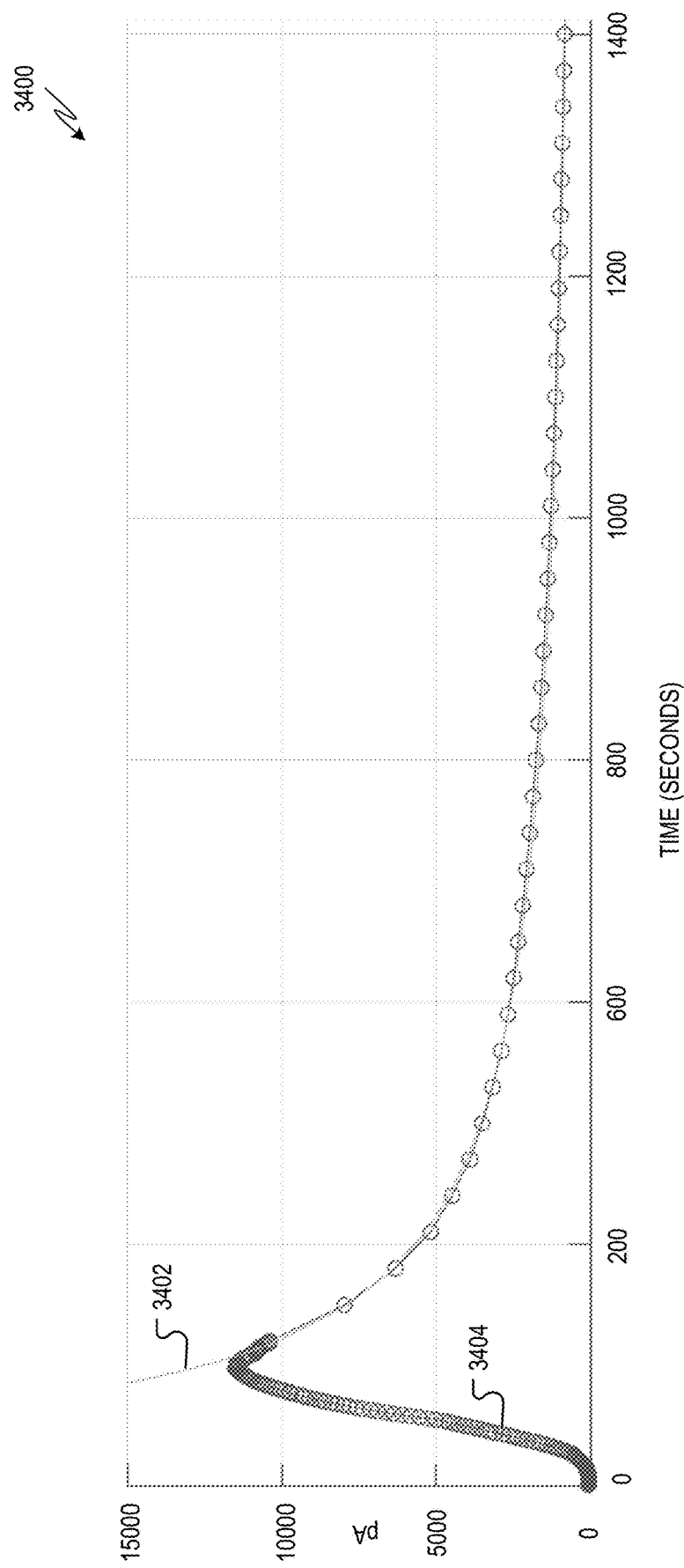
FIG. 34 is a diagram showing plots that illustrate the behavior of an analyte sensor and a non-enzyme sensor under constant bias conditions.

FIG. 34 is a diagram 3400 showing plots 3402 and 3404 illustrating the behavior of an analyte sensor and a non-enzyme sensor under constant bias conditions. The plots 3402 and 3404 indicate raw sensor signal (in picoamps) versus time (in seconds). A plot 3404 indicates the behavior of a non-enzyme sensor. In this example, the plot 3404 indicates the median behavior of a set of observed non-enzyme sensors. The plot 3402 indicates the behavior of an analyte sensor. As shown in FIG. 34, the behavior of the analyte sensor and non-enzyme sensor deviate prior to about 180 seconds. For example, electrochemical break-in at the analyte sensor initially causes a very high current. Because the non-enzyme sensor does not exhibit electrochemical break-in, the raw sensor signal from the non-enzyme sensor is initially quite low, building to match at about 180 seconds.

Figure 35:
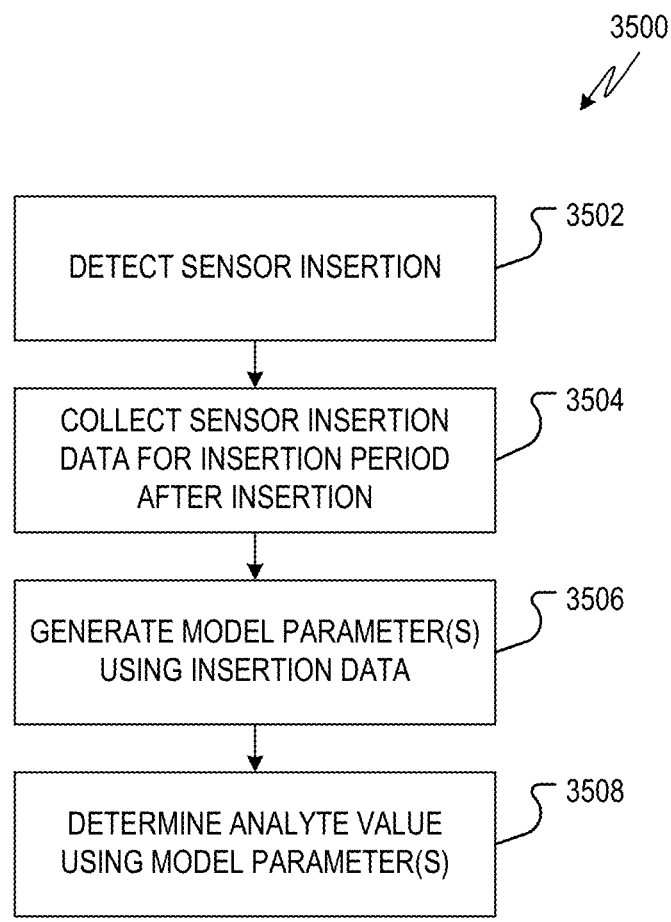
FIG. 35 is a flowchart showing one example of a process flow that may be executed by an analyte sensor system to generate and/or optimize a break-in model based on sensor insertion data.

In some examples, an analyte sensor may be operated to generate and/or optimize a break-in model based on sensor insertion data that includes raw sensor signal data sampled after insertion. FIG. 35 is a flowchart showing one example of a process flow 3500 that may be executed by an analyte sensor system to generate and/or optimize a break-in model based on sensor insertion data. At operation 3502, the analyte sensor system detects insertion of the analyte sensor under the skin of the patient. For example, the analyte sensor system may include a sensor insertion verification feature that detects when the sensor is inserted under the skin of the host. In some examples, the insertion verification feature is implemented utilizing one or more magnetic sensors, one or more proximity sensors, etc.

Upon detecting sensor insertion, the analyte sensor system collects sensor insertion data at operation 3502. The sensor insertion data includes samples of the raw sensor signal generated by the analyte sensor system. The sensor insertion data may be sampled at a suitable sampling frequency, such as, for example, between about ½ Hz and 5 Hz. In some examples, the insertion data is sampled at about 1 Hz. Insertion data is collected (e.g., at the sampling frequency) for an insertion time period. In some examples, the insertion time period is complete at or before the convergence of the behavior of the analyte sensor system with a non-enzyme sensor based break-in model (e.g., about 180 seconds in the example of FIG. 34).

At operation 3506, the analyte sensor system generates one or more model parameters using the insertion data. Model parameters from any suitable break-in mode may be used. An example model that may be used at operation 3506 is given by Equation [7] below:

$$O(t) = f(ECB1(t), MBI(t)) \qquad [7]$$

In Equation [7], O(t) is the observed break-in, which indicates the raw sensor signal (e.g., a current) during break-in.

ECBI(t) is the electrochemical break-in as a function of time. MBI(t) is the membrane break-in as a function of time. In Equation [7], the function $f$ can be any suitable combination of ECBI(t) and MBI(t) and can include, for example, a multiplication of ECBI(t) and MBI(t), a convolution of ECBI(t) and MBI(t), a nested integral of ECBI(t) and MBI(t), or any other suitable value.

The MBI(t), in some examples, is an increasing function over time and may be modeled as a value from 0% to 100%. Various different functions may have a shape that can be matched to MBI(t) including, for example, a cumulative density function (CDF) of a normal distribution, a CDF of a logistic distribution, a CDF of an exponential distribution, a CDF of a log-logistic distribution or other suitable distribution. The ECBI(t) is a decreasing function over time from infinity or another large real value to a constant value.

One example for ECBI(t) is given by Equation [8] below:

$$ECB1(t) = (a_0 + a_1 e^{-\lambda_1 t} + a_e e^{-\lambda_2 t} + a_3 + t^{-\lambda_3}) \quad [8]$$

One example for MBI(t) is given by Equation [9] below:

$$MBI(t) = 1 - \frac{1}{1 + \left(\frac{time}{\alpha}\right)^{-\beta}} \quad [9]$$

Accordingly, the resulting break-in model O(t) may be given by Equation [10] below:

$$O(t) = (a_0 + a_1 e^{-\lambda_1 t} + a_2 e^{-\lambda_2 t} + a_3 + t^{-\lambda_3}) \times 1 - \frac{1}{1 + \left(\frac{time}{\alpha}\right)^{-\beta}} \quad [9]$$

Using the example of Equations, [8], [9], and [10], the analyte sensor system utilizes the sensor insertion data to determine values for break-in model parameters $a_0$, $a_1$, $a_2$, $a_3$, $\alpha$, $\lambda_1$, $\lambda_2$, $\lambda_3$, and $\beta$. In some examples, initial values for break-in model parameters, such as $a_0$, $a_1$, $a_2$, $a_3$, $\alpha$, $\lambda_1$, $\lambda_2$, $\lambda_3$, and $\beta$, are based on non-enzyme sensor data as described herein. The initial values may be stored at the analyte sensor system. The analyte sensor system may modify or replace the initial values based on the sensor insertion data, as described herein. At operation 3508, the analyte sensor system utilizes the break-in model parameters determined at operation 3506 to determine an analyte value for the host. In some examples, the operation 3508 is performed after the sensor insertion period.

Figure 24:
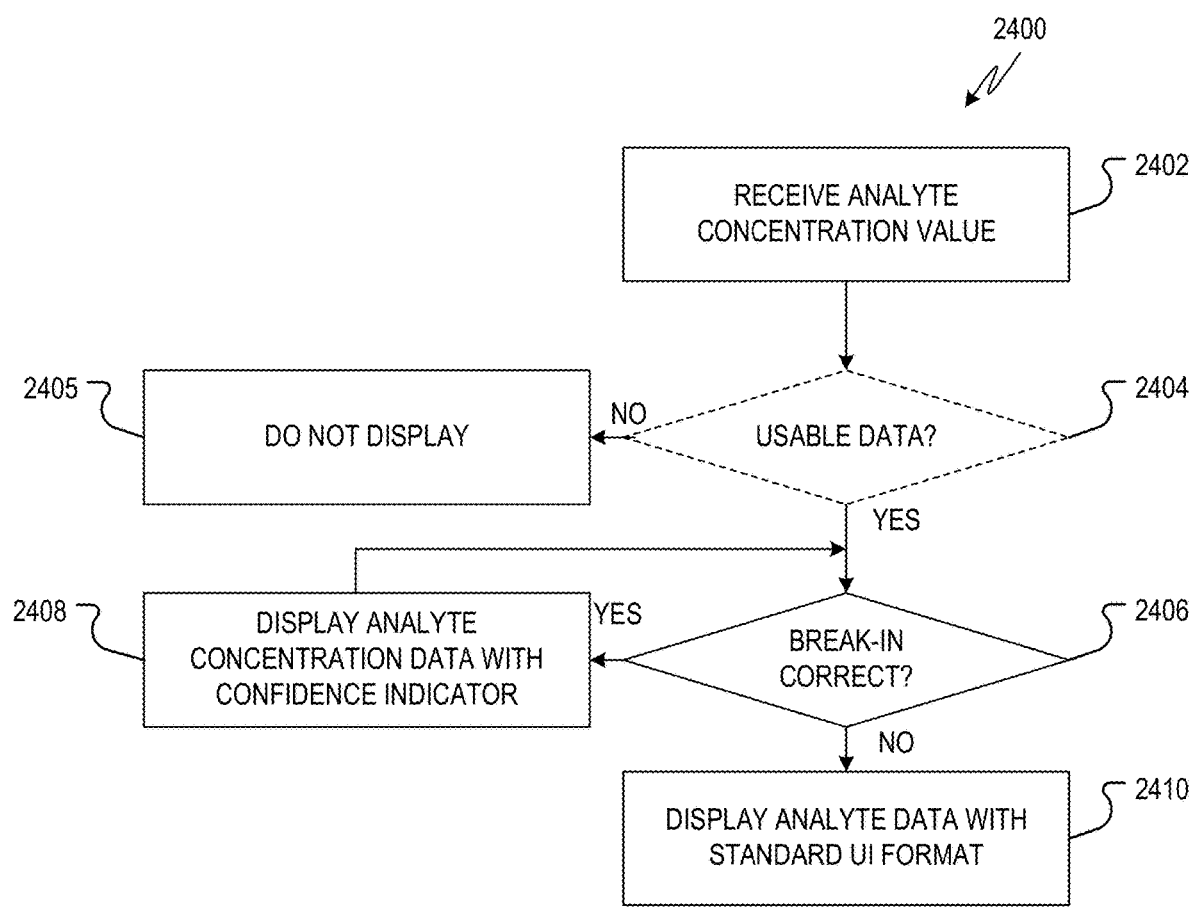
FIG. 24 is a flowchart showing one example of a process flow that can be executed by an analyte sensor system to display analyte concentration values to indicate confidence.

FIG. 24 is a flowchart showing one example of a process flow 2400 that can be executed by an analyte sensor system to display analyte concentration values to indicate confidence. The process flow 2400 can be executed by any suitable computing device associated with the analyte sensor system such as, for example, the sensor electronics 106, the peripheral medical device 122, the smart device 112, the tablet 114, or similar computing device.

At operation 2402, the computing device receives an analyte concentration value. At optional operation 2404, the computing device determines whether the analyte concentration value is usable. For example, analyte concentration values within a threshold time of the beginning of a sensor session (e.g., five minutes) may not be usable. If the analyte concentration value is not usable, the computing device does not display the analyte concentration value at operation 2405.

If the analyte concentration value is usable and/or if operation 2404 is omitted, the computing device determines at operation 2406 whether the analyte concentration value originates from raw sensor data captured during break-in. This can be determined in any suitable manner. In some examples, the computing device receives the analyte concentration value from sensor electronics, such as sensor electronics 106 in a way that includes an indication of whether the analyte concentration is based on sensor data captured during break-in. In another example, the computing device can compare a time stamp associated with the analyte concentration value to a time when the current sensor session began. If time stamp is within a threshold value of the beginning of the current sensor session, the computing device determines that the analyte concentration is based on raw sensor signal data captured during break-in.

If the analyte concentration value does originate from raw sensor data captured during break-in, the computing device displays the analyte concentration data at a UI with a confidence indicator at operation 2408. The confidence indicator indicates qualitatively or quantitatively that the host or other user should have less confidence in the displayed analyte concentration. In an example in which the analyte is glucose, the confidence indicator may indicate that the host or other user should not dose insulin using the displayed analyte (e.g., glucose) concentration value. In some examples, the confidence indicator indicates differing levels of confidence, for example, based on when the analyte concentration value is taken during break-in.

If the analyte concentration value is based on raw sensor signals captured after break-in, then the computing device displays the analyte concentration value in a standard UI format at operation 2410. In some examples, the standard UI format omits the confidence indicator. In other examples, the standard UI format includes the confidence indicator, but displays the confidence indicator in a manner that shows a higher level of confidence than for analyte concentration values based on raw sensor signal data from break-in.

FIGS. 25-28 show example UI screens showing example confidence indicators and associated analyte concentration values. FIG. 25 shows a progression between two UI screens 2502A, 2502B showing increasing confidence in a displayed analyte concentration values. For example, the UI screen 2502A displays analyte concentration values having a first level of confidence. The UI screen 2502B displays analyte concentration values have a second level of confidence higher than that associated with the UI screen 2502A.

The UI screen 2502A shows a shape 2504A with analyte value data displayed thereon. The shape 2504A has an area that indicates a level of confidence in the displayed analyte concentration value. The shape 2504A is one example of a quantitative confidence indicator. For example, as the level of confidence in the analyte concentration value increases, the UI screen 2502B may be displayed including a shape 2504B. The shape 2504B has a smaller area, indicating a lower level of uncertainty. In the example of FIG. 25, the shapes 2504A, 2504B also display a numerical range for the displayed analyte concentration values. Displaying a range of analyte concentration values instead of a single analyte concentration value, in some examples, is a confidence indicator.

The UI screens 2502A, 2502B also show a graph 2505A, 2505B including bounding curves 2506A, 2510A, 2506B, 2510B. Referring now to the UI screen 2502A, the bounded graph includes a plot 2508A indicating estimated analyte concentrations over time. Bounding curves 2506A, 2510A show a level of confidence in the displayed analyte concentration values. When the bounding curves 2506A, 2510A are farther from the plot 2508A, it indicates a lower level of confidence. On the other hand, referring to the UI screen 2502B, when the bounding curves 2506B, 2510B are closer to the lot 2508B, it indicates a higher level of confidence. Bounding curves 2506A, 2510A, 2506B, 2510B can be confidence indicators. For example, bounding curves 2506A, 2510A, 2506B, 2510B can be included on the graph 2505A, 2505B when the displayed analyte values are based on raw sensor signal data from break-in and omitted otherwise.

FIG. 26 shows another set of UI screens 2602A, 2602B. In FIG. 26, the UI screen 2602B shows an analyte concentration value 2604B with an associated trend shape 2612. The trend shape 2612, in this example, points down, indicating the level of analyte concentration in the host is trending down. In the UI screen 2602A, the trend shape is omitted. In some example, the display of the analyte concentration value 2604A without a trend shape is a confidence indicator.

In the example of FIG. 26, the UI screens 2602A, 2602B also include respective graphs 2605A, 2605B. The presence of bounding curves 2606A, 2610A around the analyte concentration curve 2608A can be a confidence indicator that indicates a lower level of confidence in the displayed analyte concentration value. On the other hand, the absence of bounding curves around the analyte concentration curve 2608B at UI screen 2602B can indicate a higher level of confidence. FIG. 27 shows example UI screens 2702A, 2702B including analyte concentration values 2604A, 2604B and an alternative trend shape 2712. In this example, the trend shape 2712 is an arrow that is separate from the analyte concentration values 2604A, 2604B.

FIG. 28 shows another set of example UI screens 2802A, 2802B. In the example UI screens 2802A, 2802B, the font of the analyte concentration values 2804A, 2804B is a confidence indicator. For example, the analyte concentration value 2804A in UI screen 2802A is in a first font and the analyte concentration value 2804B in the UI screen 2802B is in a second font. The first font, indicating less confidence in the analyte concentration value, may be a more rounded, irregular font, such as Comic Sans while the second font is a more angular font such as Arial.

The example UI screens 2802A, 2802B also shows graphs 2805A, 2805B including respective analyte concentration curves 2810A, 2810B of analyte concentration values over time. Error bars 2808, 2810 are confidence indicators that indicate the confidence in analyte concentration values. For example, larger error bar 2808 indicate a lower level of confidence than smaller error bar 2810.

Figure 36:
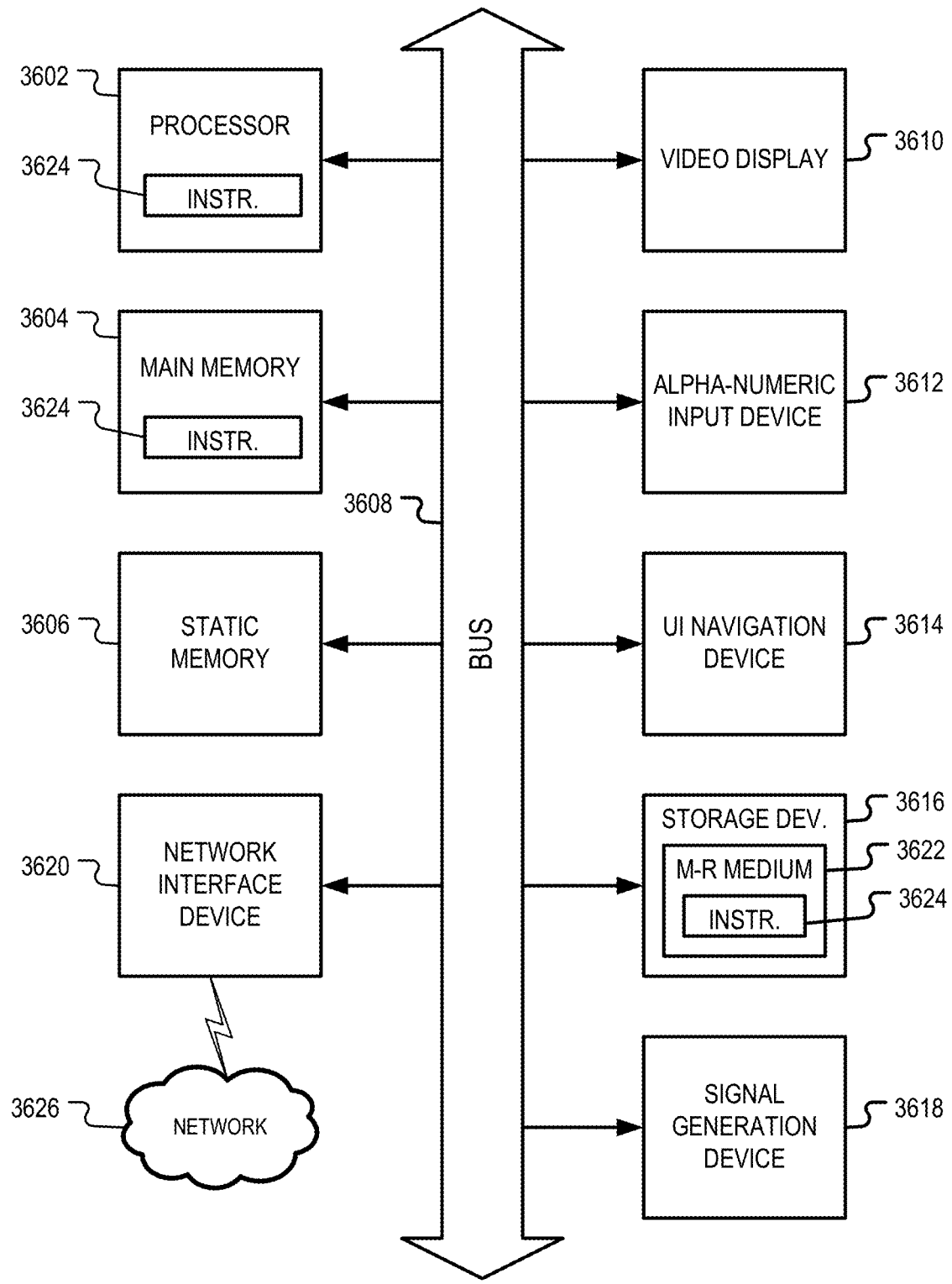
FIG. 36 is a block diagram illustrating a computing device hardware architecture, within which a set or sequence of instructions can be executed to cause a machine to perform examples of any one of the methodologies discussed herein.

FIG. 36 is a block diagram illustrating a computing device hardware architecture 3600, within which a set or sequence of instructions can be executed to cause a machine to perform examples of any one of the methodologies discussed herein. The hardware architecture 3600 can describe various computing devices including, for example, the sensor electronics 106, the peripheral medical device 122, the smart device 112, the tablet 114, etc.

The architecture 3600 may operate as a standalone device or may be connected (e.g., networked) to other machines. In a networked deployment, the architecture 3600 may operate in the capacity of either a server or a client machine in server-client network environments, or it may act as a peer machine in peer-to-peer (or distributed) network environments. The architecture 3600 can be implemented in a personal computer (PC), a tablet PC, a hybrid tablet, a set-top box (STB), a personal digital assistant (PDA), a mobile telephone, a web appliance, a network router, a network switch, a network bridge, or any machine capable of executing instructions (sequential or otherwise) that specify operations to be taken by that machine.

The example architecture 3600 includes a processor unit 3602 comprising at least one processor (e.g., a central processing unit (CPU), a graphics processing unit (GPU), or both, processor cores, compute nodes). The architecture 3600 may further comprise a main memory 3604 and a static memory 3606, which communicate with each other via a link 3608 (e.g., bus). The architecture 3600 can further include a video display unit 3610, an input device 3612 (e.g., a keyboard), and a UI navigation device 3614 (e.g., a mouse). In some examples, the video display unit 3610, input device 3612, and UI navigation device 3614 are incorporated into a touchscreen display. The architecture 3600 may additionally include a storage device 3616 (e.g., a drive unit), a signal generation device 3618 (e.g., a speaker), a network interface device 3620, and one or more sensors (not shown), such as a Global Positioning System (GPS) sensor, compass, accelerometer, or other sensor.

In some examples, the processor unit 3602 or another suitable hardware component may support a hardware interrupt. In response to a hardware interrupt, the processor unit 3602 may pause its processing and execute an ISR, for example, as described herein.

The storage device 3616 includes a machine-readable medium 3622 on which is stored one or more sets of data structures and instructions 3624 (e.g., software) embodying or used by any one or more of the methodologies or functions described herein. The instructions 3624 can also reside, completely or at least partially, within the main memory 3604, within the static memory 3606, and/or within the processor unit 3602 during execution thereof by the architecture 3600, with the main memory 3604, the static memory 3606, and the processor unit 3602 also constituting machine-readable media.

Executable Instructions and Machine-Storage Medium

The various memories (i.e., 3604, 3606, and/or memory of the processor unit(s) 3602) and/or storage device 3616 may store one or more sets of instructions and data structures (e.g., instructions) 3624 embodying or used by any one or more of the methodologies or functions described herein. These instructions, when executed by processor unit(s) 3602 cause various operations to implement the disclosed examples.

As used herein, the terms "machine-storage medium," "device-storage medium," "computer-storage medium" (referred to collectively as "machine-storage medium 3622") mean the same thing and may be used interchangeably in this disclosure. The terms refer to a single or multiple storage devices and/or media (e.g., a centralized or distributed database, and/or associated caches and servers) that store executable instructions and/or data, as well as cloud-based storage systems or storage networks that include multiple storage apparatus or devices. The terms shall accordingly be taken to include, but not be limited to, solid-state memories, and optical and magnetic media, including memory internal or external to processors. Specific examples of machine-storage media, computer-storage media, and/or device-storage media 3622 include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms machine-storage media, computer-storage media, and device-storage media 3622 specifically exclude carrier waves, modulated data signals, and other such media, at least some of which are covered under the term "signal medium" discussed below.

Signal Medium

The term "signal medium" or "transmission medium" shall be taken to include any form of modulated data signal, carrier wave, and so forth. The term "modulated data signal" means a signal that has one or more of its characteristics set or changed in such a matter as to encode information in the signal.

Computer-Readable Medium

The terms "machine-readable medium," "computer-readable medium" and "device-readable medium" mean the same thing and may be used interchangeably in this disclosure. The terms are defined to include both machine-storage media and signal media. Thus, the terms include both storage devices/media and carrier waves/modulated data signals.

The instructions 3624 can further be transmitted or received over a communications network 3626 using a transmission medium via the network interface device 3620 using any one of a number of well-known transfer protocols (e.g., HTTP). Examples of communication networks include a LAN, a WAN, the Internet, mobile telephone networks, plain old telephone service (POTS) networks, and wireless data networks (e.g., Wi-Fi, 3G, 4G LTE/LTE-A, 5G or WiMAX networks). The term "transmission medium" shall be taken to include any intangible medium that is capable of storing, encoding, or carrying instructions for execution by the machine, and includes digital or analog communications signals or other intangible media to facilitate communication of such software.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Various components are described in the present disclosure as being configured in a particular way. A component may be configured in any suitable manner. For example, a component that is or that includes a computing device may be configured with suitable software instructions that program the computing device. A component may also be configured by virtue of its hardware arrangement or in any other suitable manner.

The above description is intended to be illustrative, and not restrictive. For example, the above-described examples (or one or more aspects thereof) can be used in combination with others. Other examples can be used, such as by one of ordinary skill in the art upon reviewing the above description. The Abstract is to allow the reader to quickly ascertain the nature of the technical disclosure, for example, to comply with 37 C.F.R. § 1.72(b) in the United States of America. It is submitted with the understanding that it will not be used to interpret or limit the scope or meaning of the claims.

Also, in the above Detailed Description, various features can be grouped together to streamline the disclosure. However, the claims cannot set forth every feature disclosed herein, as examples can feature a subset of said features. Further, examples can include fewer features than those disclosed in a particular example. Thus, the following claims are hereby incorporated into the Detailed Description, with each claim standing on its own as a separate example. The scope of the examples disclosed herein is to be determined with reference to the appended claims, along with the full scope of equivalents to which such claims are entitled.

Each of these non-limiting examples in any portion of the above description may stand on its own or may be combined in various permutations or combinations with one or more of the other examples.

The above detailed description includes references to the accompanying drawings, which form a part of the detailed description. The drawings show, by way of illustration, specific embodiments in which the subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," "third," etc., are used merely as labels, and are not intended to impose numerical requirements on their objects.

Geometric terms, such as "parallel", "perpendicular", "round", or "square" are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the subject matter should be determined with reference to the claims, along with the full scope of equivalents to which such claims are entitled.

What is claimed is:

1. An analyte sensor system comprising:
   an implantable analyte sensor configured to be inserted into a host and continuously monitor at least one analyte;
   an adhesive pad configured to be at least partially in contact with a skin surface of the host;
   a heating element included in the adhesive pad and positioned to provide heat to the skin surface of the host when the implantable analyte sensor is inserted into the host; and
   sensor electronics hardware, wherein the sensor electronics hardware is configured to perform operations comprising:
   detecting, by the sensor electronics hardware, that the implantable analyte sensor has been inserted into the host based at least on receiving a signal indicating a change in an electrical property of the implantable analyte sensor;
   responsive to receiving the signal indicating the change in the electrical property of the implantable analyte sensor, triggering, by the sensor electronics hardware, power to be provided to the heating element, thereby providing heat to the skin surface of the host upon detection that the implantable analyte sensor has been inserted into the host, wherein the providing of the power to the heating element occurs while the implantable analyte sensor is inserted into the host;
   responsive to determining that a relationship between a response signal generated by the implantable analyte sensor and a corresponding concentration of the at least one analyte is non-linear, continuing to provide power to the heating element; and
   responsive to determining that the relationship is linear after previously determining that the response signal is non-linear, ceasing to provide power to the heating element.

2. The analyte sensor system of claim 1, wherein the heating element includes an electrically resistive material.

3. The analyte sensor system of claim 1, wherein the adhesive pad comprises a permeability-enhancing substance.

4. The analyte sensor system of claim 1, further comprising:
   a sensor mounting unit comprising a first contact and a second contact; and
   a battery electrically coupled to the implantable analyte sensor at the sensor mounting unit, the battery configured to provide a bias voltage across the first contact and the second contact.

5. The analyte sensor system of claim 1, wherein the heating element includes electrically resistive wires that are adhered to and/or woven into the adhesive pad.

6. The analyte sensor system of claim 1, wherein the sensor electronics hardware further comprises contacts, and wherein detecting that the implantable analyte sensor has been inserted into the host includes detecting that the implantable analyte sensor is coupled to the contacts.

7. The analyte sensor system of claim 1, further comprising:
   a second heating element included in the adhesive pad and positioned to provide heat to the skin surface of the host when the implantable analyte sensor is inserted into the host.

8. An analyte sensor system comprising:
   an implantable analyte sensor configured to be inserted into a host and continuously monitor at least one analyte;
   a sensor mounting unit, the implantable analyte sensor coupled to the sensor mounting unit;
   an adhesive pad coupled to the sensor mounting unit to adhere the sensor mounting unit to a skin surface of the host;
   a heating element included in the adhesive pad and positioned to provide heat to the skin surface of the host when the implantable analyte sensor is inserted into the host; and
   a sensor electronics unit installable to the sensor mounting unit, wherein the sensor electronics unit is configured to:
   detect that the implantable analyte sensor has been inserted into the host based at least on receiving a signal indicating a change in an electrical property of a contact of the implantable analyte sensor,
   begin, in response to receiving the signal indicating the change in the electrical property of the contact of the implantable analyte sensor, providing power to the heating element to heat the skin surface of the host after being installed to the sensor mounting unit, the providing of the power to the heating element being while the implantable analyte sensor is inserted into the host,
   responsive to determining that a relationship between a response signal generated by the implantable analyte sensor and a corresponding concentration of the at least one analyte is non-linear, continuing to provide power to the heating element; and responsive to determining that the relationship is linear after previously determining that the response signal is non-linear, ceasing to provide power to the heating element.

9. The analyte sensor system of claim 8, wherein the heating element includes an electrically resistive material.

10. The analyte sensor system of claim 8, wherein the heating element includes electrically resistive wires that are adhered to and/or woven into the adhesive pad.

11. The analyte sensor system of claim 8, wherein the sensor electronics unit further comprises contacts, and wherein detecting that the implantable analyte sensor has been inserted into the host includes detecting that the implantable analyte sensor is coupled to the contacts.

12. The analyte sensor system of claim 8, further comprising:
    a second heating element included in the adhesive pad and positioned to provide heat to the skin surface of the host when the implantable analyte sensor is inserted into the host.

13. An analyte sensor system comprising:
    an implantable analyte sensor configured to continuously monitor at least one analyte;
    a sensor mounting unit, the implantable analyte sensor being coupled to the sensor mounting unit;
    an adhesive pad coupled to the sensor mounting unit configured to adhere the sensor mounting unit to a skin surface of a host;
    a heating element coupled to the adhesive pad; and
    sensor electronics hardware configured to provide power to the heating element;
    wherein the sensor electronics hardware is configured to perform operations comprising:
        detecting, by the sensor electronics hardware, that the implantable analyte sensor has been inserted into the host based at least on detecting contact between the implantable analyte sensor and the skin surface of the host or proximity of the implantable analyte sensor to the skin surface of the host;
        in response to detecting contact between the implantable analyte sensor and the skin surface of the host or proximity of the implantable analyte sensor to the skin surface of the host, providing, by the sensor electronics hardware, power to the heating element, thereby providing heat to the skin surface of the host;
        in response to determining that a relationship between a response signal generated by the implantable analyte sensor and a corresponding concentration of the at least one analyte is non-linear, continuing to provide power to the heating element, thereby continuing to provide heat to the skin surface of the host; and
        in response to determining that the relationship is linear while the heat is provided to the skin surface of the host and after previously determining that the response signal is non-linear, ceasing to provide power to the heating element.

14. The analyte sensor system of claim 13, wherein the sensor mounting unit comprises a first contact and a second contact, the analyte sensor system further comprising:
    a battery electrically coupled to the implantable analyte sensor at the sensor mounting unit, the battery configured to provide a bias voltage across the first contact and the second contact to the implantable analyte sensor.

15. The analyte sensor system of claim 13, wherein the heating element includes an electrically resistive material.

* * * * *